(12) United States Patent
Metz et al.

(10) Patent No.: US 10,374,172 B2
(45) Date of Patent: Aug. 6, 2019

(54) AZABENZIMIDAZOLE CARBENE COMPLEXES AS EFFICIENCY BOOSTER IN OLEDS

(71) Applicant: UDC Ireland Limited, Dublin (IE)

(72) Inventors: Stefan Metz, Mannheim (DE); Soichi Watanabe, Ludwigshafen (DE); Thomas Geßner, Heidelberg (DE); Korinna Dormann, Bad Dürkheim (DE); Peter Murer, Oberwil (CH); Christian Lennartz, Schifferstadt (DE); Ute Heinemeyer, Neustadt (DE); Glauco Battagliarin, Mannheim (DE)

(73) Assignee: UDC Ireland Limited, Dublin (IE)

( * ) Notice: Subject to any disclaimer, the term of this patent is extended or adjusted under 35 U.S.C. 154(b) by 369 days.

(21) Appl. No.: 14/778,174

(22) PCT Filed: Mar. 19, 2014

(86) PCT No.: PCT/EP2014/055520
§ 371 (c)(1),
(2) Date: Sep. 18, 2015

(87) PCT Pub. No.: WO2014/147134
PCT Pub. Date: Sep. 25, 2014

(65) Prior Publication Data
US 2016/0293862 A1    Oct. 6, 2016

(30) Foreign Application Priority Data

Mar. 20, 2013  (EP) .................................... 13160198
Apr. 8, 2013  (EP) .................................... 13162776

(51) Int. Cl.
| | |
|---|---|
| H01L 51/54 | (2006.01) |
| H01L 51/00 | (2006.01) |
| C09K 11/06 | (2006.01) |
| H01L 51/50 | (2006.01) |
| C07F 15/00 | (2006.01) |
| H05B 33/10 | (2006.01) |

(52) U.S. Cl.
CPC ...... *H01L 51/0085* (2013.01); *C07F 15/0033* (2013.01); *C09K 11/06* (2013.01); *H01L 51/504* (2013.01); *H01L 51/5016* (2013.01); *H05B 33/10* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/0094* (2013.01); *H01L 51/5056* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | |
|---|---|---|
| 2008/0018221 A1 | 1/2008 | Egen et al. |
| 2012/0305894 A1 | 12/2012 | Kim et al. |
| 2013/0032766 A1 | 2/2013 | Molt et al. |

FOREIGN PATENT DOCUMENTS

| | | |
|---|---|---|
| CN | 102762582 | 10/2012 |
| WO | WO-2005113704 A2 | 12/2005 |
| WO | WO-2006056418 A2 | 6/2006 |
| WO | WO-2012172482 A1 | 12/2012 |

OTHER PUBLICATIONS

Baldo, M., et al., "Very high-efficiency green organic light-emitting devices based on electrophosphorescence", Applied Physics Letters, vol. 75, Issue 1, (1999), pp. 4-6.
International Search Report for PCT/EP2014/055520 dated May 20, 2014.
International Preliminary Report on Patentability for PCT/EP2014/055520 dated Sep. 22, 2015.
CN Office Action for CN201480016714.X, dated Oct. 22, 2018, 13 pages.
Office Action and Search Report for TW106137914, dated Sep. 19, 2018, 7 pages.

*Primary Examiner* — Marie R. Yamnitzky
(74) *Attorney, Agent, or Firm* — Riverside Law LLP

(57) ABSTRACT

An organic electronic device comprising at least one hole-transport material and/or at least one electron/exciton blocker material, wherein said at least one hole-transport material and/or said at least one electron/exciton blocker material is an Ir metal-carbene complex comprising one, two or three specific bidentate azabenzimidazole ligands; a hole transport layer or an electron/exciton blocking layer, comprising at least one Ir metal-carbene complex, comprising one, two or three specific bidentate azabenzimidazole ligands; an apparatus selected from the group consisting of stationary visual display units, mobile visual display units, illumination units, units in items of clothing, units in furniture and units in wallpaper, comprising the organic electronic device of the present invention or the hole transport layer or the electron/exciton blocking layer of the present invention; and the use of an Ir metal-carbene complex comprising one, two or three specific bidentate azabenzimidazole ligands according to the present invention as hole-transport material and/or electron/exciton blocker material.

11 Claims, No Drawings

AZABENZIMIDAZOLE CARBENE COMPLEXES AS EFFICIENCY BOOSTER IN OLEDS

CROSS-REFERENCE TO RELATED APPLICATIONS

This application is a national stage application (under 35 U.S.C. § 371) of PCT/EP2014/055520, filed Mar. 19, 2014, which claims benefit of European Application Nos. 13160198.1, filed Mar. 20, 2013, and 13162776.2, filed Apr. 8, 2013, all of which are incorporated herein by reference in their entirety.

The present invention relates to an organic electronic device, preferably an organic light-emitting diode (OLED), comprising at least one hole-transport material and/or at least one electron/exciton blocker material, wherein said at least one hole-transport material and/or said at least one electron/exciton blocker material is an Ir metal-carbene complex comprising one, two or three specific bidentate azabenzimidazole carbene ligands, to a hole transport layer or an electron/exciton blocking layer comprising said Ir metal-carbene complex, an apparatus selected from the group consisting of stationary visual display units, mobile visual display units, illumination units, units in items of clothing, units in furniture and units in wallpaper comprising said organic electronic device, preferably said OLED, or said hole transport layer or said electron/exciton blocking layer, and to the use of said Ir metal-carbene complex comprising one, two or three specific bidentate azabenzimidazole carbene ligands as hole-transport material and/or electron/exciton blocker material.

Organic electronics, i.e. organic electronic devices, are an important sector in the field of electronics. Organic electronics is a subfield of electronics which uses electronic circuits which comprise polymers or smaller organic compounds. Fields of use of organic electronics are the use of polymers or smaller organic compounds in organic electronic devices, for example in organic light-emitting diodes (OLED), light-emitting electrochemical cells (LEEC), organic photovoltaic cells (OPV) and organic field-effect transistors (OFET).

The use of suitable novel organic materials thus allows various new types of components based on organic electronics to be provided, such as displays, illumination, sensors, transistors, data stores or photovoltaic cells. This makes possible the development of new devices which are thin, light, flexible and producible at low cost.

The synthesis and provision of new materials for organic electronic devices is therefore an important research topic. Especially the synthesis and provision of novel hole-transport materials and electron/exciton blocker materials for use in organic electronic devices is important for providing organic electronic devices having good stabilities and long lifetimes as well as—in the case of OLEDs and LEECs—high quantum efficiencies.

A preferred field of use according to the present application is the use of relatively small organic compounds in organic light-emitting diodes (OLED). OLEDs exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cellphones, smartphones, digital cameras, mp3 players, tablet computers, laptops, etc. In addition, white OLEDs give great advantage over the illumination technologies known to date, especially a particularly high efficiency.

The basic principles of the way in which OLEDs work and suitable structures (layers) of OLEDs are specified, for example, in WO 2005/113704 and the literature cited therein.

The light-emitting materials (emitters) used may, as well as fluorescent materials (fluorescent emitters), be phosphorescent materials (phosphorescent emitters). The phosphorescent emitters are typically organometallic complexes which, in contrast to the fluorescence emitters which exhibit singlet emission, exhibit triplet emission (M. A. Baldow et al., Appl. Phys. Lett. 1999, 75, 4 to 6). For quantum-mechanical reasons, when the phosphorescent emitters are used, up to four times the quantum efficiency, energy efficiency and power efficiency is possible.

Of particular interest are organic light-emitting diodes with a low operational voltage, high efficiency, high efficacy, high resistance to thermal stress and long operational lifetime.

In order to implement the aforementioned properties in practice, it is not only necessary to provide suitable emitter materials, but also to provide suitable complementary materials. Such device compositions may, for example, comprise specific host (matrix) materials in which the actual light emitter is present in distributed form. In addition, the compositions may comprise blocker materials, it being possible for hole blockers, exciton blockers and/or electron blockers to be present in the device compositions. Additionally or alternatively, the device compositions may further comprise hole injection materials and/or electron injection materials and/or charge transport materials such as hole-transport materials and/or electron-transport materials. The selection of the aforementioned materials which are used in combination with the actual light emitter has a significant influence on parameters including the efficiency, lifetime and operating voltages of the OLEDs.

The prior art proposes numerous different materials for use in the different layers of OLEDs.

The use of Ir metal-carbene complexes comprising azabenzimidazole carbene ligands has only been described in a few prior art references.

WO 2006/056418 A2 relates to the use of transition metal carbene complexes in OLEDs. The transition metal carbene complexes of WO 2006/056418 A2 are unsymmetrical carbene complexes of the following formula,

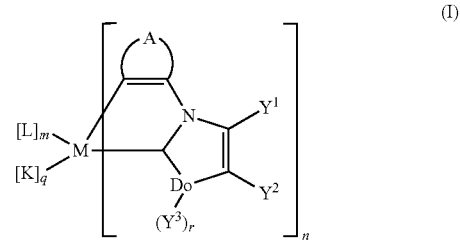

wherein $Y^3$ is a non aromatic radical, i.e. hydrogen or alkyl, or forms a bridge with $Y^2$. In example 4 in WO 2006/056418 A2 an Ir metal-carbene complex comprising three specific azabenzimidazole carbene ligands is disclosed. However, said Ir metal carbene compex is an unsymmetrical complex ($Y^3$ in formula (I) mentioned above is methyl), wherein the nitrogen atom is in the 5-position of the azabenzimidazole ring. According to example 17 in WO 2006/056418 A2 Ir(DPBIC)$_3$ is used as hole-transport and exciton blocker material

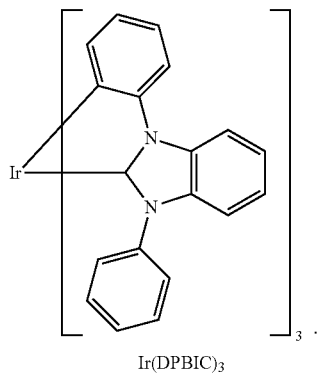

Ir(DPBIC)$_3$

WO 2012/172482 A1 relates to metal-carbene complexes comprising a central atom selected from iridium and platinum, and specific azabenzimidazole carbene ligands and to OLEDs (Organic Light-Emitting Diodes) which comprise such complexes. The complexes having the following formula:

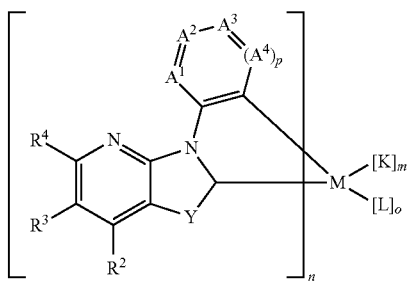
(I)

wherein
Y is NR$^1$, O, S or C(R$^{10}$)$_2$;
R$^1$ is a linear or branched alkyl radical optionally interrupted by at least one heteroatom, optionally bearing at least one functional group and having 1 to 20 carbon atoms, substituted or unsubstituted cycloalkyi radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms.

US 2012/0305894 A1 relates to a blue phosphorescent compound with a high color purity and a high efficiency and an organic electroluminescenct device using the same. The blue phosphorecent compound according to US 2012/0305894 A1 is characterized by the following formula:

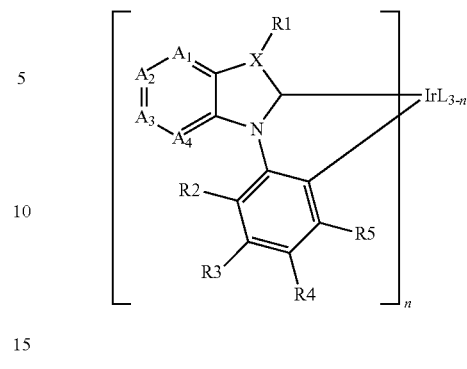
[Formula 1]

wherein
X is selected from nitrogen (N), oxygen (O), phosphorous (P) and sulfur (S) atoms; and
at least one of A1, A2, A3 and A4 is nitrogen (N), and the remaining are selected from hydrogen (H)-substituted carbon, and an alkyl- or alkoxy-substituted carbon. In US 2012/0305894 A1 exclusively the use of said compounds as phosphorescent emitter material is mentioned.

It is an object of the present invention to provide stable organic electronic devices, preferably OLEDs, compared with the organic electronic devices known in the art. It is a further object of the present invention to provide more stable and/or more efficient OLEDs compared with the OLEDs known in the art, especially OLEDs which emit light in the blue region of the electromagnetic spectrum which are more stable and/or more efficient.

This object is achieved by an organic electronic device, preferably an OLED, comprising at least one hole-transport material and/or at least one electron/exciton blocker material, wherein said at least one hole-transport material and/or said at least one electron/exciton blocker material is an Ir metal-carbene complex comprising one, two or three, preferably three, bidentate ligands of formula (I) and/or (I')

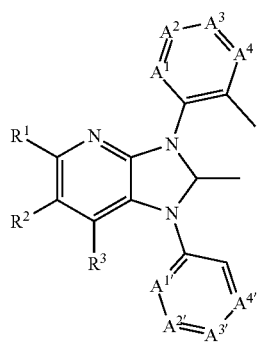
(I)

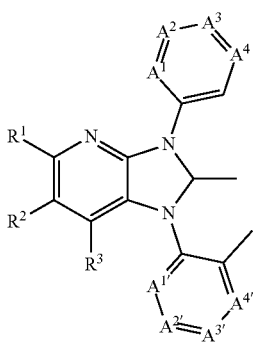

(I')

wherein
R$^1$, R$^2$ and R$^3$
are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably, R$^1$, R$^2$ and R$^3$ are each independently hydrogen, a linear or branched alkyl radical, having from 1 to 6 carbon atoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from the group consisting of halogen radicals, preferably F or Cl, more preferably F; CF$_3$, SiPh$_3$ and SiMe$_3$;
or
R$^1$ and R$^2$ or R$^2$ and R$^3$ form, independently of each other, together with a carbon atom to which they are bonded an optionally substituted saturated or unsaturated or aromatic ring, optionally interrupted by at least one heteroatom and having a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;
A$^1$ is CR$^4$ or N, preferably CR$^4$;
A$^2$ is CR$^5$ or N, preferably CR$^5$;
A$^3$ is CR$^6$ or N, preferably CR$^6$;
A$^4$ is CR$^7$ or N, preferably CR$^7$;
A$^{1'}$ is CR$^{4'}$ or N, preferably CR$^{4'}$;
A$^{2'}$ is CR$^{5'}$ or N, preferably CR$^{5'}$;
A$^{3'}$ is CR$^{6'}$ or N, preferably CR$^{6'}$;
A$^{4'}$ is CR$^{7'}$ or N, preferably CR$^{7'}$;
R$^4$, R$^5$, R$^6$, R$^7$, R$^{4'}$, R$^{5'}$, R$^{6'}$ and R$^{7'}$
are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having from 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably, R$^4$, R$^5$, R$^6$, R$^7$, R$^{4'}$, R$^{5'}$, R$^{6'}$ and are each independently hydrogen, a linear or branched alkyl radical, optionally bearing at least one functional group, optionally interrupted by at least one heteroatom and having a total of from 1 to 20 carbon and/or heteroatoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from halogen radicals, preferably F or Cl, more preferably F; CF$_3$, CN, SiPh$_3$ and SiMe$_3$;
or
R$^4$ and R$^5$, R$^5$ and R$^6$ or R$^6$ and R$^7$ or R$^{4'}$ and R$^{5'}$, R$^{5'}$ and R$^{6'}$ or R$^{6'}$ and form, independently of each other, together with the carbon atoms to which they are bonded, a saturated or unsaturated or aromatic, optionally substituted ring, which is optionally interrupted by at least one heteroatom, has a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms.

It has been found by the inventors of the present invention that stable organic electronic devices, preferably OLEDs, having a long lifetime are obtained by employing the Ir metal-carbene complex comprising one, two or three, preferably three, bidentate ligands of formula (I) and/or (I') as mentioned above as hole-transport material and/or as electron/exciton blocker material.

It has further been found by the inventors of the present invention that OLEDs comprising the Ir metal-carbene complex comprising one, two or three, preferably three, bidentate ligands of formula (I) and/or (I') as mentioned above as hole-transport material and/or as electron/exciton blocker material show high quantum efficiencies and/or good stabilities and long lifetimes.

The complexes are particularly suitable as hole-transport materials and/or as electron/exciton blocker materials for OLEDs showing electroluminescence in the blue region, more particularly in the deep blue region, of the electromagnetic spectrum, which enables, for example, the production of full-color displays and white OLEDs. When used to work as exciton blocking materials for blue emitters said inventive complexes need to have suitable high triplet energies which requires emission maxima of <500 nm, preferably <470 nm, more preferably <445 nm.

Preferably, the Ir metal-carbene complex comprising one, two or three, preferably three, bidentate ligands of formula (I) and/or(I') as mentioned above is present in a hole transport layer of the organic electronic device, preferably the OLED, and/or the at least one electron/exciton blocker material, comprising the Ir metal-carbene complex comprising one, two or three bidentate ligands of formula (I) and/or (I') is present in an electron-blocking layer of the organic electronic device, preferably the OLED.

In the context of the present invention, the terms aryl radical, unit or group, heteroaryl radical, unit or group, alkyl radical, unit or group, cycloalkyl radical, unit or group, cycloheteroalkyl radical, unit or group, and groups with donor or acceptor action are each defined as follows—unless stated otherwise:

In the aryl radicals, heteroaryl radicals, alkyl radicals, cycloalkyl radicals, cycloheteroalkyl radicals and groups with donor or acceptor action mentioned below, one or more hydrogen atoms (if present) may be substituted by deuterium atoms.

Aryl radicals or substituted or unsubstituted aryl radicals having 6 to 30 carbon atoms ($C_6$-$C_{30}$-aryl radicals) refer in the present invention to radicals which are derived from monocyclic, bicyclic or tricyclic aromatics which do not comprise any ring heteroatoms. When the systems are not monocyclic systems, the term "aryl" for the second ring also includes the saturated form (perhydro form) or the partly unsaturated form (for example the dihydro form or tetrahydro form), provided that the particular forms are known and stable. This means that the term "aryl" in the present invention encompasses, for example, also bicyclic or tricyclic radicals in which either both or all three radicals are aromatic, and bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to $C_6$-$C_{10}$-aryl radicals, for example phenyl or naphthyl, very particular preference to $C_6$-aryl radicals, for example phenyl.

The aryl radicals or $C_6$-$C_{30}$-aryl radicals may be unsubstituted or substituted by one or more further radicals. Suitable further radicals are selected from the group consisting of $C_1$-$C_{20}$-alkyl, $C_6$-$C_{30}$-aryl and substituents with donor or acceptor action, suitable substituents with donor or acceptor action are specified below. The $C_6$-$C_{30}$-aryl radicals are preferably unsubstituted or substituted by one or more $C_1$-$C_{20}$-alkyl groups, $C_1$-$C_{20}$-alkoxy groups, CN, $CF_3$, F, $SiMe_3$ or amino groups ($NR^{32}R^{33}$ where suitable $R^{32}$ and $R^{33}$ radicals are specified below), more preferably unsubstituted (e.g. $C_6H_5$), o-monosubstituted or o,o'-disubstituted by one respectively two $C_1$-$C_{20}$-alkyl groups, $C_1$-$C_{20}$-alkoxy groups, CN, $CF_3$, F, $SiMe_3$ or amino groups ($NR^{32}R^{33}$ where suitable $R^{32}$ and $R^{33}$ radicals are specified below).

Heteroaryl radicals or substituted or unsubstituted heteroaryl radicals having a total of 5 to 18 carbon atoms and/or heteroatoms are understood to mean monocyclic, bicyclic or tricyclic heteroaromatics, some of which can be derived from the aforementioned aryl, in which at least one carbon atom in the aryl base structure has been replaced by a heteroatom. Preferred heteroatoms are N, O and S. The heteroaryl radicals more preferably have 5 to 13 ring atoms. The base structure of the heteroaryl radicals is especially preferably selected from systems such as pyridine and five-membered heteroaromatics such as thiophene, pyrrole, imidazole, thiazole, oxazole or furan. These base structures may optionally be fused to one or two six-membered aromatic radicals. Suitable fused heteroaromatics are carbazolyl, benzimidazolyl, benzofuryl, benzothiazole, benzoxazole, dibenzofuryl or dibenzothiophenyl.

The base structure may be substituted at one, more than one or all substitutable positions, suitable substituents being the same as those already specified under the definition of $C_6$-$C_{30}$-aryl. However, the heteroaryl radicals are preferably unsubstituted, o-monosubstituted or o,o'-disubstituted by one respectively two $C_1$-$C_{20}$-alkyl groups, $C_1$-$C_{20}$-alkoxy groups, CN, $CF_3$, F, $SiMe_3$ or amino groups ($NR^{32}R^{33}$ where suitable $R^{32}$ and $R^{33}$ radicals are specified below). Suitable heteroaryl radicals are, for example, pyridin-2-yl, pyridin-3-yl, pyridin-4-yl, thiophen-2-yl, thiophen-3-yl, pyrrol-2-yl, pyrrol-3-yl, furan-2-yl, furan-3-yl, thiazol-2-yl, oxazol-2-yl and imidazol-2-yl, and the corresponding benzofused radicals, especially carbazolyl, benzimidazolyl, benzofuryl, benzothiazole, benzoxazole, dibenzofuryl or dibenzothiophenyl.

An alkyl radical in the context of the present application is a linear or branched alkyl radical optionally bearing at least one functional group, optionally interrupted by at least one heteroatom and having 1 to 20 carbon atoms. Preference is given to $C_1$- to $C_{10}$-alkyl radicals, particular preference to $C_1$- to $C_6$-alkyl radicals. In addition, the alkyl radicals may be substituted by one or more functional groups, preferably selected from the group consisting of $C_1$-$C_{20}$-alkyl, $C_1$-$C_{20}$-alkoxy, halogen, preferably F, $C_1$-$C_{20}$-haloalkyl, e.g. $CF_3$, and $C_6$-$C_{30}$-aryl which may in turn be substituted or unsubstituted. Suitable aryl substituents and suitable alkoxy and halogen substituents are specified below. Examples of suitable alkyl groups are methyl, ethyl, propyl, butyl, pentyl, hexyl, heptyl and octyl, and also $C_1$-$C_{20}$-alkyl-, $C_6$-$C_{30}$-aryl-, $C_1$-$C_{20}$-alkoxy- and/or halogen-substituted, especially F-substituted, derivatives of the alkyl groups mentioned, for example $CF_3$. This comprises both the n-isomers of the radicals mentioned and branched isomers such as isopropyl, isobutyl, isopentyl, sec-butyl, tert-butyl, neopentyl, 3,3-dimethylbutyl, 3-ethylhexyl, etc. Preferred alkyl groups are methyl, ethyl, isopropyl, sec-butyl, tert-butyl and $CF_3$.

A cycloalkyl radical or a substituted or unsubstituted cycloalkyl radical having 3 to 20 carbon atoms is understood in the context of the present application to mean a substituted or unsubstituted $C_3$-$C_{20}$-cycloalkyl radical. Preferred are cycloalkyl radicals having 5 to 20, more preferably 5 to 10 and most preferably 5 to 8 carbon atoms in the base structure (ring) to understand. Suitable substituents are the substituents mentioned for the alkyl groups. Examples of suitable cycloalkyl groups, which may be unsubstituted or substituted by the radicals mentioned above for the alkyl groups, are cyclopentyl, cyclohexyl, cycloheptyl, cyclooctyl, cyclononyl and cyclodecyl. They may also be polycyclic ring systems such as decalinyl, norbornyl, bornanyl or adamantyl.

A heterocycloalkyl radical or a substituted or unsubstituted heterocycloalkyl radical having 3 to 20 carbon atoms and/or heteroatoms is understood to mean heterocycle-alkyl radicals having 3 to 20, preferably 5 to 10 and more preferably 5 to 8 ring atoms, where at least one carbon atom in the heterocycloalkyl base structure has been replaced by a heteroatom. Preferred heteroatoms are N, O and S. Suitable substituents are the substituents mentioned for the alkyl groups. Examples of suitable heterocycloalkyl groups, which may be unsubstituted or substituted by the radicals mentioned above for the alkyl groups, are radicals derived from the following heterocycles: pyrrolidine, thiolane, tetrahydrofuran, 1,2-oxathiolane, oxazolidine, piperidine, thiane, oxane, dioxane, 1,3-dithiane, morpholine, piperazine. They may also be polycyclic ring systems.

Suitable alkoxy radicals and alkylthio radicals derive correspondingly from the aforementioned alkyl radicals. Examples here include $OCH_3$, $OC_2H_5$, $OC_3H_7$, $OC_4H_9$ and $OC_8H_{17}$, and also $SCH_3$, $SC_2H_5$, $SC_3H_7$, $SC_4H_9$ and $SC_8H_{17}$. In this context, $C_3H_7$, $C_4H_9$ and $C_5H_{17}$ comprise both the n-isomers and branched isomers such as isopropyl, isobutyl, sec-butyl, tert-butyl and 2-ethylhexyl. Particularly preferred alkoxy or alkylthio groups are methoxy, ethoxy, n-octyloxy, 2-ethylhexyloxy and SCH$_3$.

Suitable halogen radicals or halogen substituents in the context of the present application are fluorine, chlorine, bromine and iodine, preferably fluorine, chlorine and bromine, more preferably fluorine and chlorine, most preferably fluorine.

In the context of the present application, groups with donor or acceptor action are understood to mean the following groups:

$C_1$-$C_{20}$-alkoxy, $C_6$-$C_{30}$-aryloxy, $C_1$-$C_{20}$-alkylthio, $C_6$-$C_{30}$-arylthio, $SiR^{32}R^{33}R^{34}$, halogen radicals, halogenated $C_1$-$C_{20}$-alkyl radicals, carbonyl (—CO($R^{32}$)), carbonylthio (—C=O($SR^{32}$)), carbonyloxy (—C=O($OR^{32}$)), oxycarbonyl (—OC=O($R^{32}$)), thiocarbonyl (—SC=O ($R^{32}$)), amino (—$NR^{32}R^{33}$), OH, pseudohalogen radicals, amido (—C=O($NR^{32}R^{33}$)), —$NR^{32}$C=O($R^{33}$), phosphonate (—P(O) ($OR^{32}$)$_2$, phosphate (—OP(O) ($OR^{32}$)$_2$), phosphine (—$PR^{32}R^{33}$), phosphine oxide (—P(O)$R^{32}_2$), sulfate (OS(O)$_2$$OR^{32}$), sulfoxide (—S(O)$R^{32}$), sulfonate (—S(O)$_2$$OR^{32}$), sulfonyl (—S(O)$_2$$R^{32}$), sulfonamide (—S (O)$_2$$NR^{32}R^{33}$), NO$_2$, boronic esters (—OB($OR^{32}$)$_2$), imino (—C=$NR^{32}R^{33}$)), borane radicals, stannate radicals, hydrazine radicals, hydrazone radicals, oxime radicals, nitroso groups, diazo groups, vinyl groups, sulfoximines, alanes, germanes, boroxines and borazines.

Preferred substituents with donor or acceptor action are selected from the group consisting of: $C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{32}R^{33}R^{34}$, where $R^{32}$, $R^{33}$ and $R^{34}$ are preferably each independently substituted or unsubstituted alkyl or substituted or unsubstituted phenyl, suitable substituents having been specified above; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. CF$_3$, CH$_2$F, CHF$_2$ or C$_2$F$_5$; amino, preferably dimethylamino, diethylamino or diphenylamino; OH, pseudohalogen radicals, preferably CN, SCN or OCN, more preferably CN, —C(O)O$C_1$-$C_4$-alkyl, preferably —C(O)OMe, P(O)$R_2$, preferably P(O)Ph$_2$, and SO$_2$R$_2$, preferably SO$_2$Ph.

Very particularly preferred substituents with donor or acceptor action are selected from the group consisting of methoxy, phenyloxy, halogenated $C_1$-$C_4$-alkyl, preferably CF$_3$, CH$_2$F, CHF$_2$, C$_2$F$_5$, halogen, preferably F, CN, $SiR^{32}R^{33}R^{34}$, where suitable $R^{32}$, $R^{33}$ and $R^{34}$ radicals are specified below, diphenylamino, —C(O)O$C_1$-$C_4$-alkyl, preferably
—C(O)OMe, P(O)Ph$_2$ and SO$_2$Ph.

The aforementioned groups with donor or acceptor action are not intended to rule out the possibility that further radicals and groups among those specified above may also have donor or acceptor action. For example, the aforementioned heteroaryl radicals are likewise groups with donor or acceptor action, and the $C_1$-$C_{20}$-alkyl radicals are groups with donor action.

The $R^{32}$, $R^{33}$ and $R^{34}$ radicals mentioned in the aforementioned groups with donor or acceptor action are each independently:

Hydrogen, substituted or unsubstituted $C_1$-$C_{20}$-alkyl or substituted or unsubstituted $C_6$-$C_{30}$-aryl or substituted or unsubstituted heteroaryl having 5 to 30 ring atoms, suitable and preferred alkyl and aryl radicals having been specified above. More preferably, the $R^{32}$, $R^{33}$ and $R^{34}$ radicals are $C_1$-$C_6$alkyl, e.g. methyl, ethyl, i-propyl or tert-butyl, or phenyl or pyridyl.

Structures of the Organic Electronic Devices

Suitable structures of the organic electronic devices are known to those skilled in the art. Preferred organic electronic devices are selected from organic light-emitting diodes (OLED), light-emitting electrochemical cells (LEEC), organic photovoltaic cells (OPV) and organic field-effect transistors (OFET). More preferred organic electronic devices are OLEDs.

The organic light-emitting diode (OLED) is usually a light-emitting diode (LED) in which the emissive electroluminescent layer is a film of organic compound which emits light in response to an electric current. This layer of organic semiconductor is usually situated between two electrodes. Generally, at least one of these electrodes is transparent. The Ir metal-carbene complex comprising one, two or three, preferably three, bidentate ligands of formula (I) and/or (I') may be present in any desired layer, preferably in the hole transport layer and/or electron/exciton blocking layer, of the OLED as hole transport material and/or electron/exciton blocker material.

The light-emitting electrochemical cell (LEEC) is usually a solid-state device that generates light from an electric current (electroluminescence). LEEC's are usually composed of two metal electrodes connected by (e.g. sandwiching) an organic semiconductor containing mobile ions. Aside from the mobile ions, their structure is very similar to that of an organic light-emitting diode (OLED). The Ir metal-carbene complex comprising one, two or three, preferably three, bidentate ligands of formula (I) and/or (I') may be present in any desired layer as hole transport material and/or electron/exciton blocker material.

The organic field-effect transistor (OFET) generally includes a semiconductor layer formed from an organic layer with hole transport capacity and/or electron transport capacity; a gate electrode formed from a conductive layer; and an insulation layer introduced between the semiconductor layer and the conductive layer. A source electrode and a drain electrode are mounted on this arrangement in order thus to produce the transistor element. In addition, further layers known to those skilled in the art may be present in the organic transistor. The Ir metal-carbene complex comprising one, two or three, preferably three, bidentate ligands of formula (I) and/or (I') may be present in any desired layer as hole transport material and/or electron/exciton blocker material.

The organic photovoltaic cell (OPV) (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is usually formed from two sublayers, i.e. a layer with p-type semiconductor character or hole transport capacity, and a layer formed with n-type semiconductor character or electron transport capacity. In addition, it is possible for further layers known to those skilled in the art to be present in the organic solar cell. The Ir metal-carbene complex comprising one, two or three, preferably three, bidentate ligands of formula (I) and/or (I') may be present in any desired layer, preferably in the hole transport layer and/or electron/exciton blocking layer, of the OPV as hole transport material and/or electron/exciton blocker material.

The organic electronic device is most preferably an OLED. The present invention therefore preferably relates to an organic electronic device which is an OLED, wherein the OLED comprises
(a) an anode,
(b) a cathode,
(c) a light-emitting layer between the anode and the cathode,
(d) at least one layer, selected from a hole-transport layer (d1) and an electron/exciton blocking layer (d2),
wherein the at least one hole-transport material, comprising the Ir metal-carbene complex comprising one, two or three bidentate ligands of formula (I) and/or (I') is present in the hole-transport layer of the OLED and/or the at least one electron/exciton blocker material, comprising the Ir metal-carbene complex comprising one, two or three bidentate ligands of formula (I) and/or (I') is present in the electron/exciton blocking layer of the OLED.

The structure of the inventive OLED will be described in detail below.

Ir Metal-Carbene Complex Comprising One, Two or Three Bidentate Ligands of Formula (I) and/or (I')

The radicals, groups and symbols in the bidentate ligands of formula (I) and/or (I') of the Ir metal-carbene complex preferably have—independently of each other—the following meanings:

$R^1$, $R^2$ and $R^3$ are each independently hydrogen, a linear or branched alkyl radical, having from 1 to 6 carbon atoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from the group consisting of halogen radicals, preferably F or Cl, more preferably F; $CF_3$, CN, $SiPh_3$ and $SiMe_3$; more preferably hydrogen, a linear or branched alkyl radical, having from 1 to 4 carbon atoms, an unsubstituted aryl radical, having from 6 to 18 carbon atoms (e.g. $C_6H_5$), an o-monosubstituted aryl radical having from 6 to 18 carbon atoms, an o,o'-disubstituted aryl radical having from 6 to 18 carbon atoms, an unsubstituted heteroaryl radical, having a total of from 5 to 15 carbon atoms and/or heteroatoms, an o-monosubstituted heteroaryl radical, having a total of from 5 to 15 carbon atoms and/or heteroatoms, an o,o'-disubstituted heteroaryl radical, having a total of from 5 to 15 carbon atoms and/or heteroatoms, a group with donor or acceptor action, selected from the group consisting of F, $CF_3$, $SiPh_3$ and $SiMe_3$; most preferably hydrogen, an o-monoalkylated phenyl radical or an o,o'-dialkylated phenyl radical, preferably o,o'-dimethyl phenyl or o,o'-diisopropyl phenyl;
or
$R^1$ and $R^2$ or $R^2$ and $R^3$ form, independently of each other, together with a carbon atom to which they are bonded an optionally substituted saturated or unsaturated or aromatic ring, optionally interrupted by at least one heteroatom and having a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;
A1 is $CR^4$;
$A^2$ is $CR^5$;
$A^3$ is $CR^6$;
$A^4$ is $CR^7$;
$A^{1'}$ is $CR^{4'}$;
$A^{2'}$ is $CR^{5'}$;
$A^{3'}$ is $CR^{6'}$;
$A^{4'}$ is $CR^{7'}$;
$R^4$, $R^5$, $R^6$, $R^7$, $R^{4'}$, $R^{5'}$, $R^{6'}$ and $R^{7'}$ are each independently hydrogen, deuterium, a linear or branched alkyl radical, optionally bearing at least one functional group, optionally interrupted by at least one heteroatom and having a total of from 1 to 20 carbon and/or heteroatoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from halogen radicals, preferably F or Cl, more preferably F; $CF_3$, CN and $SiMe_3$; more preferably hydrogen, a linear or branched alkyl radical, having from 1 to 4 carbon atoms, an unsubstituted aryl radical, having from 6 to 18 carbon atoms, an o-monosubstituted aryl radical having from 6 to 18 carbon atoms, an o,o'-disubstituted aryl radical, having from 6 to 18 carbon atoms, an unsubstituted heteroaryl radical, having a total of from 5 to 15 carbon atoms and/or heteroatoms, an o-monosubstituted heteroaryl radical, having a total of from 5 to 15 carbon atoms and/or heteroatoms, an o,o'-disubstituted heteroaryl radical, having a total of from 5 to 15 carbon atoms and/or heteroatoms, a group with donor or acceptor action, selected from the group consisting of F, $CF_3$, CN and $SiMe_3$; most preferably hydrogen, methyl, tert-butyl, $SiMe_3$, or an o,o'-dialkylated phenyl radical, preferably o,o'-dimethyl phenyl or o,o'-diisopropyl phenyl;
or
$R^4$ and $R^5$, $R^5$ and $R^6$ or $R^6$ and $R^7$ or $R^{4'}$ and $R^{5'}$, $R^{5'}$ and $R^{6'}$ or $R^{6'}$ and $R^{7'}$ form, independently of each other, with the carbon atoms to which they are bonded, a saturated, unsaturated or aromatic, optionally substituted ring, which is optionally interrupted by at least one heteroatom, has a total of from 5 to 18 carbon atoms and/or heteroatoms and may optionally be fused by at least one further optionally substituted saturated or unsaturated aromatic ring, optionally interrupted by at least one heteroatom and having a total of from 5 to 18 carbon atoms and/or heteroatoms.

According to the invention, the carbene ligands (I) and (I')

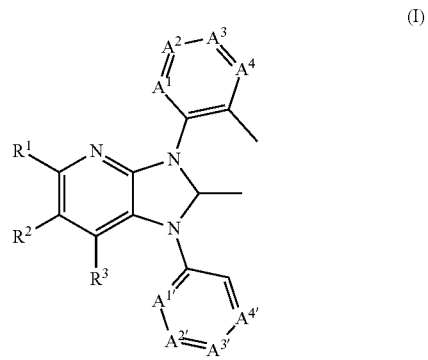

(I)

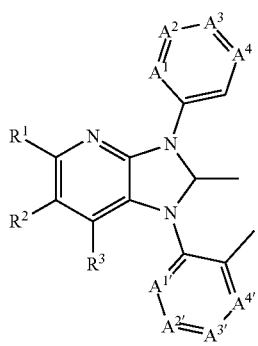

in the Ir metal-carbene complex are monoanionic bidentate ligands.

More preferably, the Ir metal-carbene complex has one of the following formulae (II), (II') or (II")

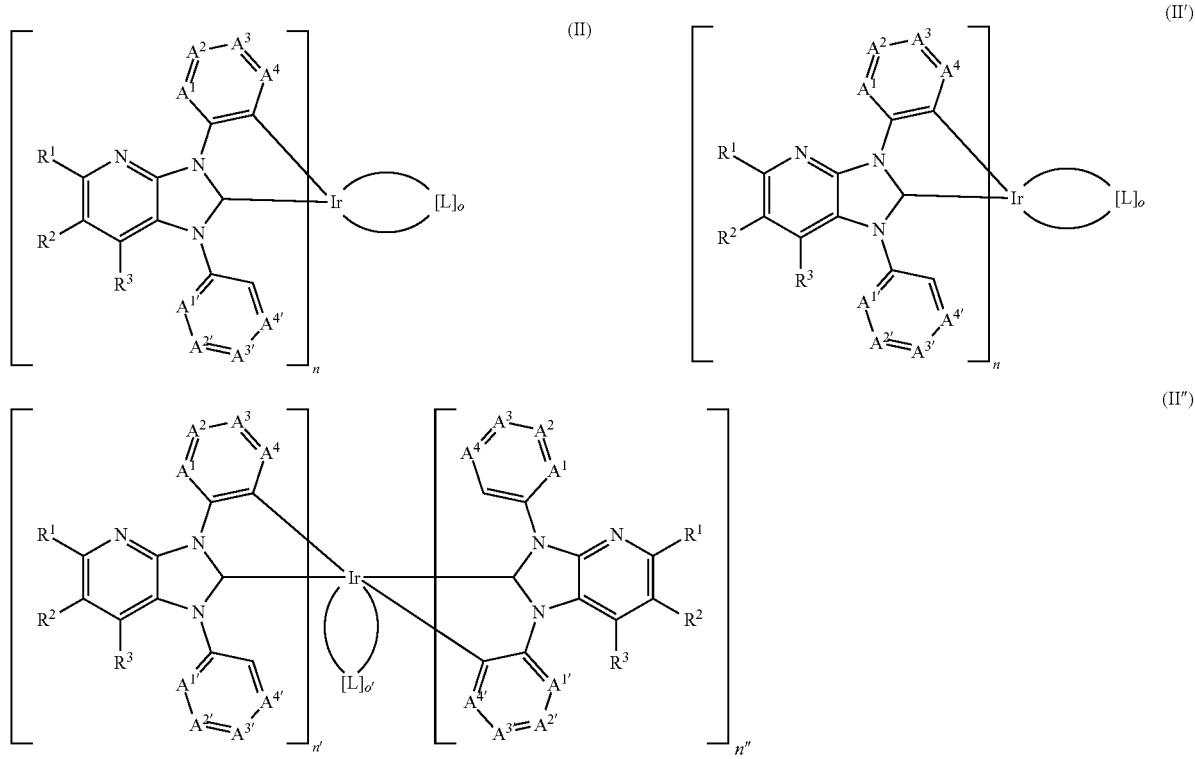

wherein
$R^1$, $R^2$ and $R^3$
are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably are each independently hydrogen, a linear or branched alkyl radical, having from 1 to 6 carbon atoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from the group consisting of halogen radicals, preferably F or Cl, more preferably F; $CF_3$, CN, $SiPh_3$ and $SiMe_3$; more preferably hydrogen, a linear or branched alkyl radical, having from 1 to 4 carbon atoms, an unsubstituted aryl radical, having from 6 to 18 carbon atoms (e.g. $C_6H_5$), an o-monosubstituted aryl radical having from 6 to 18 carbon atoms, an o,o'-disubstituted aryl radical having from 6 to 18 carbon atoms, an unsubstituted heteroaryl radical, having a total of from 5 to 15 carbon atoms and/or heteroatoms, an o-monosubstituted heteroaryl radical, having a total of from 5 to 15 carbon atoms and/or heteroatoms, an o,o'-disubstituted heteroaryl radical, having a total of from 5 to 15 carbon atoms and/or heteroatoms, a group with donor or acceptor action, selected from the group consisting of F, $CF_3$, $SiPh_3$ and $SiMe_3$; most preferably hydrogen, o-monoalkylated phenyl radical, o,o'-dialkylated phenyl radical, preferably o,o'-dimethyl phenyl or o,o'-diisopropyl phenyl;
or
$R^1$ and $R^2$ or $R^2$ and $R^3$ form, independently of each other, together with a carbon atom to which they are bonded an optionally substituted saturated or unsaturated or aromatic ring, optionally interrupted by at least one heteroatom and having a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;

A1 is $CR^4$ or N; preferably $CR^4$;
$A^2$ is $CR^5$ or N; preferably $CR^5$;
$A^3$ is $CR^6$ or N; preferably $CR^6$;
$A^4$ is $CR^7$ or N; preferably $CR^7$;
$A^{1'}$ is $CR^{4'}$ or N; preferably $CR^{4'}$;
$A^{2'}$ is $CR^{5'}$ or N; preferably $CR^{5'}$;
$A^{3'}$ is $CR^{6'}$ or N; preferably $CR^{6'}$;
$A^{4'}$ is $CR^{7'}$ or N; preferably $CR^{7'}$;
$R^4$, $R^5$, $R^6$, $R^7$, $R^{4'}$, $R^{5'}$, $R^{6'}$ and $R^{7'}$
are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having from 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably hydrogen, a linear or branched alkyl radical, optionally bearing at least one functional group, optionally interrupted by at least one heteroatom and having a total of from 1 to 20 carbon and/or heteroatoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from halogen radicals, preferably F or Cl, more preferably F; $CF_3$, CN and $SiMe_3$; more preferably hydrogen, a linear or branched alkyl radical, having from 1 to 4 carbon atoms, an unsubstituted aryl radical, having from 6 to 18 carbon atoms (e.g. $C_6H_5$), an o-monosubstituted aryl radical having from 6 to 18 carbon atoms, an o,o'-disubstituted aryl radical having from 6 to 18 carbon atoms, an unsubstituted heteroaryl radical, having a total of from 5 to 15 carbon atoms and/or heteroatoms, an o-monosubstituted heteroaryl radical, having a total of from 5 to 15 carbon atoms and/or heteroatoms, an o,o'-disubstituted heteroaryl radical, having a total of from 5 to 15 carbon atoms and/or heteroatoms, a group with donor or acceptor action, selected from the group consisting of F, $CF_3$, CN and $SiMe_3$; most preferably hydrogen, methyl, tert-butyl, $SiMe_3$ or an o,o'-dialkylated phenyl radical, preferably o,o'-dimethyl phenyl or o,o'-diisopropyl phenyl;
or
$R^4$ and $R^5$, $R^5$ and $R^6$ or $R^6$ and $R^7$ form, independently of each other, together with the carbon atoms to which they are bonded, a saturated or unsaturated aromatic, optionally substituted ring, which is optionally interrupted by at least one heteroatom, has a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;

n is 1, 2 or 3, preferably 3;
L is a monoanionic bidentate ligand,
o is 0, 1 or 2, where, when o=2, the L ligands may be the same or different, preferably 0;
n' is 1 or 2,
n" is 1 or 2,
wherein the sum of n'+n" is 2 or 3, preferably 3,
o' is 0 or 1, preferably 0;
wherein the sum of n+o in formulae (II) and (II') and the sum of n'+n"+ and o' in formula (II") is 3, with the proviso that n in formula (II) and (II') is at least 1 and n', as well as n" in formula (II") are at least 1.

The carbene ligands in the Ir metal-carbene complexes of formulae (II), (II') and (II") are monoanionic bidentate ligands The carbene ligands in the Ir metal-carbene complexes of formulae (II), (II') and (II") correspond to the carbene ligands of formulae (I) and (I') mentioned above.

A bidentate ligand is understood to mean a ligand coordinated at two sites to the transition metal atom M.

Preferred Ir metal-carbene complexes are Ir metal-carbene complexes of formulae (II) and (II").

Suitable monoanionic bidentate ligands L are, for example, ligands of the formula (B)

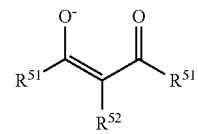

(B)

in which
$R^{51}$ is in each case independently a linear or branched alkyl radical having 1 to 6 carbons atoms, preferably methyl, ethyl, isopropyl, tert-butyl, $CF_3$; substituted or unsubstituted aryl radical having 6 to 20 carbon atoms, preferably unsubstituted phenyl or 2,6-dialkylphenyl; substituted or unsubstituted heteroaryl radical having a total of 5 to 18 carbon atoms and/or heteroatoms,
$R^{52}$ is hydrogen, a linear or branched alkyl radical having 1 to 6 carbon atoms, substituted or unsubstituted aryl radical having 6 to 20 carbon atoms, preferably hydrogen;
where the ligand of the formula (B) is, for example, acetylacetonato or hexafluoroacetylacetonato; picolinato, salicylato, 8-hydroxyquinolato ligands derived from Schiff bases, ligands derived from amino acids, heterocyclic noncarbene ligands, e.g. arylpyridines, e.g. phenylpyridine, and the further bidentate monoanionic ligands specified in WO 02/15645, carbene ligands of the general formula (VI) specified below, and also carbene ligands as specified in WO 2006/056418 and arylazoles, e.g. 2-arylimidazoles.

Preferably, L is a carbene ligand of the general formula (VI)

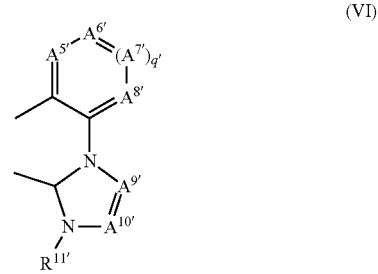

(VI)

where
A$^{9'}$ is CR$^{12'}$ or N;
A$^{10'}$ is CR$^{13'}$ or N;
R$^{11'}$ is a linear or branched alkyl radical optionally interrupted by at least one heteroatom, optionally bearing at least one functional group and having 1 to 20 carbon atoms, substituted or unsubstituted cycloalkyl radical, optionally bearing at least one functional group and having 3 to 20 carbon atoms, substituted or unsubstituted heterocycloalkyl radical interrupted by at least one heteroatom, optionally bearing at least one functional group and having 3 to 20 carbon atoms and/or heteroatoms, substituted or unsubstituted aryl radical, optionally bearing at least one functional group and having 6 to 30 carbon atoms, substituted or unsubstituted heteroaryl radical interrupted by at least one heteroatom, optionally bearing at least one functional group and having a total of 5 to 18 carbon atoms and/or heteroatoms,
R$^{12}$, R$^{13}$ are each independently hydrogen, a linear or branched alkyl radical optionally interrupted by at least one heteroatom, optionally bearing at least one functional group and having 1 to 20 carbon atoms, substituted or unsubstituted cycloalkyl radical, optionally bearing at least one functional group and having 3 to 20 carbon atoms, substituted or unsubstituted heterocycloalkyl radical interrupted by at least one heteroatom, optionally bearing at least one functional group and having 3 to 20 carbon atoms and/or heteroatoms, substituted or unsubstituted aryl radical, optionally bearing at least one functional group and having 6 to 30 carbon atoms, substituted or unsubstituted heteroaryl radical interrupted by at least one heteroatom, optionally bearing at least one functional group and having a total of 5 to 18 carbon atoms and/or heteroatoms, group with donor or acceptor action,
A$^{5'}$ is CR$^{14'}$ or N;
A$^{6'}$ is CR$^{15'}$ or N;
A$^{7'}$ is CR$^{16'}$ or N;
A$^{8'}$ is CR$^{17'}$ or N;
R$^{14'}$, R$^{15'}$, R$^{16'}$, R$^{17'}$ are each independently hydrogen, a linear or branched alkyl radical optionally interrupted by at least one heteroatom, optionally bearing at least one functional group and having 1 to 20 carbon atoms, substituted or unsubstituted cycloalkyl radical, optionally bearing at least one functional group and having 3 to 20 carbon atoms, substituted or unsubstituted heterocycloalkyl radical interrupted by at least one heteroatom, optionally bearing at least one functional group and having 3 to 20 carbon atoms and/or heteroatoms, substituted or unsubstituted aryl radical, optionally bearing at least one functional group and having 6 to 30 carbon atoms, substituted or unsubstituted heteroaryl radical interrupted by at least one heteroatom, optionally bearing at least one functional group and having a total of 5 to 18 carbon atoms and/or heteroatoms, group with donor or acceptor action,
or
R$^{14'}$ and R$^{15'}$, R$^{15'}$ and R$^{16'}$ or R$^{16'}$ and R$^{17'}$ form, together with the carbon atoms to which they are bonded, an unsaturated or aromatic, optionally substituted ring optionally interrupted by at least one heteroatom and having a total of 5 to 18 carbon atoms and/or heteroatoms,
and/or
R$^{12'}$ and R$^{13'}$ form, together with A$^{9'}$ and A$^{10'}$ to which they are bonded, an unsaturated or aromatic, optionally substituted ring optionally interrupted by exactly one heteroatom, preferably nitrogen, and having a total of 5 to 18 ring atoms,
and/or
if A$^{9'}$ is CR$^{12'}$, R$^{12'}$ and R$^{17'}$ together form a saturated or unsaturated, linear or branched bridge optionally comprising heteroatoms, aromatic units, heteroaromatic units and/or functional groups and having a total of 1 to 30 carbon atoms and/or heteroatoms, to which is optionally fused a substituted or unsubstituted, five- to eight-membered ring comprising carbon atoms and/or heteroatoms;
q is 0 or 1;
where—when o in formulae (II) or (II') is 2, the carbene ligands L of formulae (II) or (II') may be the same or different.

In a preferred embodiment, the metal-carbene complexes of formulae (II), (II') and (II") exclusively have carbene ligands.

Preferably, o in the metal-carbene complexes of the formulae (II) and (II') is 0 and o' in the metal-carbene complexes of the formula (II") is 0. In this case, n in formulae (II) and (II') is preferably 3 and n' and n" in formula (II") are 1 or 2, wherein the sum of n' and n" is 3.

The n azabenzimidazole carbene ligands may each be the same or different in the metal-carbene complexes of the general formulae (II), (II') and (II"). They are preferably the same. The metal-carbene complex of the general formula (II") preferably comprises three identical carbene ligands wherein the bonding situation in one of the carbene ligands is different from the bonding situation in the two further carbene ligands as shown in formula (II").

Preferred carbene complexes of the general formulae (II),)(II') and (II") are the following carbene complexes:

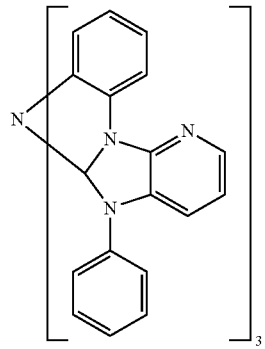

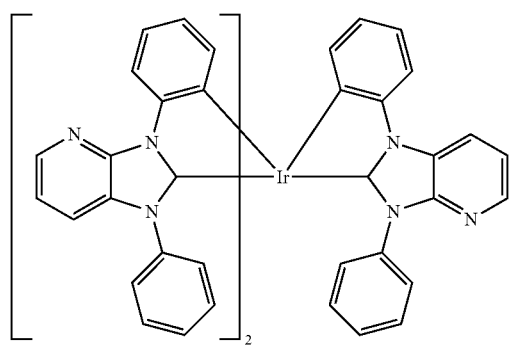

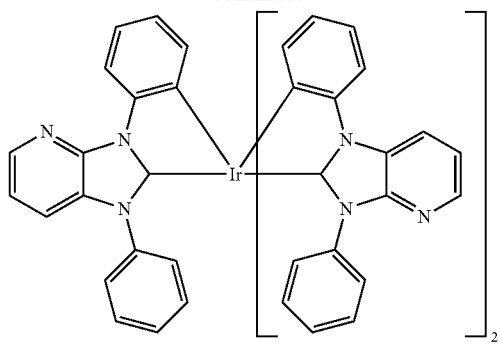
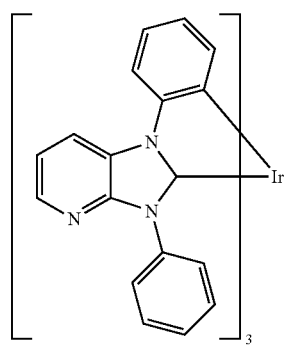
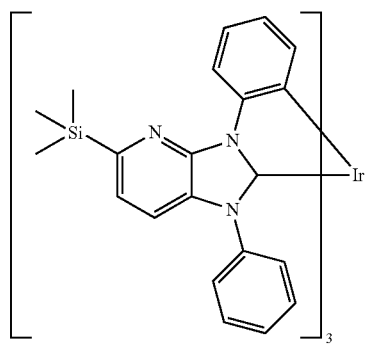
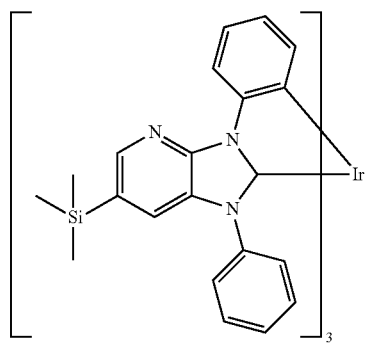
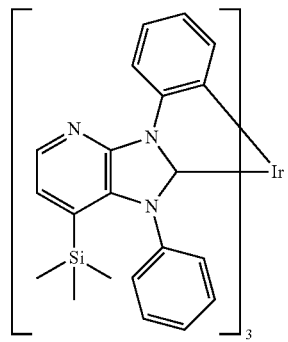
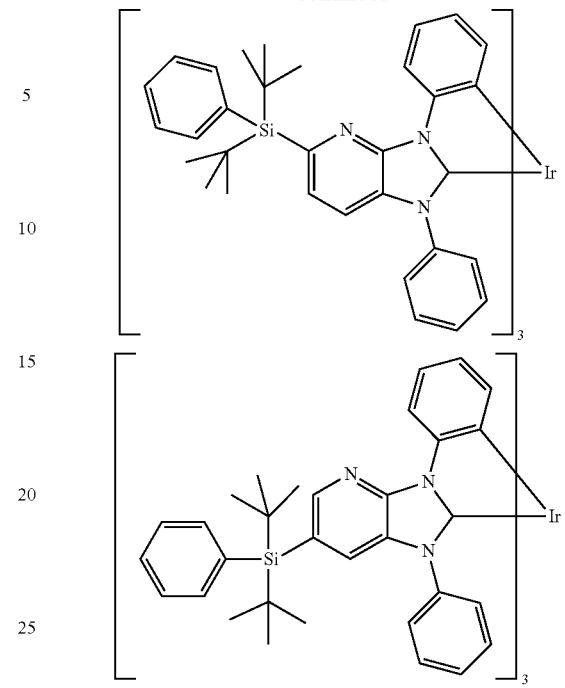
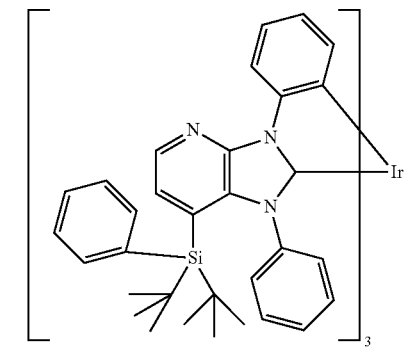
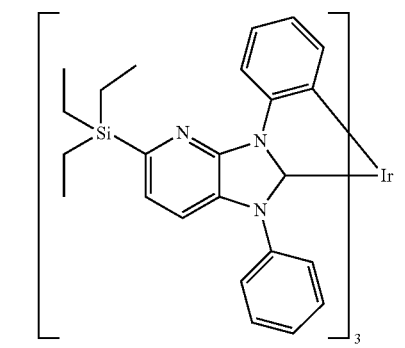
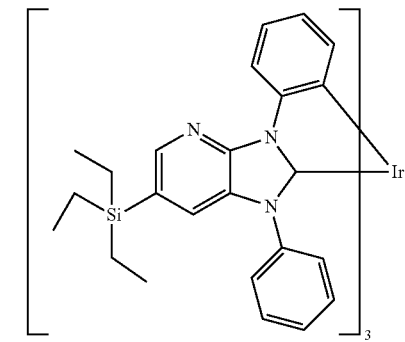

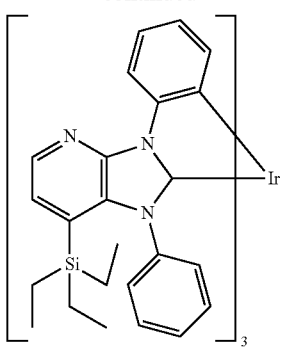
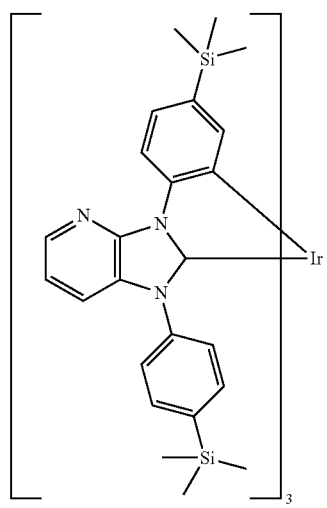
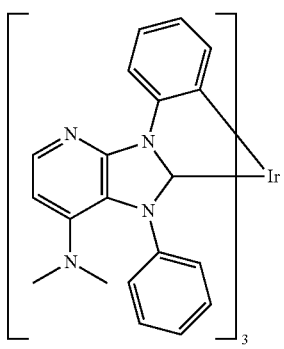
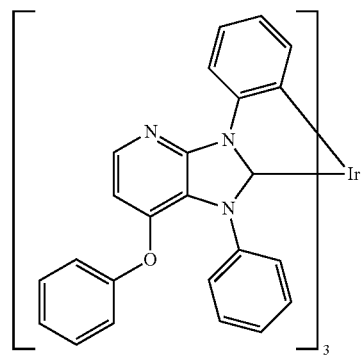
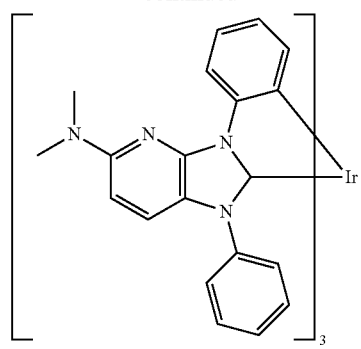
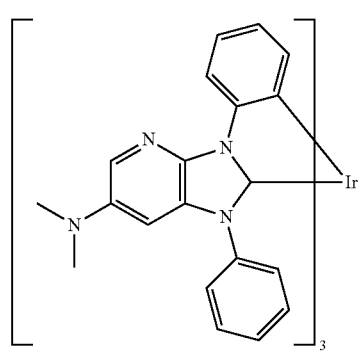
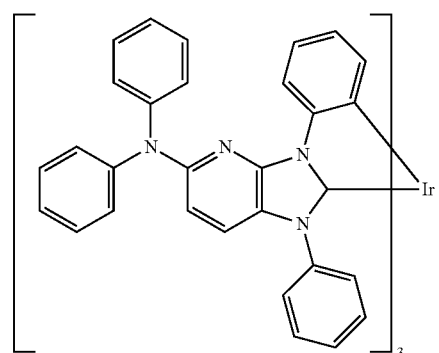
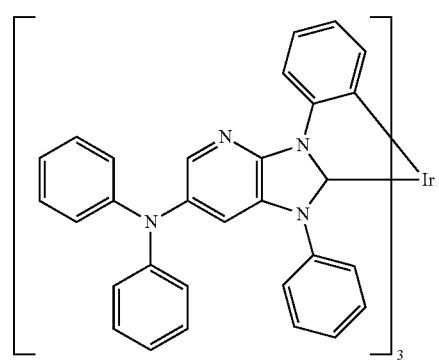

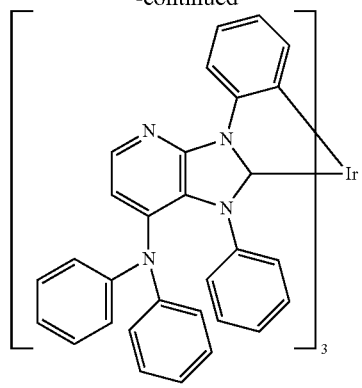
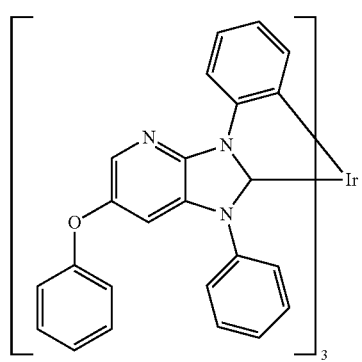
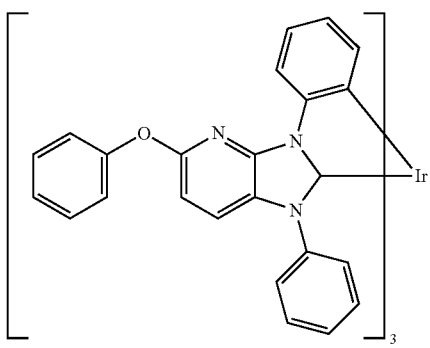
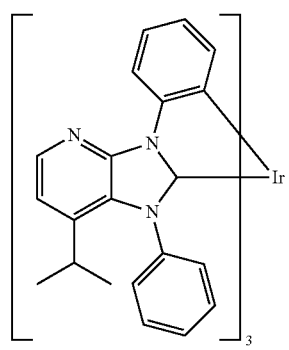
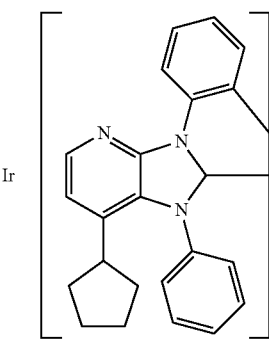
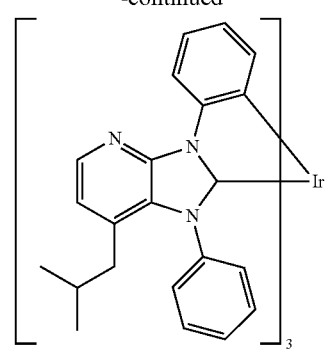
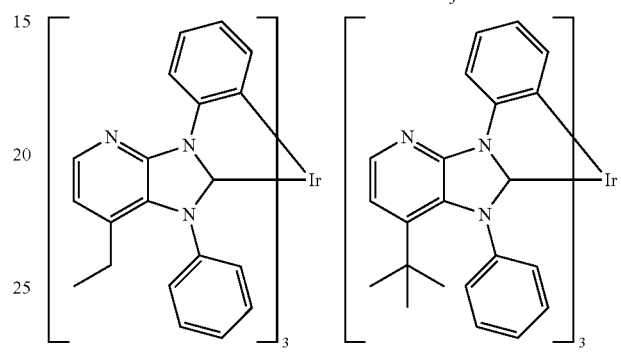
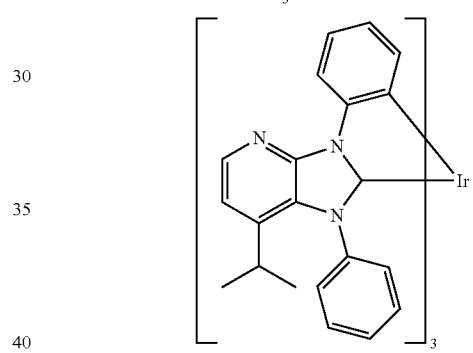
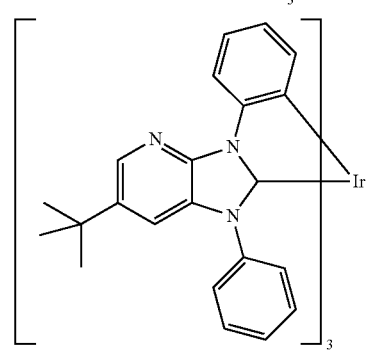
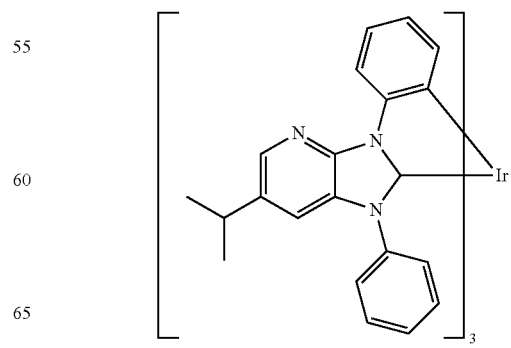

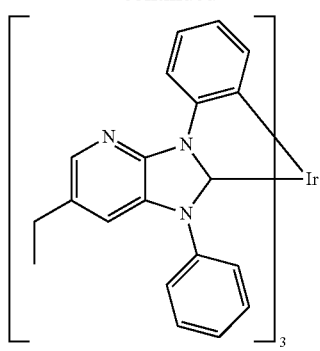
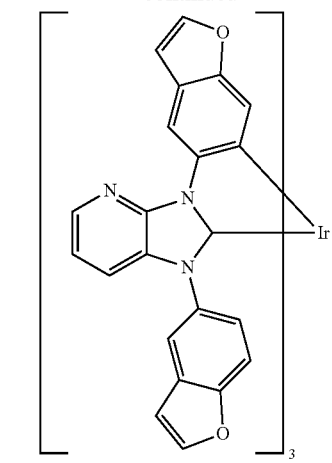
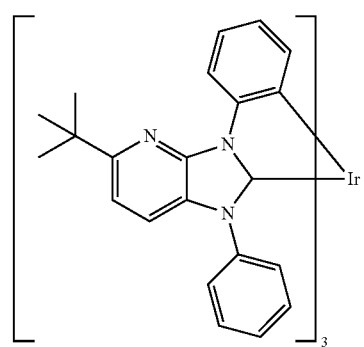
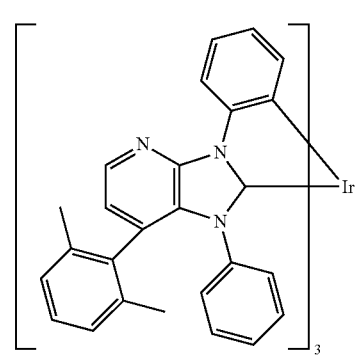
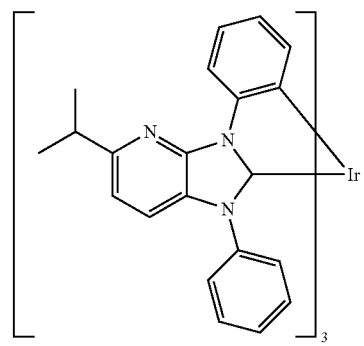
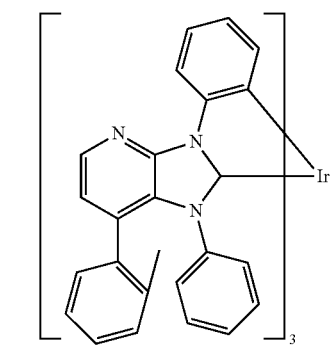
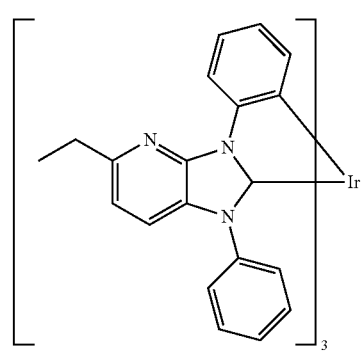
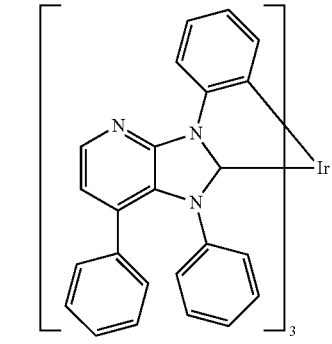

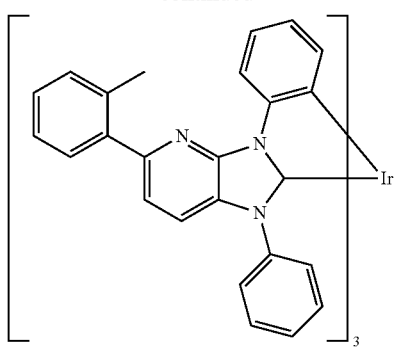
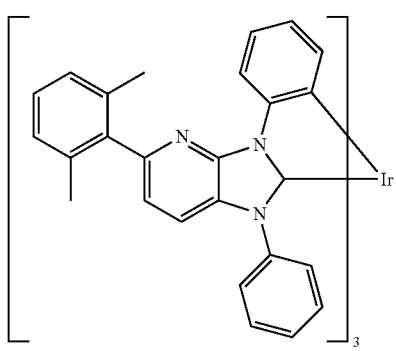
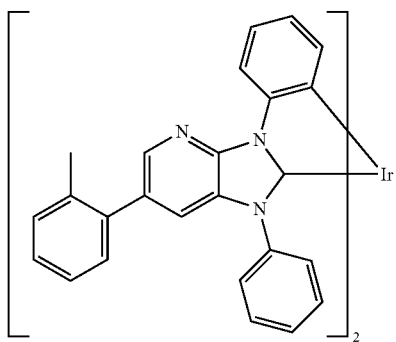
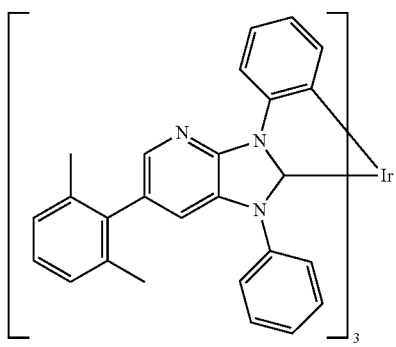
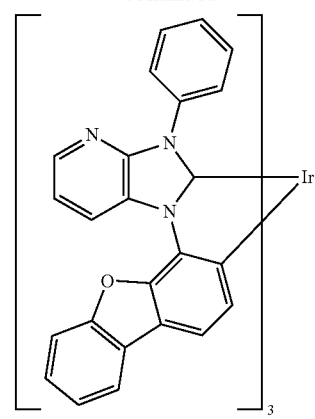
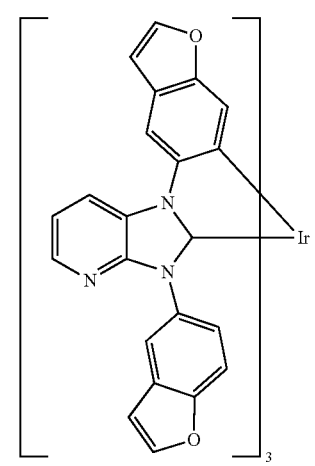
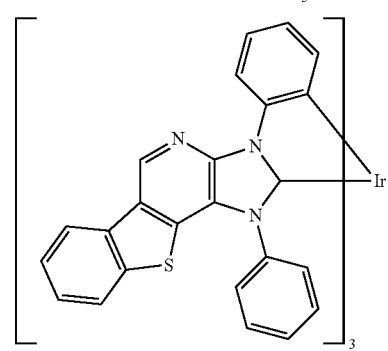
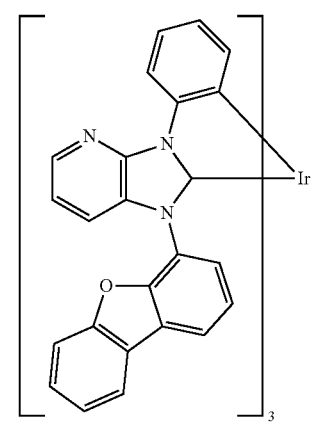

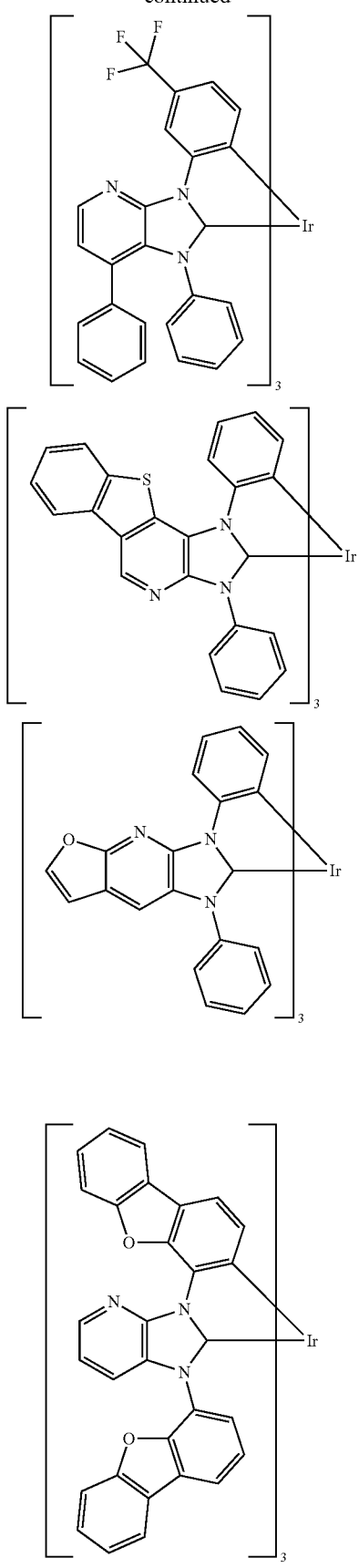
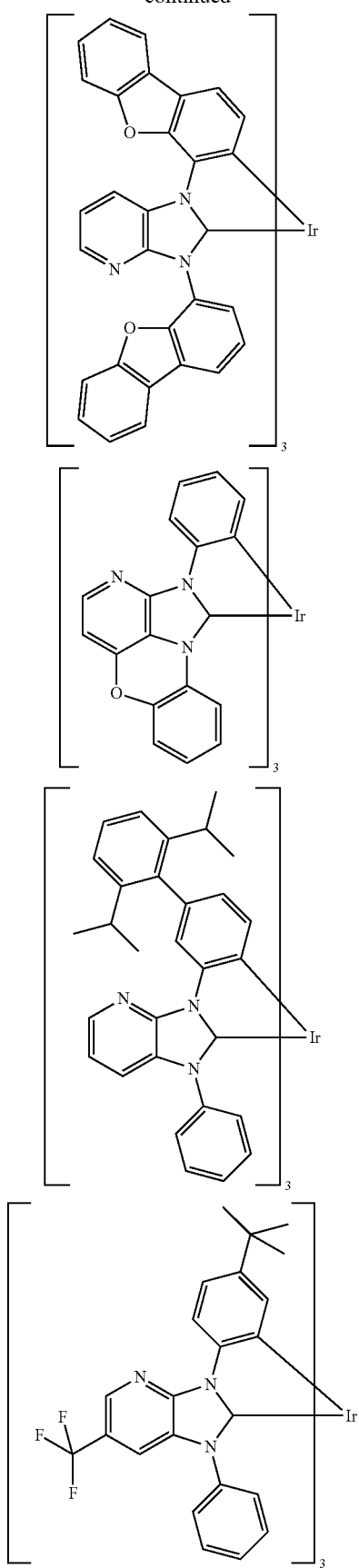

31
-continued
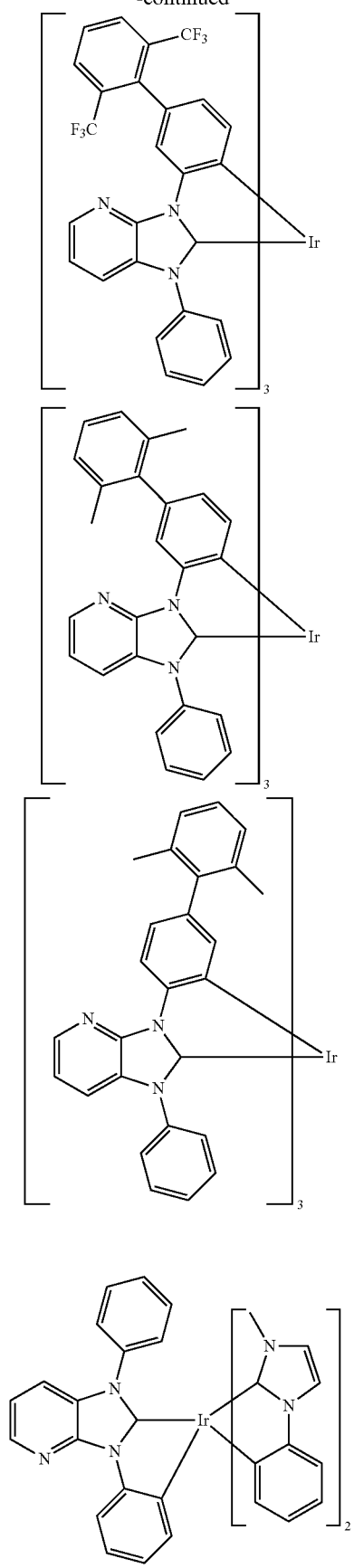
32
-continued
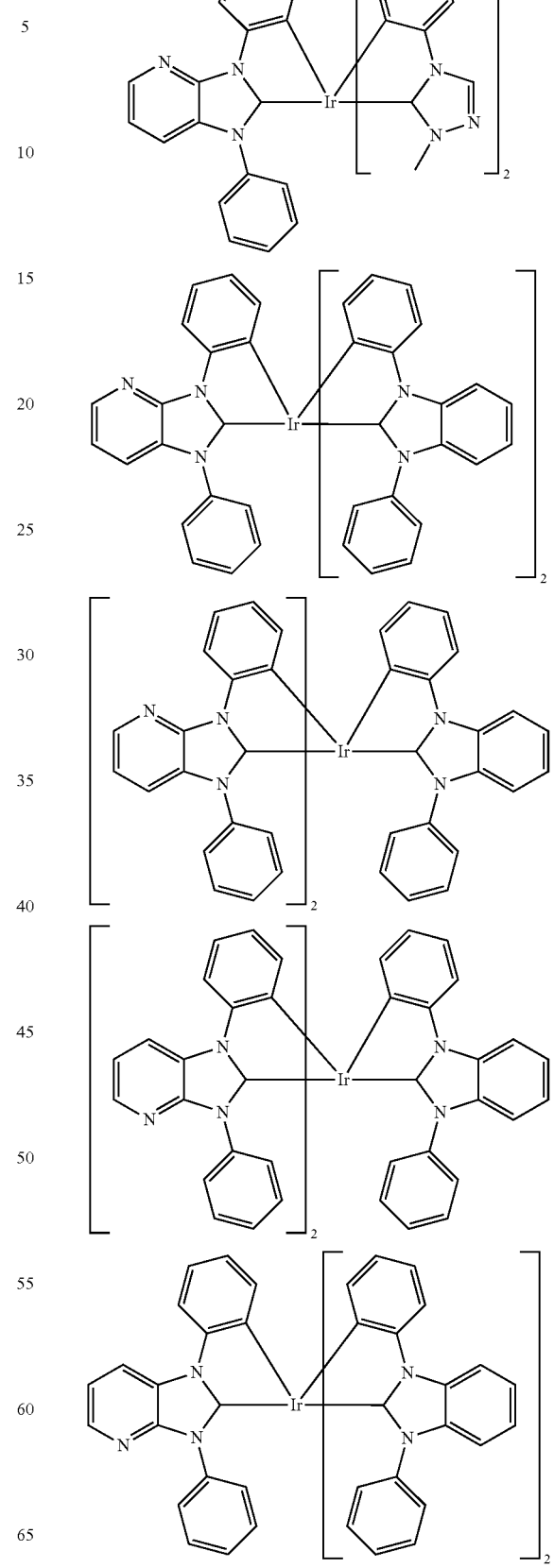

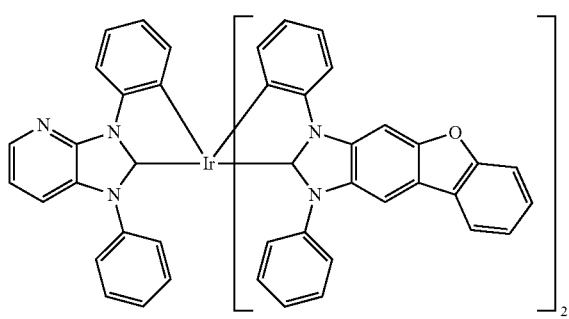
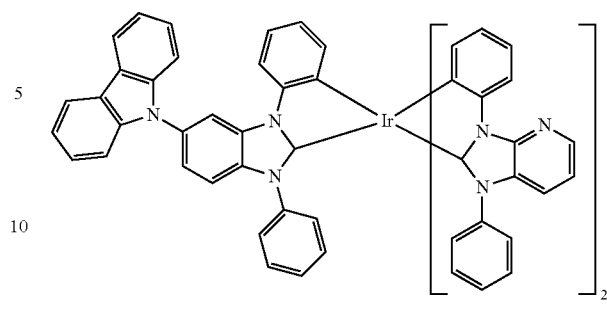
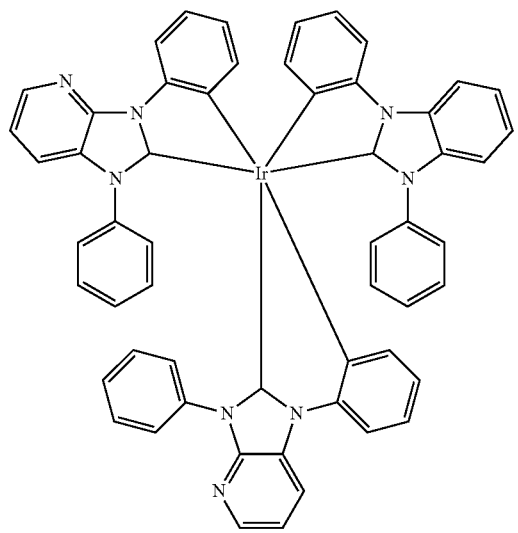
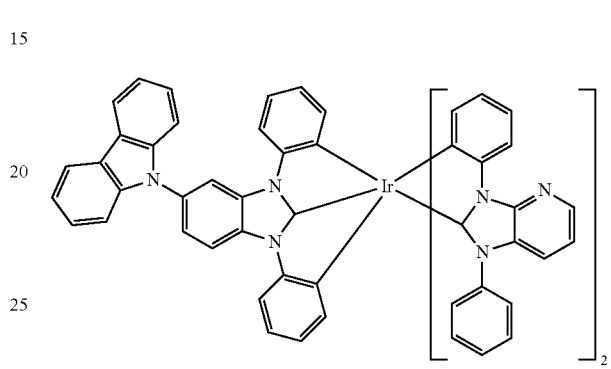
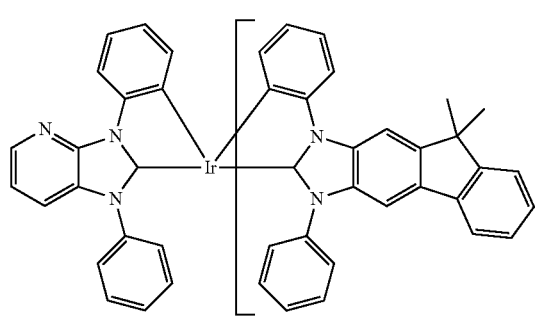
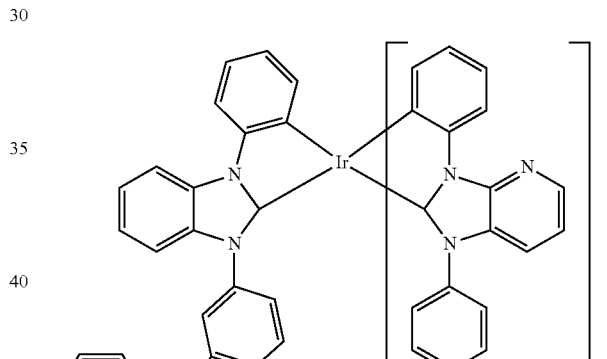
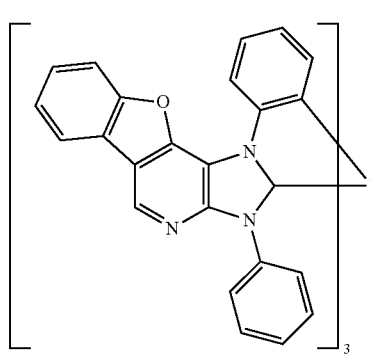
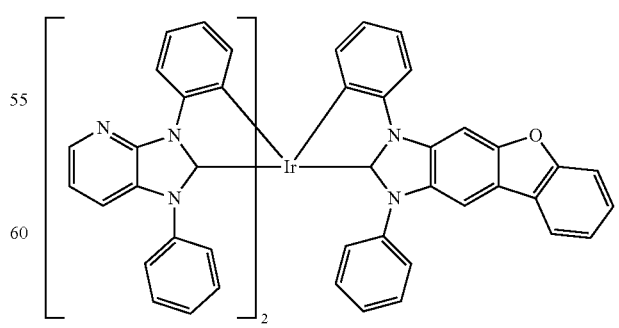
Most preferred carbene complexes are carbene complexes of formulae (IIa), (II'a), (II"a) and (II"a'):

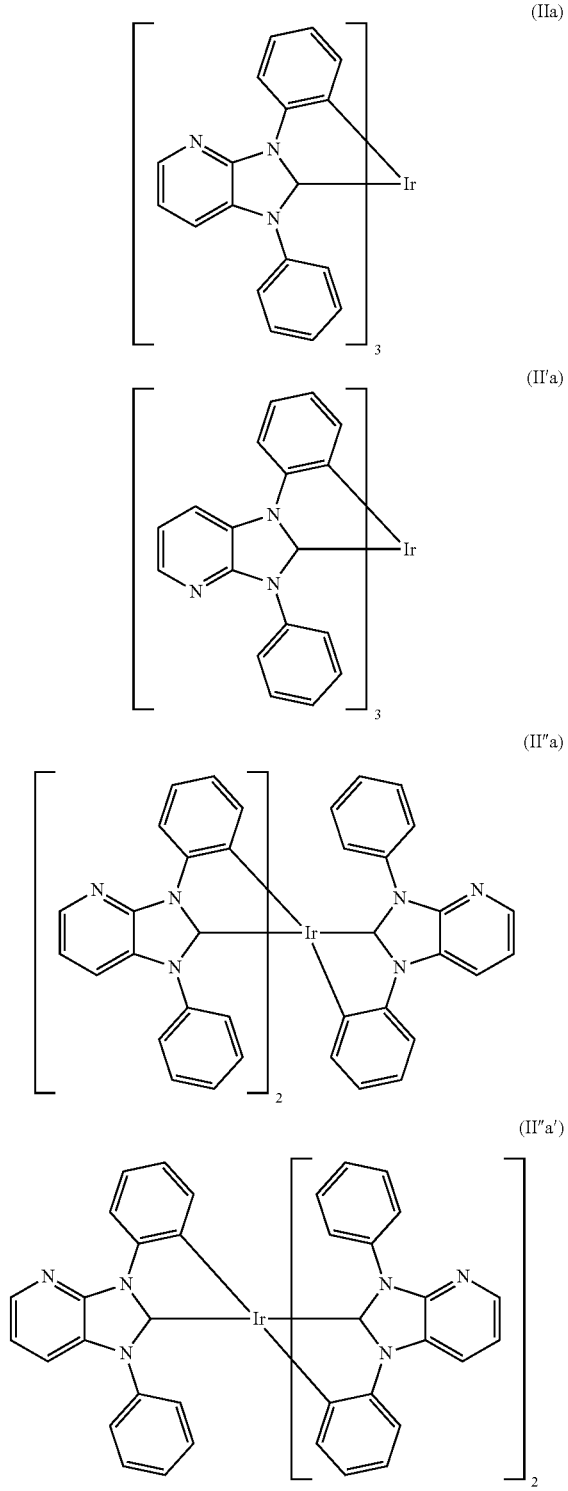

The Ir metal-carbene complex comprising one, two or three, preferably three, bidentate ligands of formula (I) and/or (I') are for example prepared by contacting suitable compounds comprising Ir with appropriate ligands or ligand precursors.

Preferably, a suitable compound comprising Ir and appropriate carbene ligands, preferably in deprotonated form as the free carbene or in the form of a protected carbene, for example as a silver-carbene complex, are contacted. Suitable precursor compounds comprise the substituents $R^1$ to $R^7$ and $R^{4'}$ to $R^{7'}$ which should be present in the Ir metal-carbene complex comprising one, two or three, preferably three, bidentate ligands of formula (I) and/or (I'). More preferably, the ligand precursor used is a corresponding Ag-carbene complex.

Suitable processes for preparing the Ir metal-carbene complex comprising one, two or three, preferably three, bidentate ligands of formula (I) and/or (I') are for example mentioned in WO 2012/172482 A1.

The resulting complexes may yield different isomers that can be separated or converted into a form with a major isomer by isomerization of the mixture.

Ir Metal-Carbene Complex Comprising One, Two or Three, Preferably Three, Bidentate Ligands of Formula (I) and/or (I') as Hole-Transport Material and/or Electron/Exciton Blocker Material; Hole-Transport Layer; Electron/Exciton Blocking Layer According to the present invention, the Ir metal-carbene complex comprising one, two or three, preferably three, bidentate ligands of formula (I) and/or (I') is employed as hole-transport material and/or electron/exciton blocker material, preferably as electron/exciton blocker material or as hole-transport material and electron/exciton blocker material in the organic electronic device, preferably the OLED. Preferably, the at least one hole-transport material comprising the Ir metal-carbene complex comprising one, two or three, preferably three, bidentate ligands of formula (I) and/or (I') is present in an hole transport layer of the organic electronic device, preferably the OLED, and/or the at least one electron/exciton blocker material, comprising the Ir metal-carbene complex comprising one, two or three, preferably three, bidentate ligands of formula (I) and/or (I') is present in an electron-blocking layer of the organic electronic device, preferably the OLED.

In one embodiment according to the present invention, the Ir metal-carbene complex comprising one, two or three, preferably three, bidentate ligands of formula (I) and/or (I') is employed as hole-transport material, preferably in the hole-transport layer, in the organic electronic device, preferably the OLED, according to the present invention.

In a further more preferred embodiment according to the present invention, the Ir metal-carbene complex comprising one, two or three, preferably three, bidentate ligands of formula (I) and/or (I') is employed as electron/exciton blocker material, preferably in the electron/exciton blocking layer, in the organic electronic device, preferably the OLED, according to the present invention.

In a further embodiment according to the present invention, which is preferred, the Ir metal-carbene complex comprising one, two or three, preferably three, bidentate ligands of formula (I) and/or (I') is employed as hole-transport material, preferably in the hole-transport layer, and as electron/exciton blocker material, preferably in the electron/exciton blocking layer, in the organic electronic device, preferably the OLED, according to the present invention.

The Ir metal-carbene complex comprising one, two or three, preferably three, bidentate ligands of formula (I) and/or (I') may be employed alone or in a mixture, for example together with another hole-transport material and/or a doping material in order to improve the transport properties—in the case that the Ir metal-carbene complex is used as hole-transport material—or with another electron/exciton blocker material—in the case that the Ir metal-carbene complex is used as electron/exciton blocker material. Suitable doping materials for the hole-transport material are mentioned below.

Preferably, the Ir metal-carbene complex is employed alone (without further components), in the case that the Ir metal-carbene complex is used as electron/exciton blocker material. In a preferred embodiment of the present invention, the electron-blocking layer of the organic electronic device, preferably the OLED, according to the present invention is consisting of the Ir metal-carbene complex comprising one, two or three, preferably three, bidentate ligands of formula (I) and/or (I').

Preferably, the Ir metal-carbene complex is employed together with at least one doping material or alone (without further components), more preferably together with one doping material, in the case that the Ir metal-carbene complex is used as hole-transport material. In a preferred embodiment of the present invention, the hole-transport layer of the organic electronic device, preferably the OLED, according to the present invention is consisting of the Ir metal-carbene complex comprising one, two or three, preferably three, bidentate ligands of formula (I) and/or (I') and one or two, preferably one, doping material(s).

Suitable doping materials for the hole-transport layer are electronical doping materials in order to improve the transport properties of the hole-transport material used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport material with at least one metal oxide, for example $MoO_2$, $MoO_3$, $WO_x$, $ReO_3$ and/or $V_2O_5$, preferably $MoO_3$ and/or $ReO_3$, more preferably $MoO_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-tetracyanoquinodimethane, dicyanomethylene-1,3,4,5,7,8-hexafluoro-6Hnaphthalen-2-ylidene)malononitrile ($F_6$-TNAP), $Mo(tfd)_3$ (from Kahn et al., J. Am. Chem. Soc. 2009, 131 (35), 12530-12531), compounds as described in EP 1 988 587, US 2008265216, EP 2 180 029, US 20100102709, WO 2010/132236, EP 2 180 029 and quinone compounds as mentioned in EP2401254.

The present invention therefore preferably relates to the organic electronic device, preferably the IDLED, according to the present invention, wherein the Ir metal-carbene complex comprising one, two or three, preferably three, bidentate ligands of formula (I) and/or (I'), is employed in combination with at least one doping material, preferably at least one metal oxide, more preferably at least one metal oxide selected from $MoO_3$, $ReO_3$, $MoO_2$, $WO_x$ and $V_2O_5$, most preferably selected from $MoO_3$ and $ReO_3$, in the case that the Ir metal-carbene complex is used as hole-transport material, preferably in the hole-transport layer.

The combination of the Ir metal-carbene complex comprising one, two or three, preferably three, bidentate ligands of formula (I) and/or (I') and the doping material, preferably the at least one metal oxide, more preferably at least one metal oxide selected from $MoO_3$, $ReO_3$, $MoO_2$, $WO_x$ and $V_2O_5$, most preferably selected from $MoO_3$ and $ReO_3$, preferably comprises 50 to 90% by weight, of the Ir metal-carbene complex comprising one, two or three, preferably three, bidentate ligands of formula (I) and/or (I') and 10 to 50% by weight of the doping material, preferably the at least one metal oxide, more preferably at least one metal oxide selected from $MoO_3$, $ReO_3$, $MoO_2$, $WO_x$ and $V_2O_5$, most preferably selected from $MoO_3$ and $ReO_3$, wherein the sum of the amount of the Ir metal-carbene complex comprising one, two or three, preferably three, bidentate ligands of formula (I) and/or (I') and the doping material is 100% by weight.

The present invention further relates to a hole-transport layer or an electron/exciton blocking layer, comprising at least one Ir metal-carbene complex, comprising one, two or three bidentate ligands of formula (I) and/or (I') as defined in the present application. Preferred Ir metal-carbene complexes are defined in the present application.

The hole-transport layer preferably comprises in addition to the Ir metal-carbene complex comprising one, two or three, preferably three, bidentate ligands of formula (I) and/or (I') at least one doping material. Suitable and preferred doping materials are mentioned before. More preferably, the hole-transport layer comprises 50 to 90% by weight, of the Ir metal-carbene complex comprising one, two or three, preferably three, bidentate ligands of formula (I) and/or (I') and 10 to 50% by weight of the doping material, preferably the at least one metal oxide, more preferably at least one metal oxide selected from $MoO_3$, $ReO_3$, $MoO_2$, $WO_x$ and $V_2O_5$, most preferably selected from $MoO_3$ and $ReO_3$, wherein the sum of the amount of the Ir metal-carbene complex comprising one, two or three, preferably three, bidentate ligands of formula (I) and/or (I') and the doping material is 100% by weight.

The electron/exciton blocking layer is preferably consisting of the Ir metal-carbene complex, comprising one, two or three, preferably three, bidentate ligands of formula (I) and/or (I').

The layer thickness of the hole-transport layer is preferably 5 to 100 nm, more preferably 10 to 80 nm.

The layer thickness of the electron/exciton blocking layer is preferably 1 to 50 nm, more preferably 5 to 10 nm.

Device Structure—OLED Structure

Suitable structures of the organic electronic devices are known to those skilled in the art. Preferred organic electronic devices are selected from organic light-emitting diodes (OLED), light-emitting electrochemical cells (LEEC), organic photovoltaic cells (OPV) and organic field-effect transistors (OFET). More preferred organic electronic devices are OLEDs.

The device structures of said OLEDs, LEECs, OPVs and OFETs have been described above in general terms. In the following, the device structures of preferred OLEDs (which are preferred electronic devices according to the present invention) are described.

As mentioned above, the present invention preferably relates to an organic electronic device which is an OLED, wherein the OLED comprises
(a) an anode,
(b) a cathode,
(c) a light-emitting layer between the anode and the cathode,
(d) at least one layer, selected from a hole-transport layer (d1) and an electron/exciton blocking layer (d2),
wherein the at least one hole-transport material, comprising the Ir metal-carbene complex comprising one, two or three bidentate ligands of formula (I) and/or (I') is present in the hole-transport layer of the OLED and/or the at least one electron/exciton blocker material, comprising the Ir metal-carbene complex comprising one, two or three, preferably three, bidentate ligands of formula (I) and/or (I') is present in the electron/exciton blocking layer of the OLED.

Preferred Ir metal-carbene complexes comprising one, two or three, preferably three, bidentate ligands of formula (I) and/or (I'), preferred hole-transport materials, preferred electron/exciton blocker materials, preferred hole-transport layers (d1) and preferred electron/exciton blocking layers (d2) are mentioned before.

The layer sequence in the inventive OLED is preferably as follows:
1. anode (a)
2. hole-transport layer (d1)
3. electron/exciton blocking layer (d2)
4. light-emitting layer (c)
5. cathode (b)

Layer sequences different from the aforementioned construction are also possible, and are known to those skilled in the art. For example, it is possible that the OLED does not have all of the layers mentioned; for example, an OLED with the layers (a) (anode), (c) (light-emitting layer) and (b) (cathode) and layer (d1) (hole-transort layer) or layer (d2) (electron/exciton blocking layer) are likewise suitable.

The OLEDs may additionally have a blocking layer for holes/excitons (e) adjacent to the cathode side of the light-emitting layer (c) and/or an electron transport layer (f) adjacent to the cathode side of the blocking layer for holes/excitons (e), if present, respectively adjacent to the cathode side of the light-emitting layer (c), if the blocking layer for holes/excitons (e) is not present.

The present invention therefore more preferably relates to an inventive OLED having the following layer sequence:
1. anode (a)
2. hole-transport layer (d1)
3. electron/exciton blocking layer (d2)
4. light-emitting layer (c)
5. blocking layer for holes/excitons (e)
6. electron transport layer (f)
7. cathode (b)

In a further embodiment, the inventive OLED, in addition to layers (a), (b), (c), (d1), (d2), (e) and (f), comprises at least one of the further layers mentioned below:
A hole injection layer (g) between the anode (a) and the hole-transport layer (d1);
an electron injection layer (h) between the electron-transport layer (f) and the cathode (b).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron transport layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole-transport layer should be matched to the work function of the anode, and the LUMO (lowest unoccupied molecular orbital) of the electron conductor layer should be matched to the work function of the cathode, provided that the aforementioned layers are present in the inventive OLEDs.

Hole-Transport Layer (d1), Electron Exciton Blocking Layer (d2)

In the case that the OLED comprises a material different from the materials mentioned before in the hole-transport layer or in the electron/exciton blocking layer, suitable materials are mentioned below.

However, it is preferred that the Ir metal-carbene complex comprising one, two or three, preferably three, bidentate ligands of formula (I) and/or (I') is either present in the electron/exciton blocking layer (d2) or present in the hole-transport layer (d1) and in the electron/exciton blocking layer (d2). Preferred embodiments for the hole-transport layer and in the electron/exciton blocking layer are mentioned above. In a further preferred embodiment, the Ir metal-carbene complex comprising one, two or three, preferably three, bidentate ligands of formula (I) and/or (I') is present in the hole-transport layer (d1) and/or in the electron/exciton blocking layer (d2) and additionally in the light-emitting layer as co-host.

Hole-Transport Layer (d1)

In the case that the Ir metal-carbene complex comprising one, two or three, preferably three, bidentate ligands of formula (I) and/or (I') is present in the electron/exciton blocking layer (d2), the hole transport layer may comprise a hole-transport material different from the Ir metal-carbene complex comprising one, two or three, preferably three, bidentate ligands of formula (I) and/or (I').

Suitable hole-transport materials for layer (d1) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transport material. Customarily used hole-transporting molecules are selected from the group consisting of

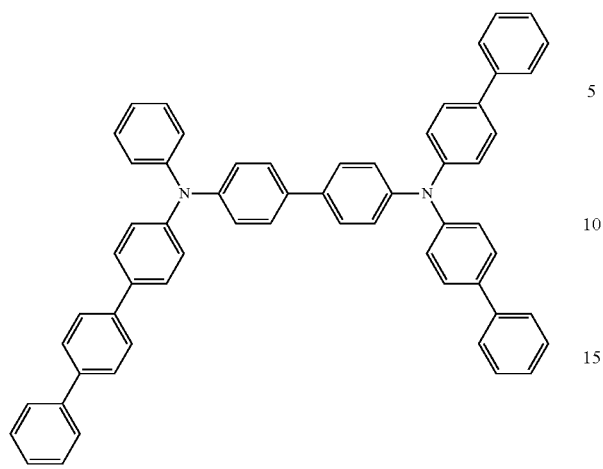

(4-phenyl-N-(4-phenylphenyl)-N-[4-[4-(N-[4-(4-phenyl-phenyl)phenyl]anilino)phenyl]phenyl]aniline),

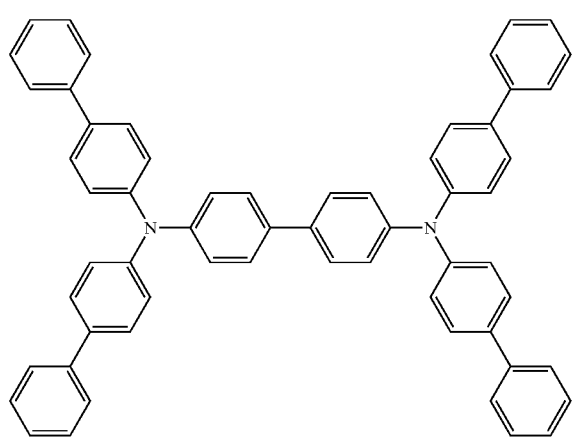 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

phenyl-N-(4-phenylphenyl)-N-[4-[4-(4-phenyl-N-(4-phenylphenyl)anilino)phenyl]phenyl]aniline),

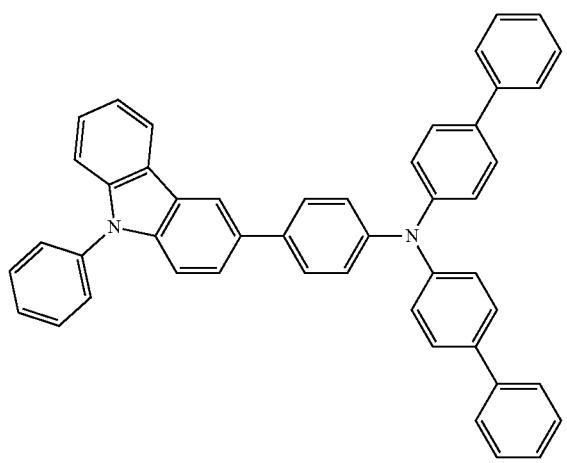 [SMILES: c1ccc(-c2ccc(N(c3ccc(-c4ccccc4)cc3)c3ccc(-c4ccc5c(c4)c4ccccc4n5-c4ccccc4)cc3)cc2)cc1]

(4-phenyl-N-[4-(9-phenylcarbazol-3-yl)phenyl]-N-(4-phenylphenyl)aniline),

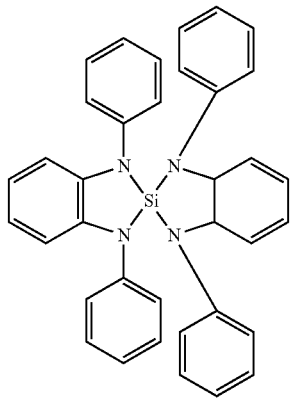 [SMILES: C1=CC2C(C=C1)N(c1ccccc1)[Si]1(N(c3ccccc3)c3ccccc3N1c1ccccc1)N2c1ccccc1]

1,1',3,3'-tetraphenylspiro[1,3,2-benzodiazasilole-2,2'-3a,7a-dihydro-1,3,2-benzodiazasilole],

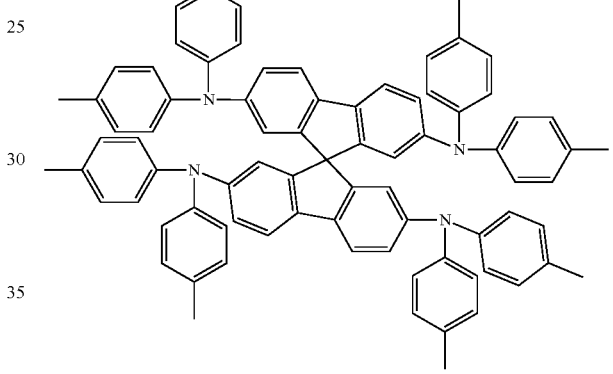

(N2,N2,N2',N2',N7,N7,N7',N7'-octakis(p-tolyl)-9,9'-spirobi [fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis [(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p (diethylamino)styryl]5-[p-(diethylamino)phenyl]pyrazoline (PPR or DEASP), 1,2-trans-bis(9H-carbazol 9-yl)-cyclobutane (DCZB), N,N,N',N'-tetrakis(4-methylphenyl)-(1,1'-biphenyl)-4,4'-diamine (TTB), fluorine compounds such as 2,2',7,7-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bisbiphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(-styrenesulfonate) also called PEDOT/PSS.

The hole-transport materials mentioned above are commercially available and/or prepared by processes known by a person skilled in the art.

In a preferred embodiment it is possible to use specific metal carbene complexes as hole-transport materials. Suitable carbene complexes are, for example, carbene complexes as described in WO2005/019373A2, WO2006/056418 A2, WO2005/113704, WO2007/115970, WO2007/115981 and WO2008/000727. One example of a suitable carbene complex is Ir(DPBIC)$_3$ with the formula:

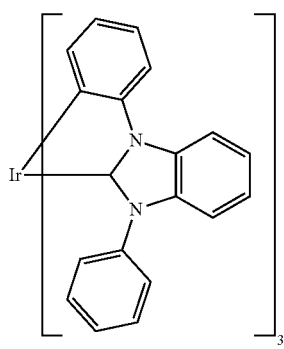

The preparation of Ir(DPBIC)$_3$ is for example mentioned in WO 2005/019373 A2.

The hole-transport layer may also be electronically doped in order to improve the transport properties of the materials used. Suitable doping materials are mentioned above. Preferably, the hole-transport layer comprises 50 to 90% by weight, of the hole-transport material and 10 to 50% by weight of the doping material, wherein the sum of the amount of the hole-transport material and the doping material is 100% by weight.

Electron/Exciton Blocking Layer (d2)

In the case that the Ir metal-carbene complex comprising one, two or three, preferably three, bidentate ligands of formula (I) and/or (I') is present in the hole-transport layer (d1), the electron/exciton blocking layer may comprise an electron/exciton material different from the Ir metal-carbene complex comprising one, two or three, preferably three, bidentate ligands of formula (I) and/or (I').

Blocking layers may also be used to block excitons from diffusing out of the emissive layer. Suitable metal complexes for use as electron/exciton blocker material are, for example, carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application. One example of a suitable carbene complex is Ir(DPBIC)$_3$ with the formula:

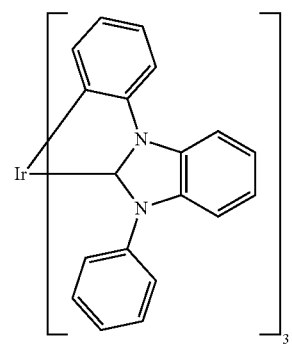

Light-Emitting Layer (a)
Emitter Material

The light-emitting layer (c) comprises at least one emitter material. Preferably, the light-emitting layer comprises at least one emitter material, which has an emission maximum (•) of from 400 to 500 nm. Preferably, the emitter has an emission maximum ($\lambda$), which of from 425 nm to 490 nm, more preferably of from 440 nm to 475 nm, preferably with a FWHM (full width at half maximum) of from 1 nm to 140 nm, more preferably of from 30 nm to 120 nm, most preferably of from 50 nm to 100 nm.

This may in principle be a fluorescence or phosphorescence emitter, suitable emitter materials being known to those skilled in the art. Preferably, the light-emitting layer comprises at least one phosphorescent emitter material.

In the context of the present invention, a phosphorescence emitter is an emitter showing emission of light by phosphorescence. However, this does not exclude that the phosphorescence emitter additionally shows emission of light by fluorescence.

The triplet decay time (intensity reduced to $1/e=0.367879441$ times its initial value) of the phosphorescence emission of the phosphorescence emitter is preferably of from 0.5 to 100 micro seconds, more preferably of from 0.5 to 10 micro seconds, most preferably of from 0.5 to 3 micro seconds.

The phosphosphorescence emitter show phosphorescence emission from triplet excited states, preferably at the operating temperatures of the OLED. Phosphorescence may be preceded by a transition from a triplet excited state to an intermediate non-triplet state from which the emissive decay occurs.

The phosphorescence emitter compounds used with preference are based on metal complexes, and especially the complexes of the metals Ru, Rh, Ir, Pd and Pt, in particular the complexes of Ir, have gained significance.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO 2010/086089, WO 2012/121936 A2, US 2011/0057559, WO 2011/106344, US 2011/0233528 and WO 2011/157339.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)(pyridinato-N,C$^{3'}$)(acetylacetonate), tris(2-phenylquinoline)iridium(III), iridium(III) bis(2-(4,6-difluorophenyl)pyridinato-N,C$^2$)picolinate, iridium(III) bis(1-phenylisoquinoline)(acetylacetonate), bis(2-phenylquinoline)(acetylacetonato)iridium(III), iridium(III) bis(dibenzo[f,h]quinoxaline)-(acetylacetonate), bis(2-methyldibenzo[f,h]quinoxaline)(acetylacetonate), bis[1-(9,9-dimethyl-9H-fluoren-2-yl)isoquinoline](acetylacetonato)iridium(III), bis(2-phenylbenzo-thiazolato)(acetylacetonato)iridium(III), bis(2-(9,9-dihexylfluorenyl)-1-pyridine)(acetyl-acetonato)iridium(III), bis(2-benzo[b]thiophen-2-ylpyridine)(acetylacetonato)iridium(III).

Preferred phosphorescence emitters are carbene complexes. Carbene complexes which are suitable phosphorescent blue emitters are specified in the following publications: WO 2006/056418 A2, WO 2005/113704, WO 2007/115970, WO 2007/115981, WO 2008/000727, WO2009050281, WO2009050290, WO2011051404, US2011/057559 WO2011/073149, WO2012/121936A2, US2012/0305894A1, WO2012170571, WO2012170461, WO 2012170463, WO2006121811, WO2007095118, WO2008156879, WO2008156879, WO2010068876, US20110057559, WO2011106344, US20110233528, WO2012048266 and WO2012172482.

Preferably, the light-emitting layer in the OLED of the present invention comprises at least one carbene complex as phosphorescence emitter. Suitable carbene complexes are, for example, carbene complexes of the general formula (III)

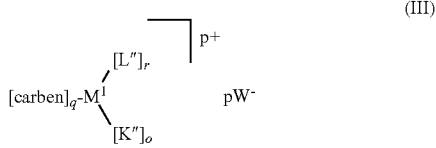

(III)

in which the symbols are each defined as follows:
M$^1$ is a metal atom selected from the group consisting of metals of group IB, IIB, IIIB, IVB, VB, VIB, VIIB, the lanthanides and IIIA of the Periodic Table of the Elements (CAS version) in any oxidation state possible for the particular metal atom;
carbene is a carbene ligand which may be uncharged or monoanionic and mono-, bi- or tridentate; the carbene ligand may also be a bis- or triscarbene ligand;
L" is a mono- or dianionic ligand, preferably monoanionic ligand, which may be mono- or bidentate;
K" is an uncharged mono- or bidentate ligand;
q is the number of carbene ligands, where n is at least 1 and the carbene ligands in the complex of the formula I when q>1 may be the same or different;
r is the number of ligands L", where m may be 0 or ≥1, and the ligands L" when r>1 may be the same or different;
o''' is the number of ligands K", where o''' may be 0 or ≥1, and the ligands K", when o'''>1, may be the same or different;
p is the charge of the complex: 0, 1, 2, 3 or 4; preferably 0, 1 or 2, more preferably 0;
W is a monoanionic counterion;
where the sum of q+r+O''' and the charge p depends on the oxidation state and coordination number of the metal atom used, the charge of the complex and the denticity of the carbene, L" and K" ligands, and on the charge of the carbene and L ligands, with the condition that n is at least 1.

The present invention therefore further provides an organic light-emitting diode in which the at least one emitter material present in the light-emitting layer (c) is at least one carbene complex of the general formula (III).

Most preferably, present invention provides an organic light-emitting diode in which the at least one emitter material present in the light-emitting layer (c) is at least one carbene complex of the general formula (IV):

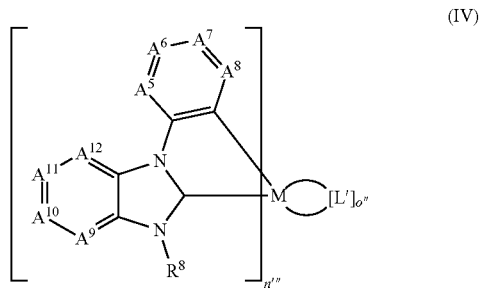

(IV)

wherein
M is Ir,
n''' is 1, 2 or 3,
A$^9$ is CR$^9$ or N;
A$^{10}$ is CR$^{10}$ or N;
A$^{11}$ is CR$^{11}$ or N;
A$^{12}$ is CR$^{12}$ or N;
where 2 A of A$^9$, A$^{10}$, A$^{11}$ and A$^{12}$ are nitrogen atoms and at least one carbon atom is present between two nitrogen atoms in the ring;
R$^8$ is a linear or branched alkyl radical, having from 1 to 6 carbon atoms, a substituted or unsubstituted cycloalkyl radical, having from 3 to 20 carbon atoms, a substituted or unsubstituted aryl radical, having from 6 to 30 carbon atoms, a substituted or unsubstituted heteroaryl radical, having a total of from 5 to 18 carbon atoms and/or heteroatoms,
R$^9$, R$^{10}$, R$^{11}$ and R$^{12}$
are each independently hydrogen, a linear or branched alkyl radical having 1 to 6 carbon atoms, a substituted or unsubstituted cycloalkyl radical, having from 3 to 20 carbon atoms, a substituted or unsubstituted aryl radical having 6 to 30 carbon atoms, a substituted or unsubstituted heteroaryl radical having a total of 5 to 18 carbon atoms and/or heteroatoms,
or
R$^{10}$ and R$^{11}$ form, together with the carbon atoms to which they are bonded, an optionally substituted, unsaturated ring optionally interrupted by at least one heteroatom and having a total of 5 to 18 carbon atoms and/or heteroatoms,
A$^5$ is CR$^{13}$ or N, preferably CR$^{13}$;
A$^6$ is CR$^{14}$ or N, preferably CR$^{14}$;
A$^7$ is CR$^{15}$ or N, preferably CR$^{15}$;
A$^8$ is CR$^{16}$ or N, preferably CR$^{16}$;
R$^{13}$, R$^{14}$, R$^{15}$ and R$^{16}$
are each independently hydrogen, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action, preferably are each independently hydrogen, a linear or branched alkyl radical, having from 1 to 6 carbon atoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from the group consisting of halogen radicals, preferably F or Cl, more preferably F; $CF_3$, CN and $SiMe_3$;

L' is a monoanionic bidentate ligand, and o'' is 0, 1 or 2,

The compound of formula (IV) is more preferably a compound of the formula:

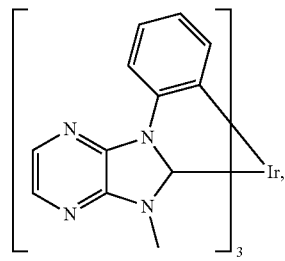
(BE-1)

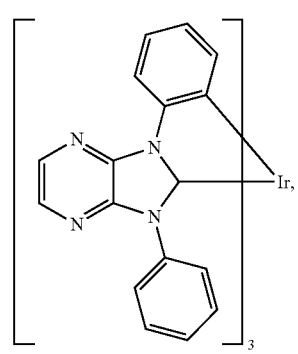
(BE-2)

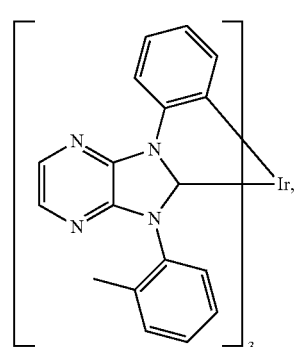
(BE-3)

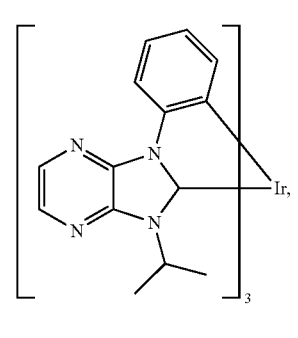
(BE-4)

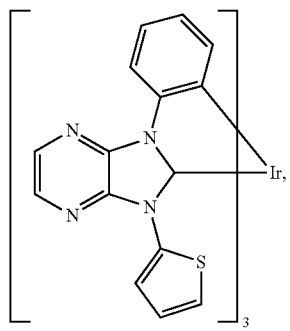
(BE-5)

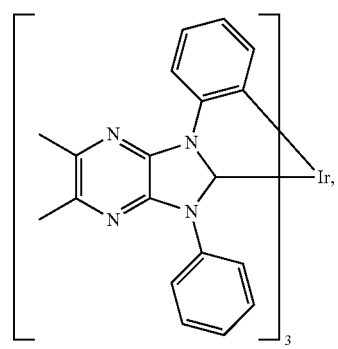
(BE-6)

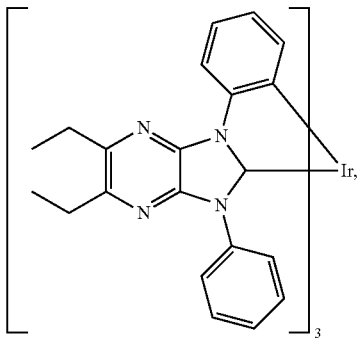
(BE-7)

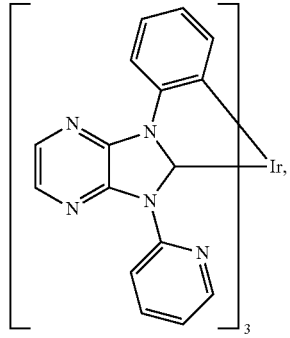
(BE-8)

(BE-9)
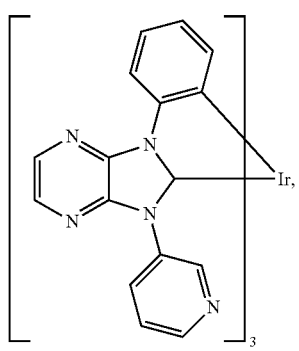
(BE-13)
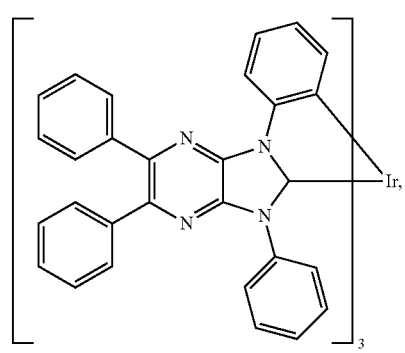
(BE-10)
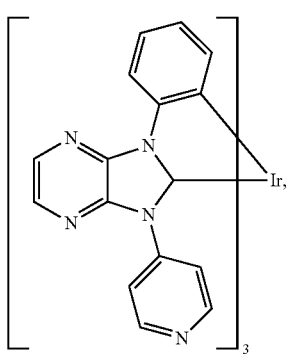
(BE-14)
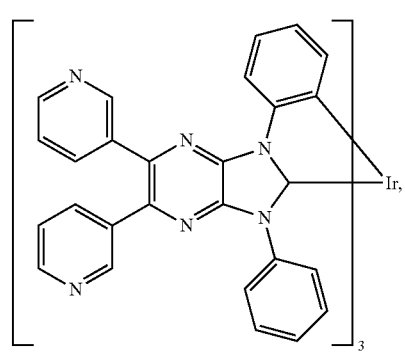
(BE-11)
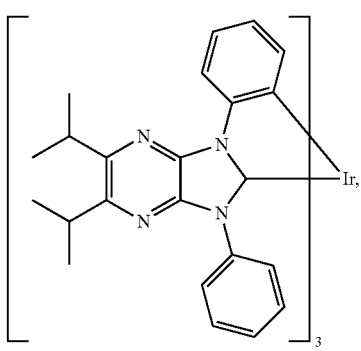
(BE-15)
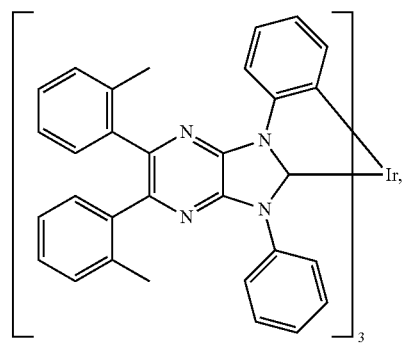
(BE-12)
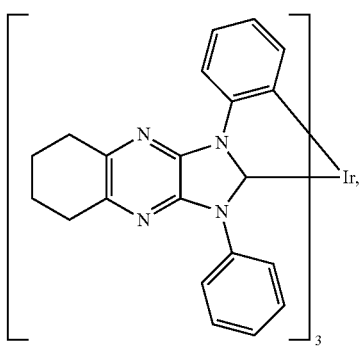
(BE-16)
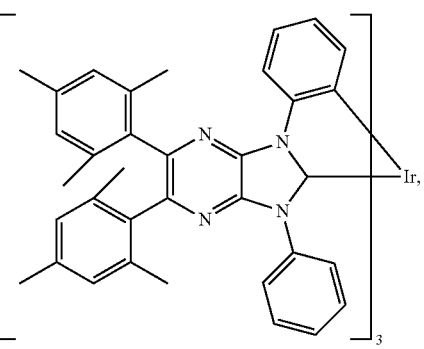

-continued
(BE-17)
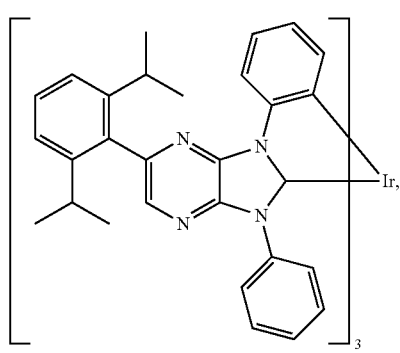
(BE-18)
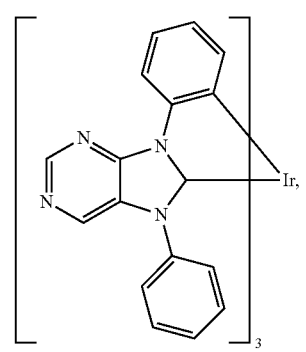
(BE-19)
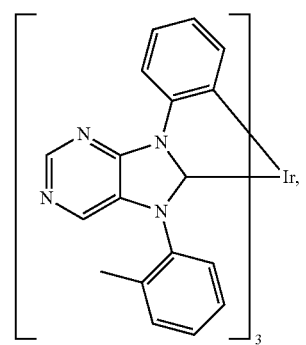
(BE-20)
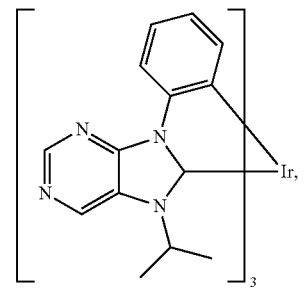
(BE-21)
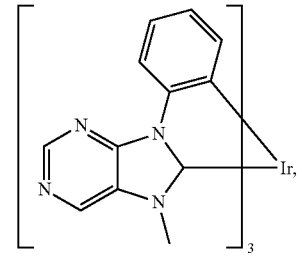
-continued
(BE-22)
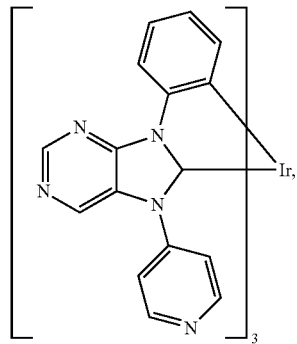
(BE-23)
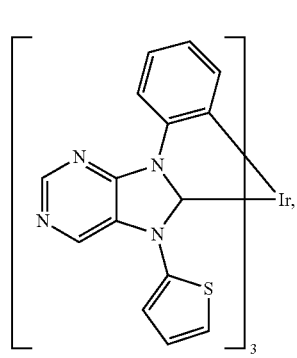
(BE-24)
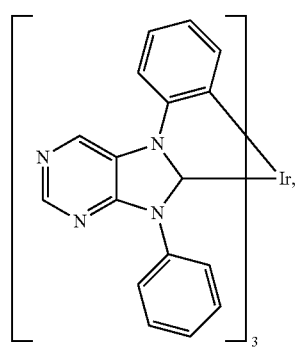
(BE-25)
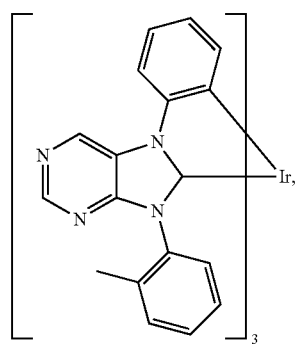

(BE-26)
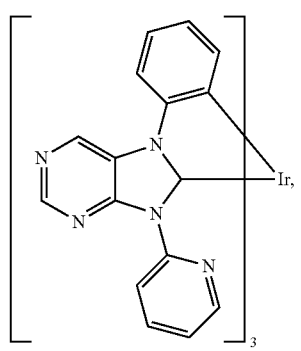
(BE-27)
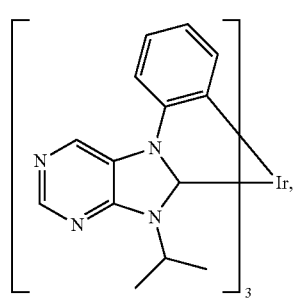
(BE-28)
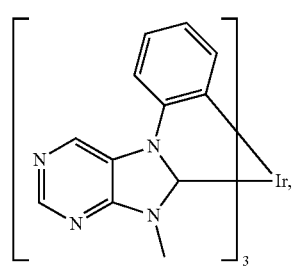
(BE-29)
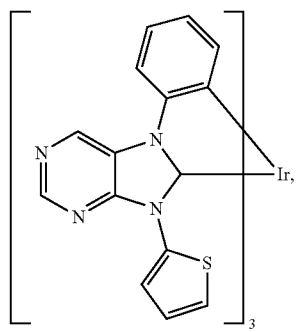
(BE-30)
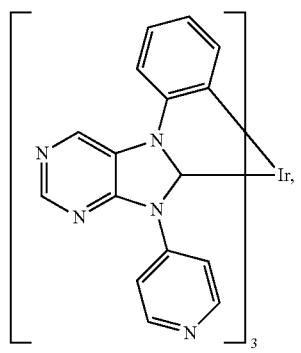
(BE-31)
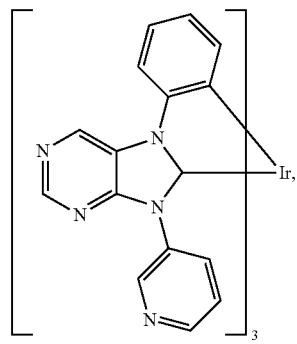
(BE-32)
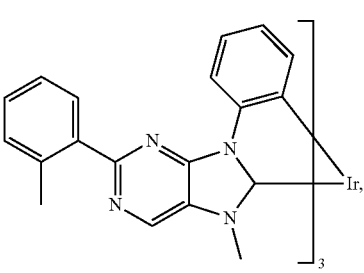
(BE-33)
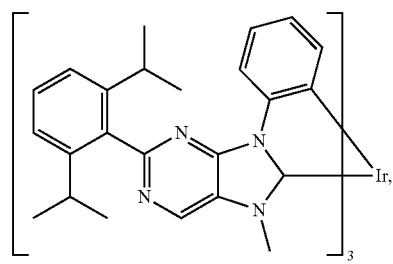
(BE-34)
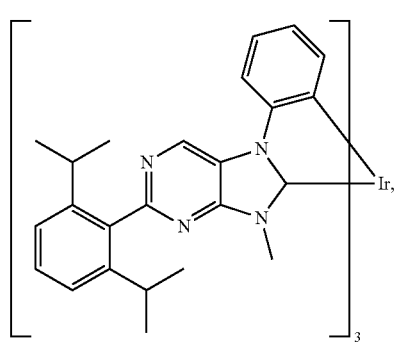
(BE-35)
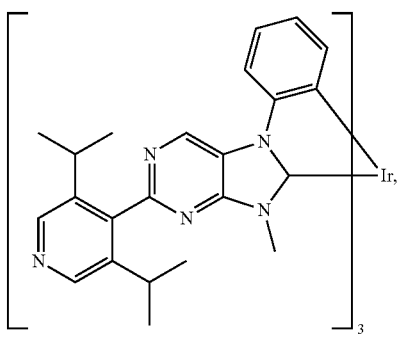

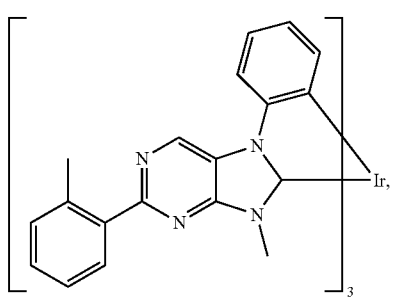
(BE-36)
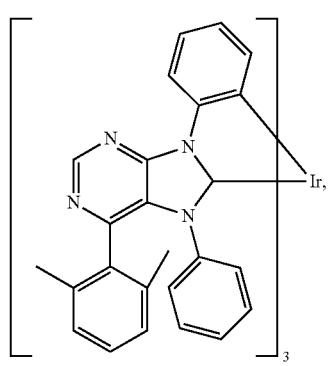
(BE-37)
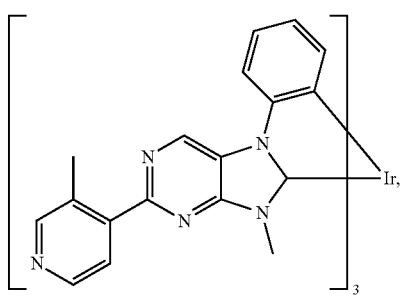
(BE-38)
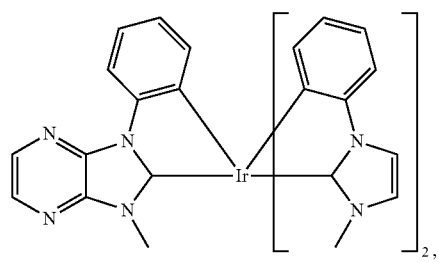
(BE-39)
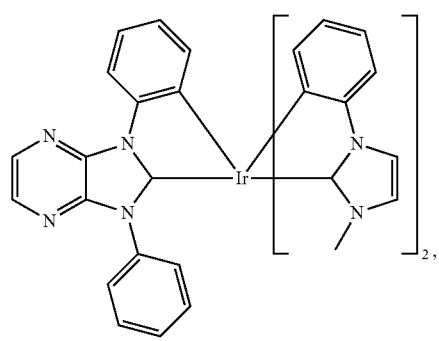
(BE-40)
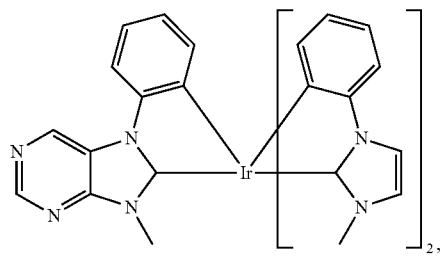
(BE-41)
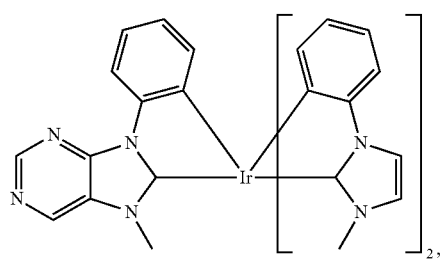
(BE-42)
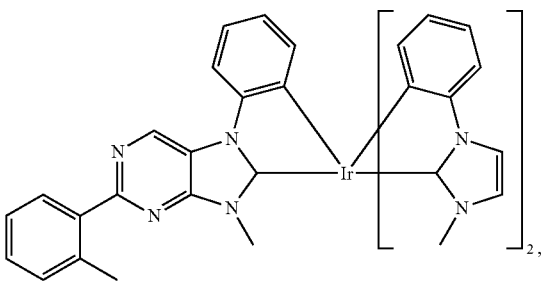
(BE-43)
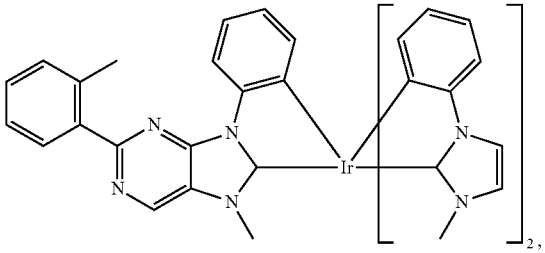
(BE-44)
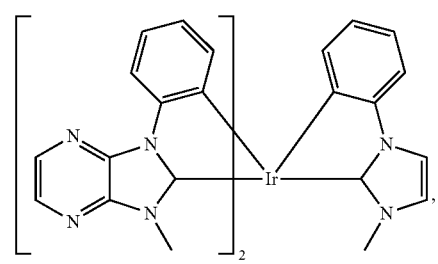
(BE-45)

(BE-46)
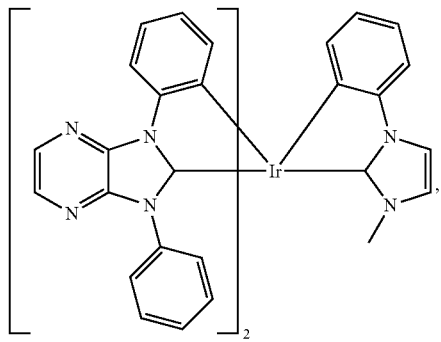
(BE-47)
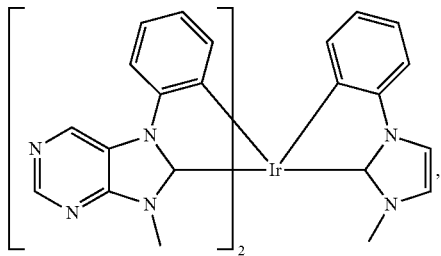
(BE-48)
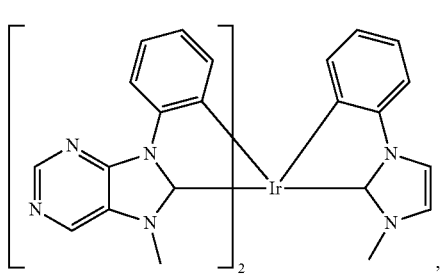
(BE-49)
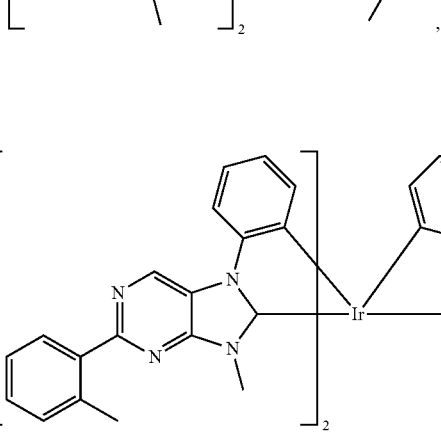
(BE-50)
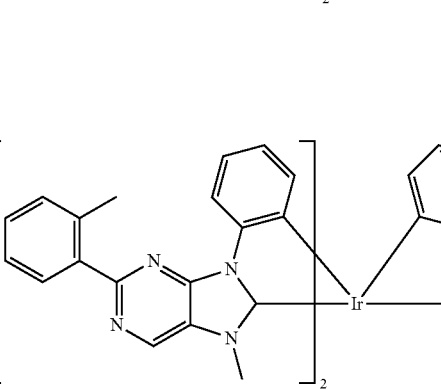
(BE-51)
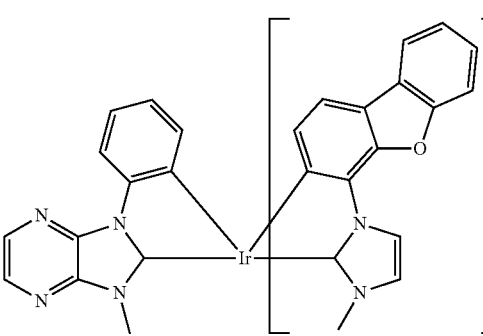
(BE-52)
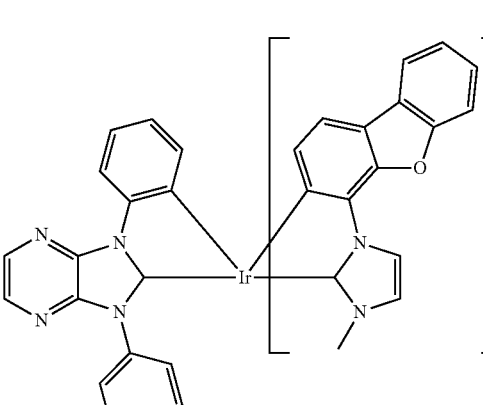
(BE-53)
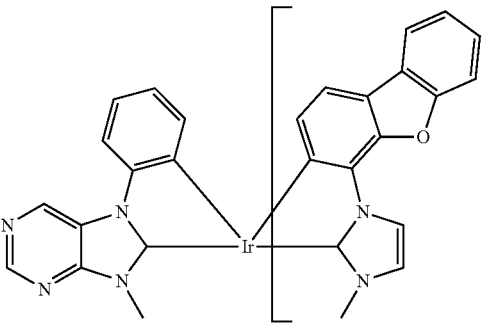
(BE-54)
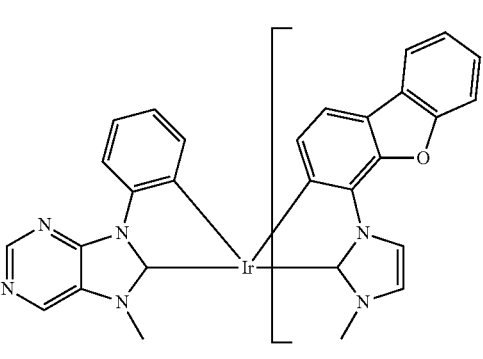

-continued
(BE-55)
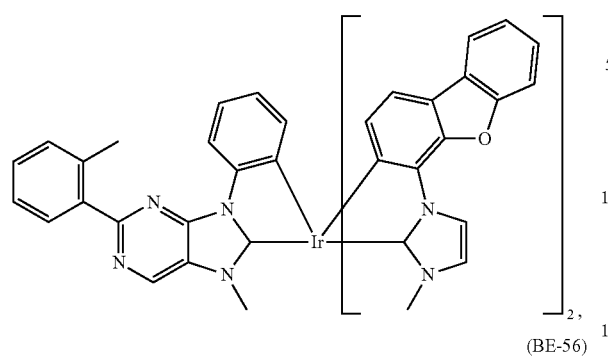
(BE-59)
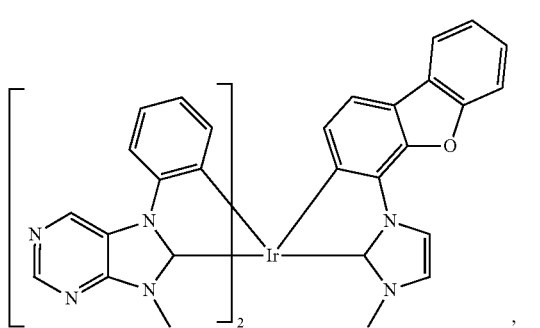
(BE-56)
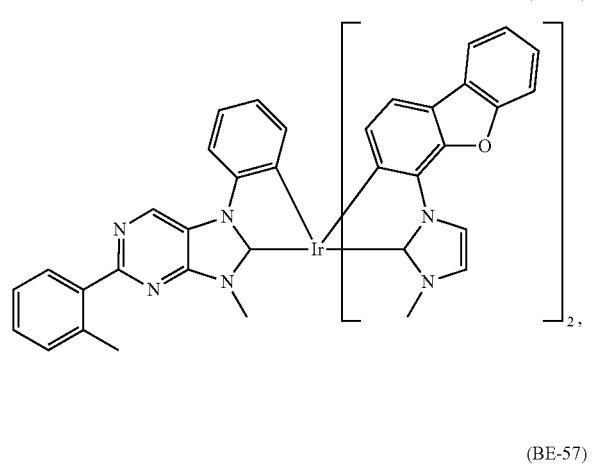
(BE-60)
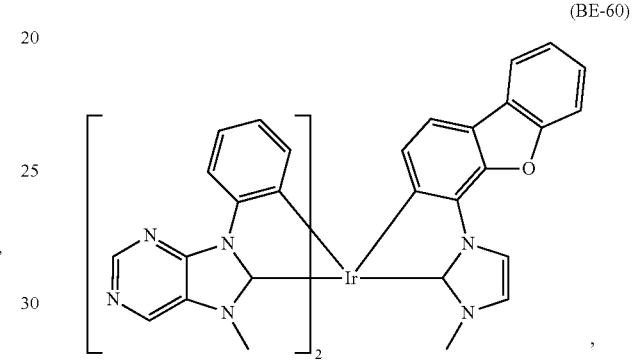
(BE-57)
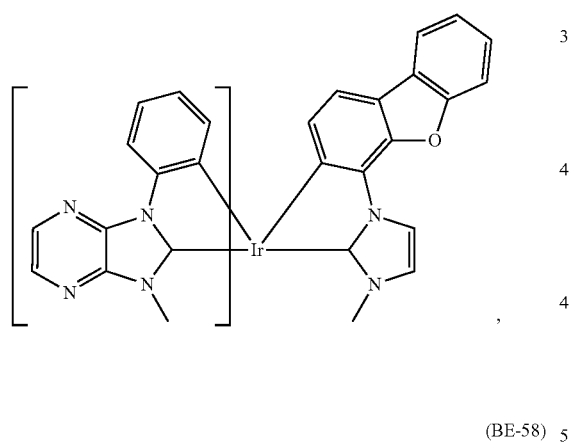
(BE-61)
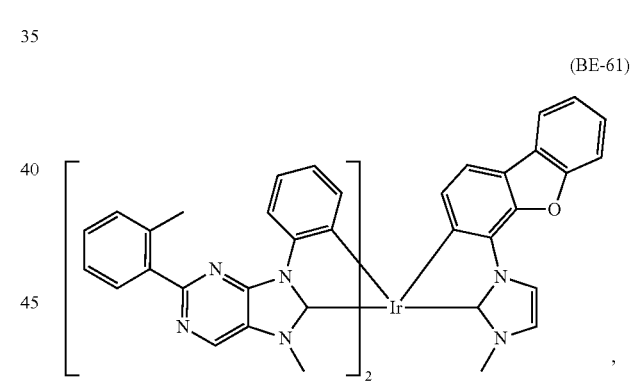
(BE-58)
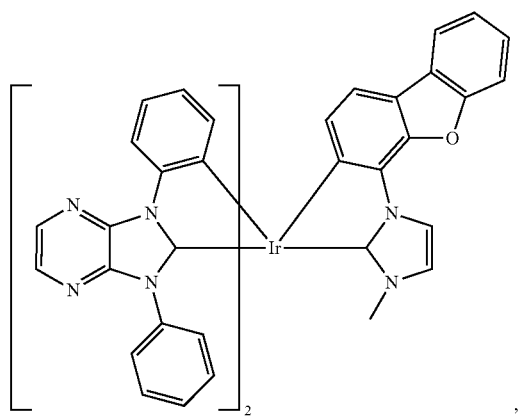
(BE-62)
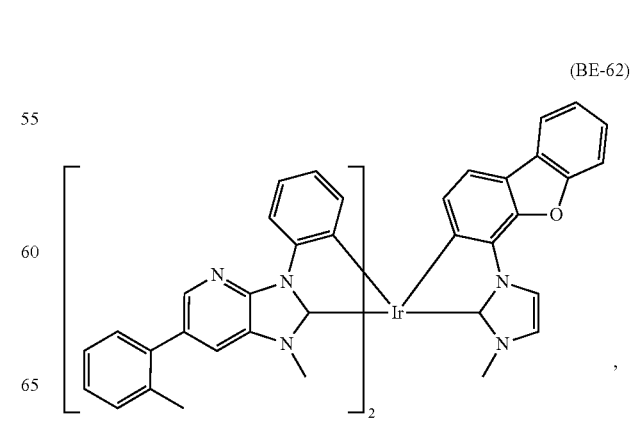

-continued
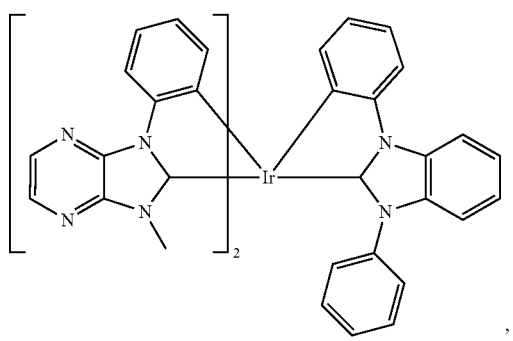
(BE-63)
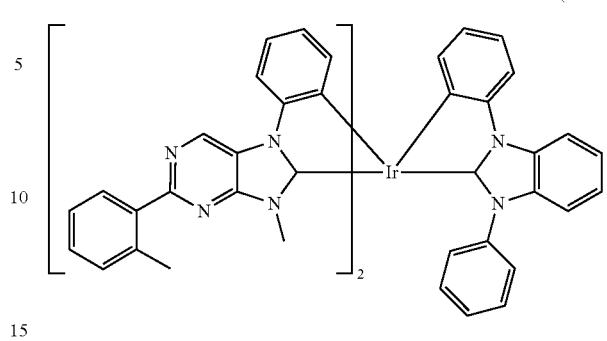
(BE-67)
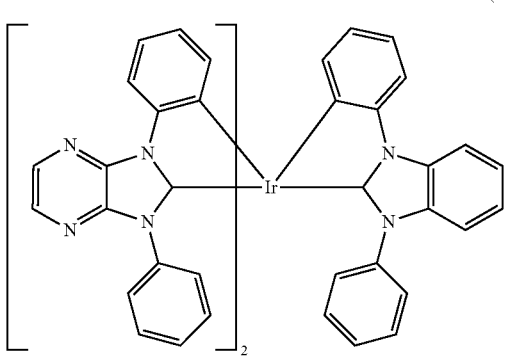
(BE-64)
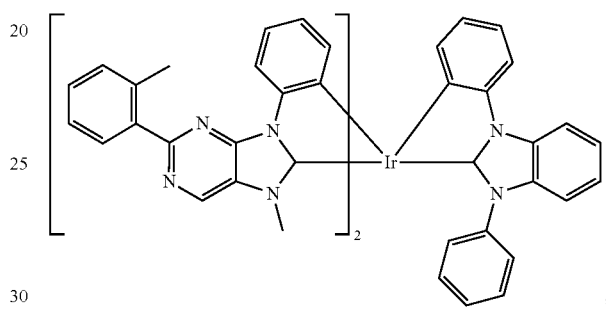
(BE-68)
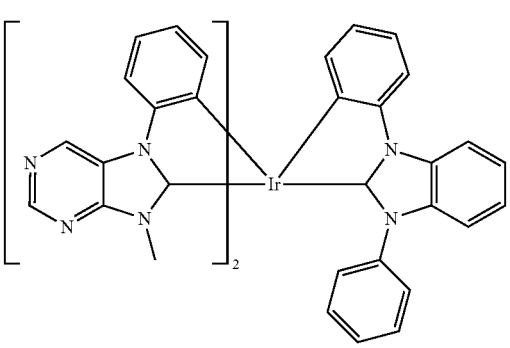
(BE-65)
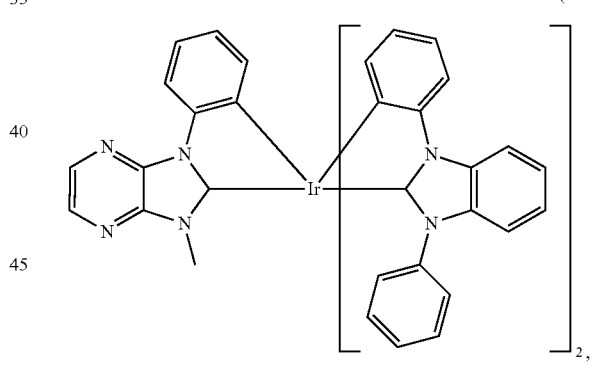
(BE-69)
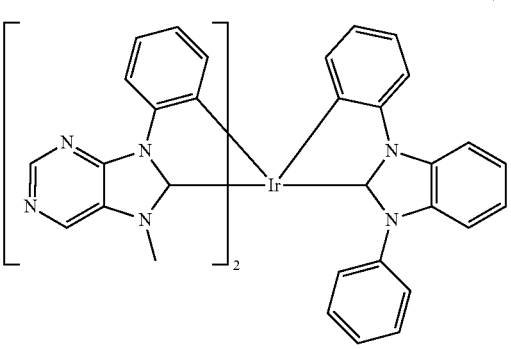
(BE-66)
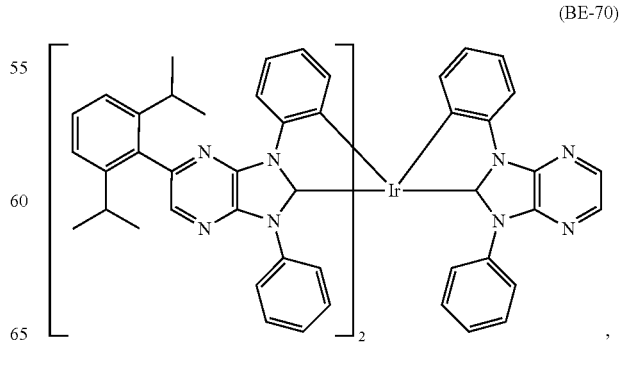
(BE-70)

(BE-71)
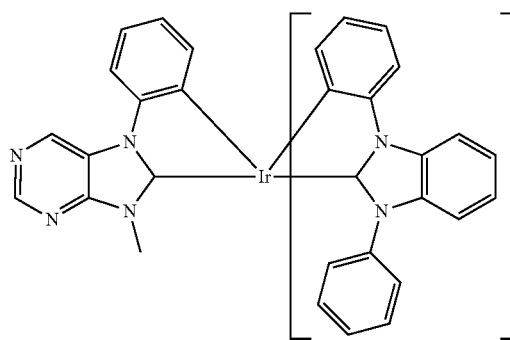
(BE-75)
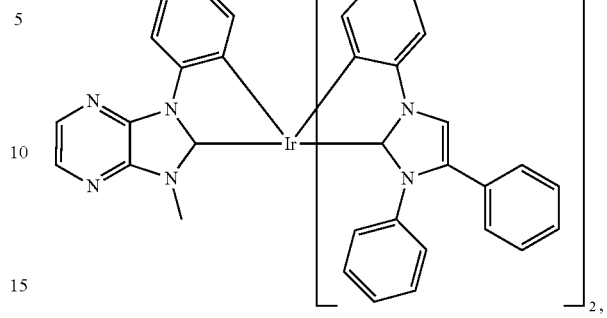
(BE-72)
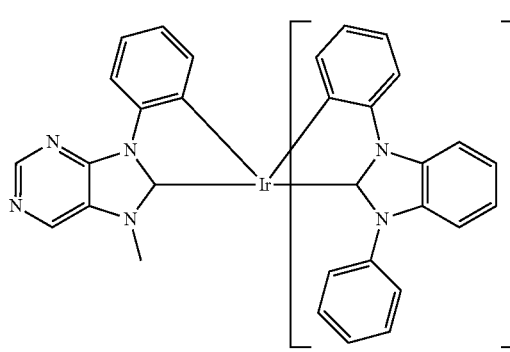
(BE-76)
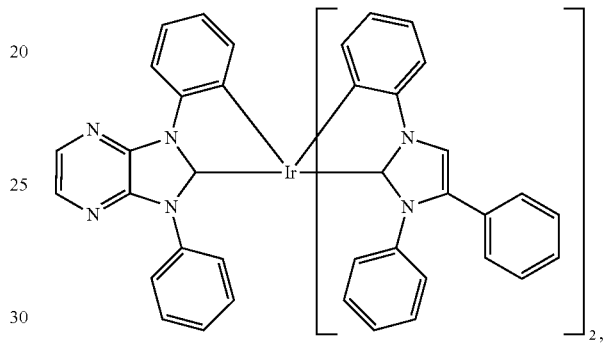
(BE-73)
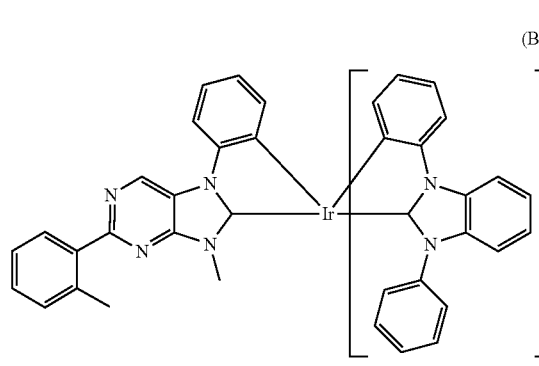
(BE-77)
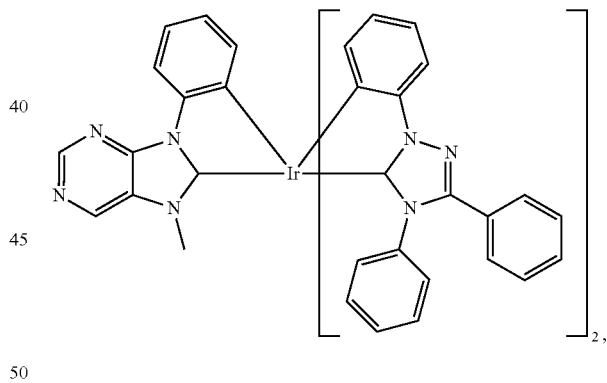
(BE-74)
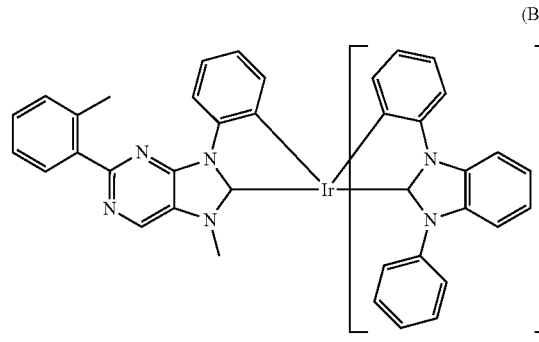
(BE-78)
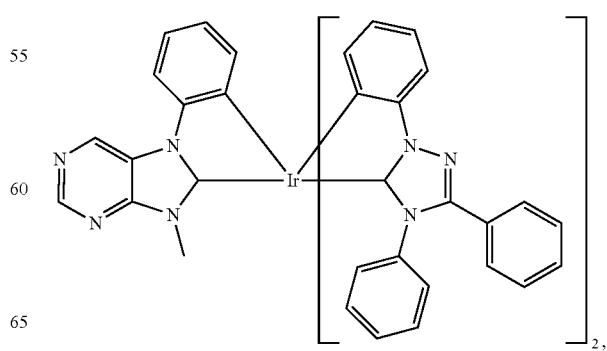

(BE-79)
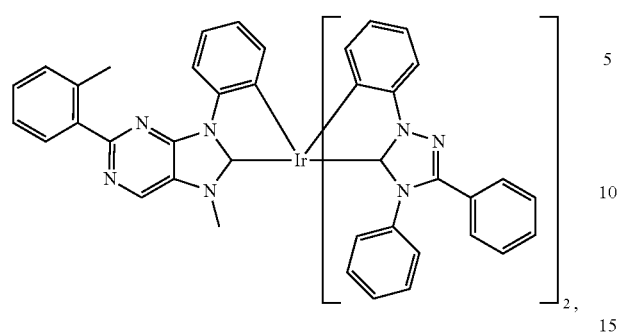
(BE-83)
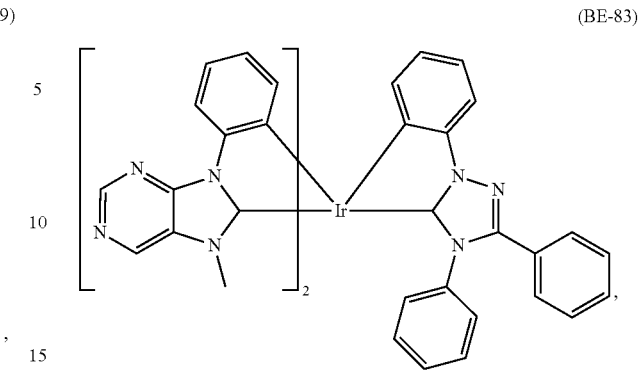
(BE-80)
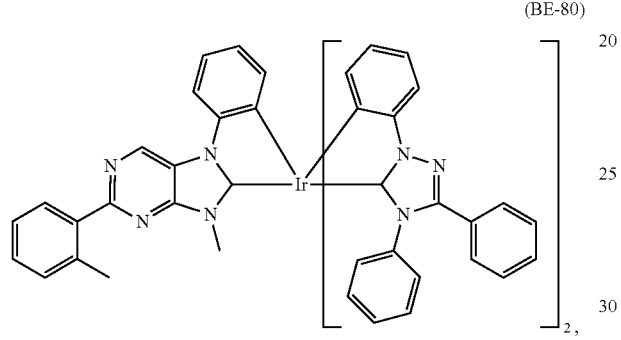
(BE-84)
(BE-81)
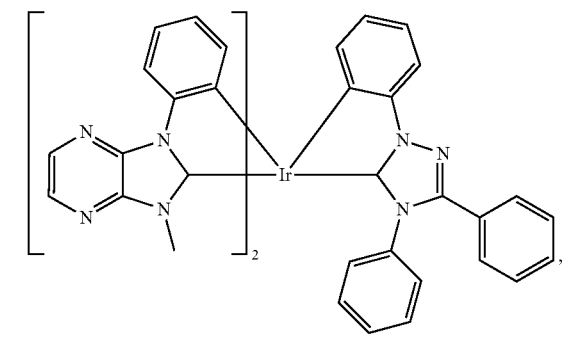
(BE-85)
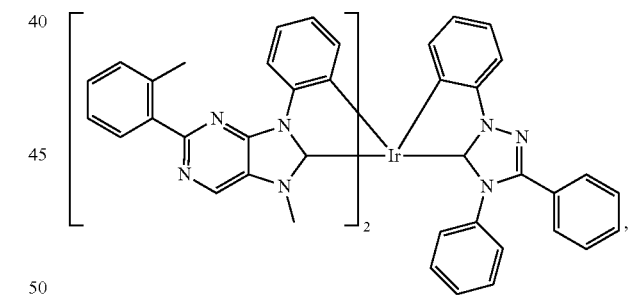
(BE-82)
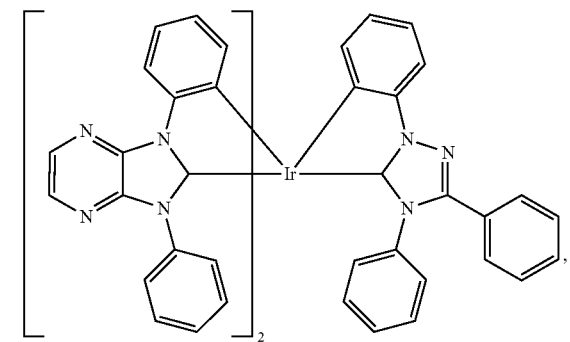
(BE-86)
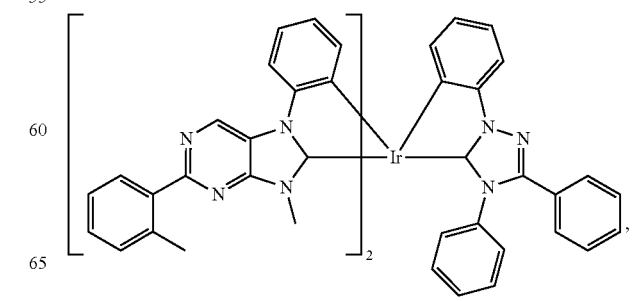

-continued
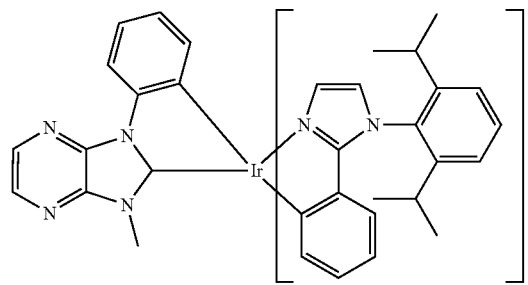
(BE-87)
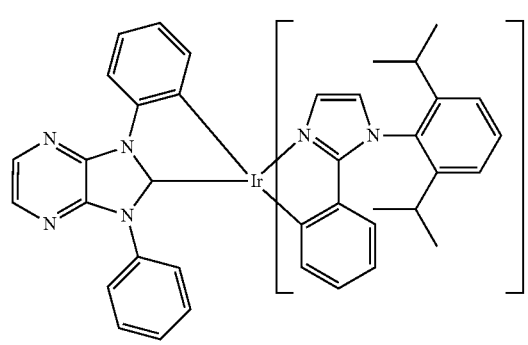
(BE-88)
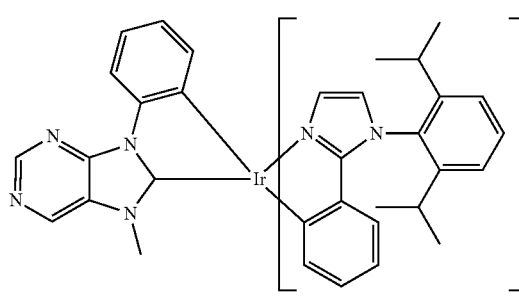
(BE-89)
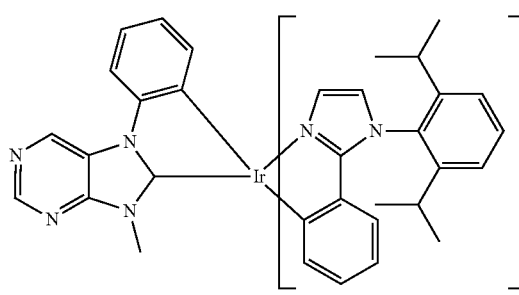
(BE-90)
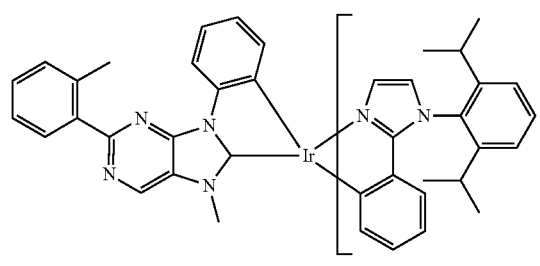
-continued
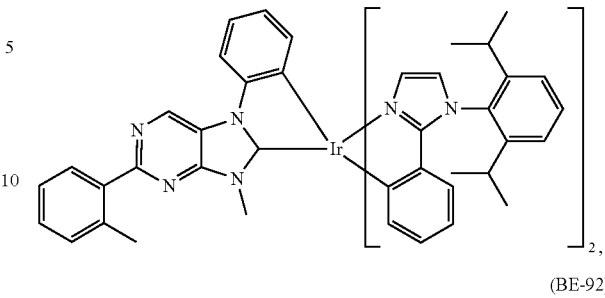
(BE-91)
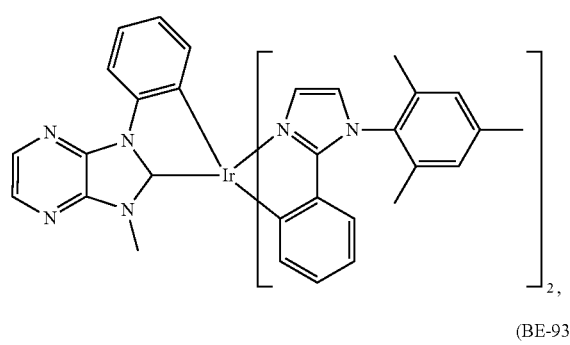
(BE-92)
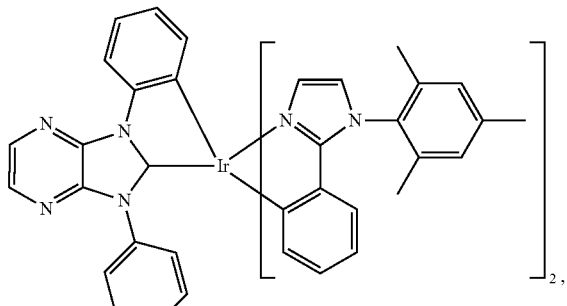
(BE-93)
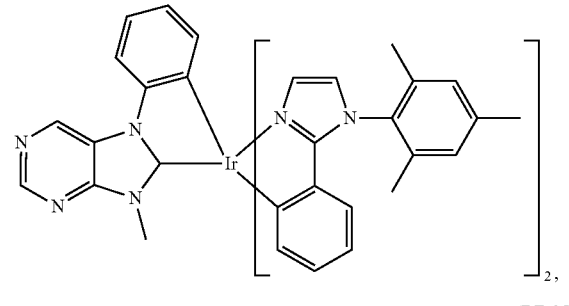
(BE-94)
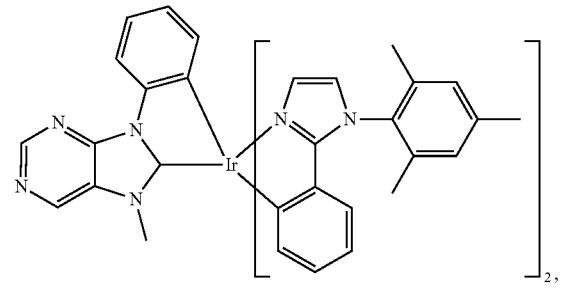
(BE-95)

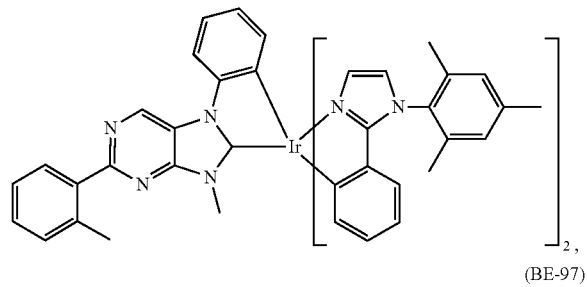
(BE-96)
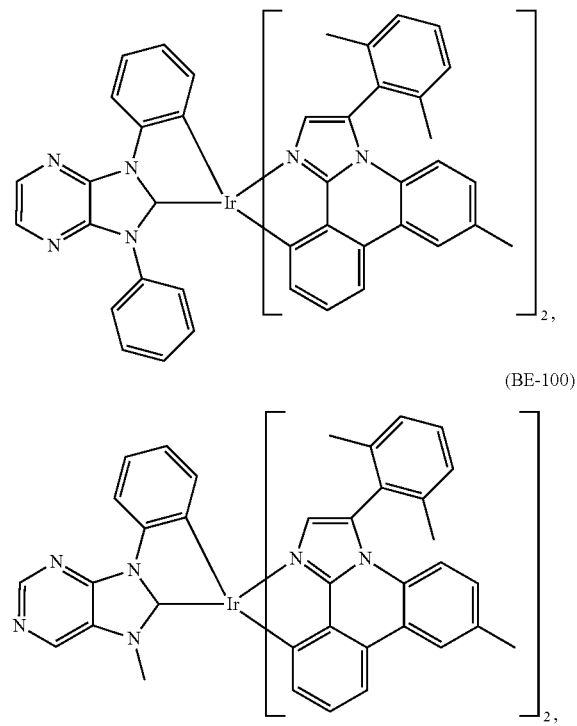
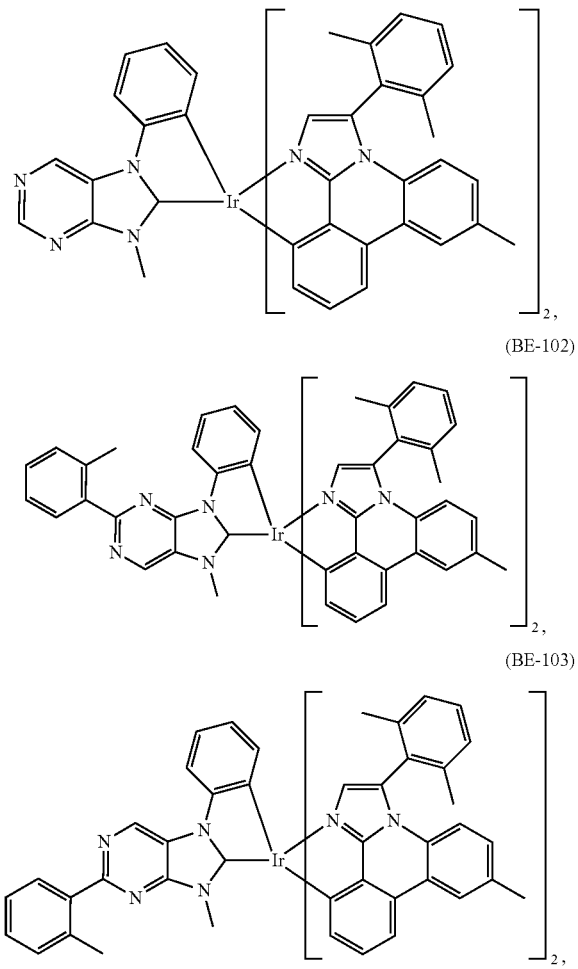
Further suitable non-carbene emitter materials are mentioned below:
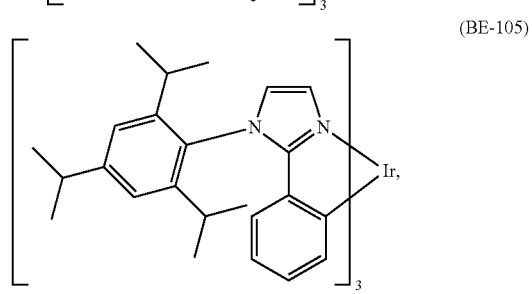

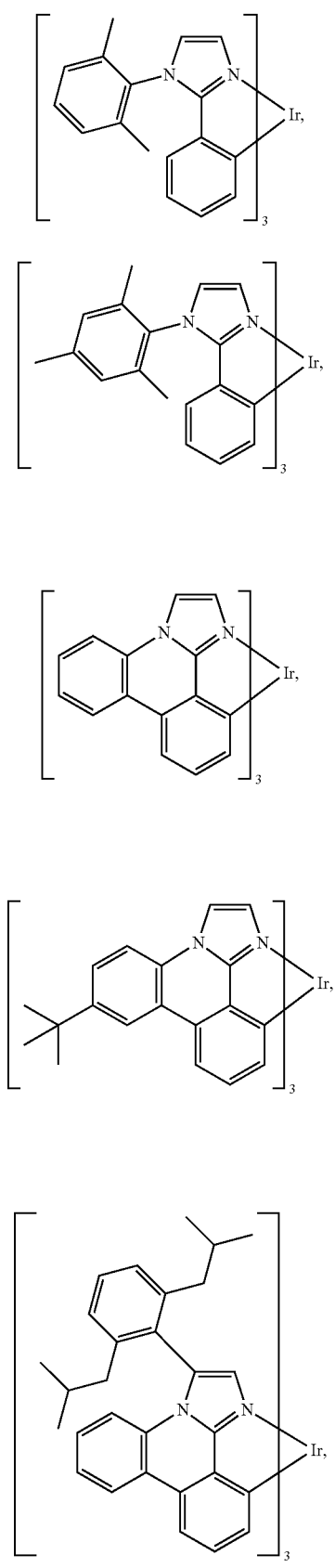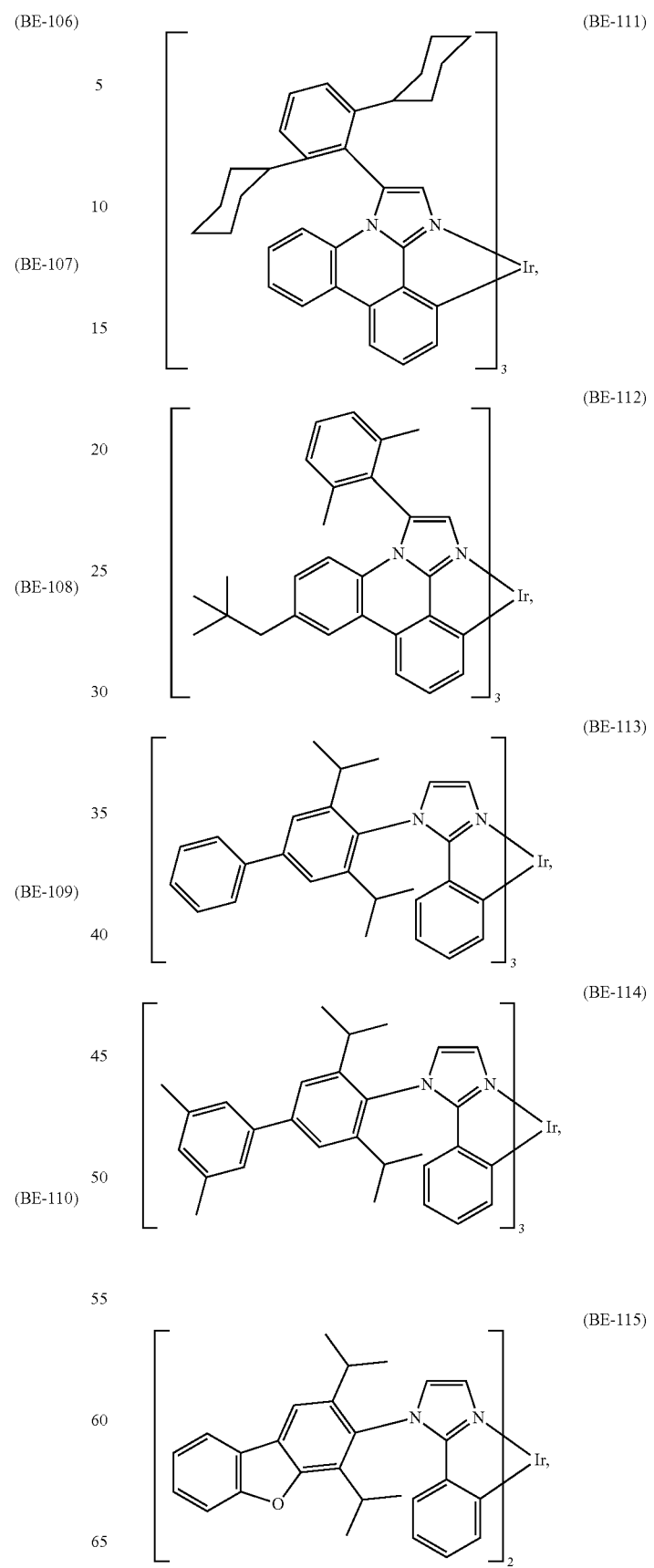

(BE-116) 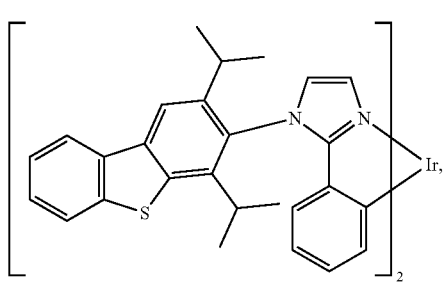
(BE-117) 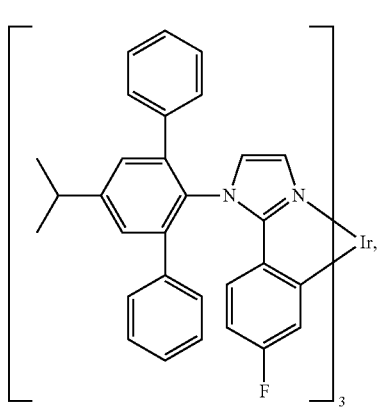
(BE-118) 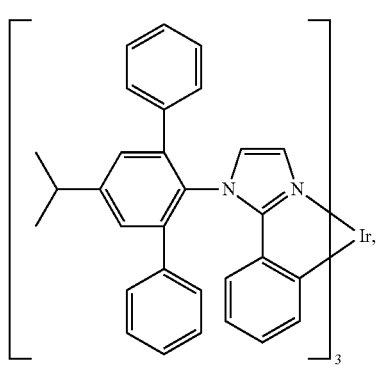
(BE-119) 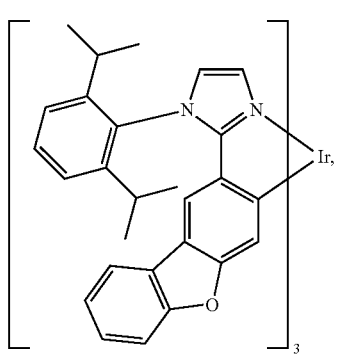
(BE-120) 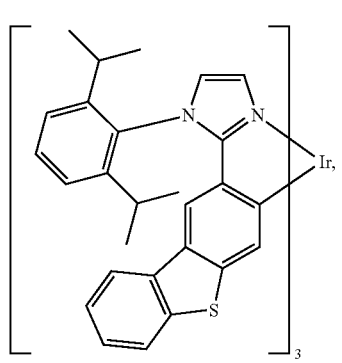
(BE-121) 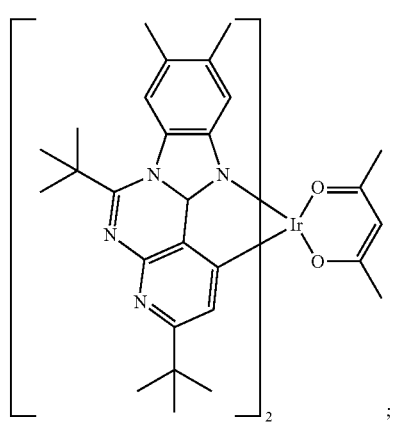
(BE-122) 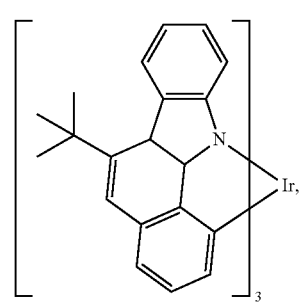
(BE-123) 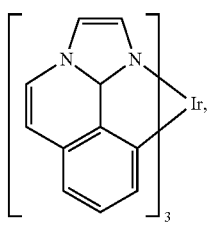
(BE-124) 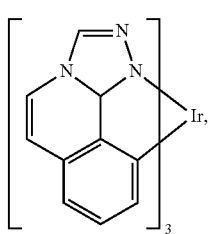

-continued
(BE-125)
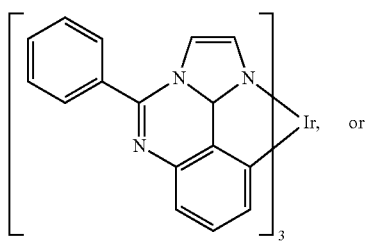
or
(BE-126)
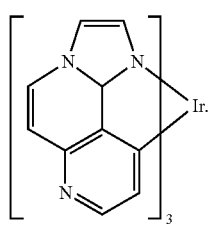
More preferably, the compound of formula (IV) is selected from the group consisting of the following compounds:
(BE-1)
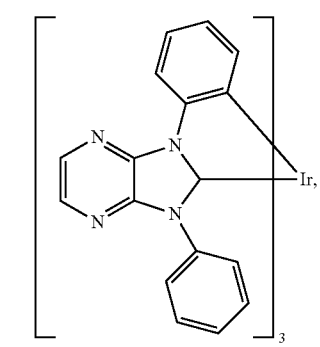
(BE-7)
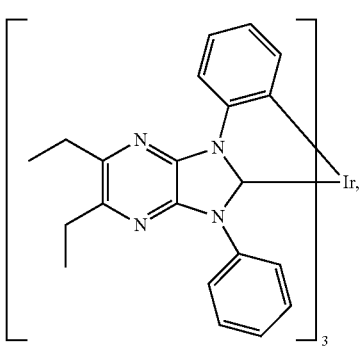
(BE-12)
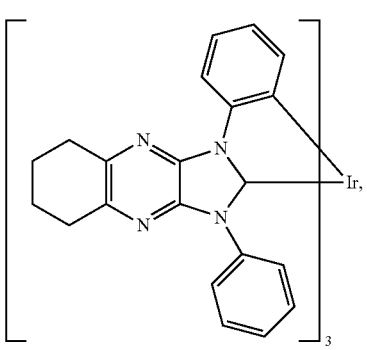
-continued
(BE-16)
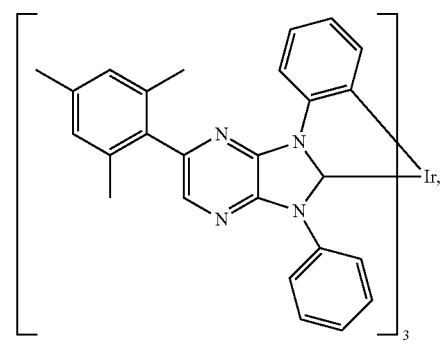
(BE-64)
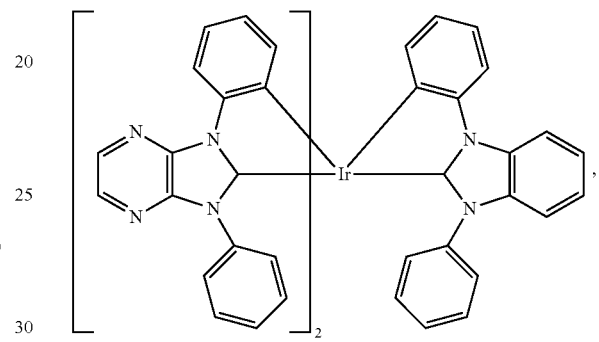
(BE-70)
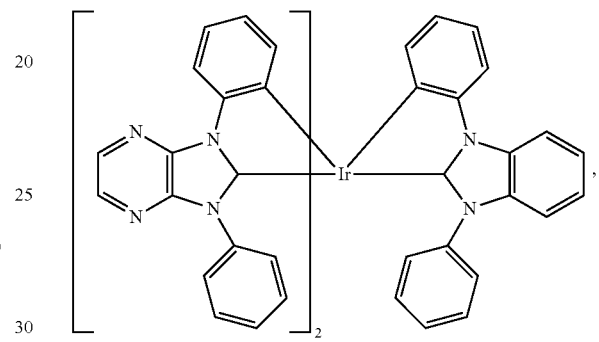
The most preferred phosphorescent blue emitters are
(BE-1)
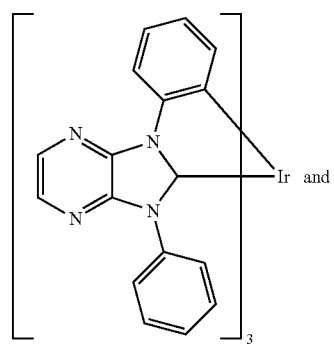
Ir and -continued

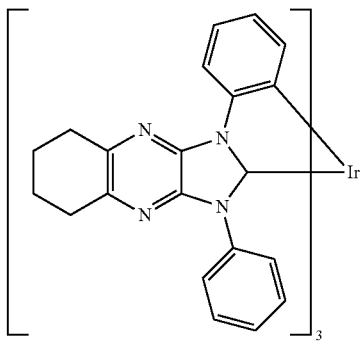

(BE-12)

The homoleptic metal-carbene complexes may be present in the form of facial or meridional isomers, preference being given to the facial isomers.

Suitable carbene complexes of formula (IV) and their preparation processes are for example described in WO 2011/073149 A1.

Host (Matrix) Material

The light-emitting layer may comprise further components in addition to the emitter material. For example, a fluorescent dye may be present in the light-emitting layer in order to alter the emission color of the emitter material. In addition—in a preferred embodiment—a host (matrix) material can be used. This matrix material may be a polymer, for example poly(N-vinylcarbazole) or polysilane. The matrix material may, however, likewise be a small molecule, for example 4,4'-N,N'-dicarbazolebiphenyl (CDP=CBP) or tertiary aromatic amines, for example TCTA.

Suitable as host material are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the host materials specified in the following applications: WO2008/034758, WO2009/003919.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No, 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co) polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co) polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709 and European patent applications EP12175635.7 and EP12185230.5 and EP12191408.9 (in particular page 25 to 29 of EP12191408.9).

In a particularly preferred embodiment, one or more compounds of the general formula (V) specified hereinafter are used as host material.

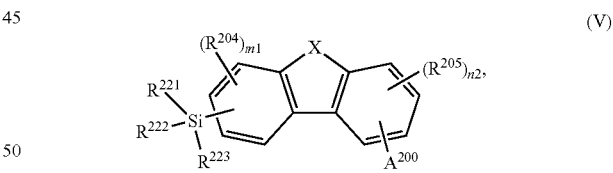

(V)

wherein

X is NR, S, O or PR;

R is aryl, heteroaryl, alkyl, cycloalkyl, or heterocycloalkyl;

$A^{200}$ is —$NR^{206}R^{207}$, —$P(O)R^{208}R^{209}$, —$PR^{210}R^{211}$, —$S(O)_2R^{212}$, —$S(O)R^{213}$, —$SR^{214}$, or —$OR^{215}$;

$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;

$R^{224}$ and $R^{225}$ are independently of each other alkyl, cycloalkyl, heterocycloalkyl, aryl, heteroaryl, a group $A^1$, or a group having donor, or acceptor characteristics;

n2 and m1 are independently of each other 0, 1, 2, or 3;

$R^{206}$, $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl.

Compounds of formula (V) and their preparation processes, such as, for example

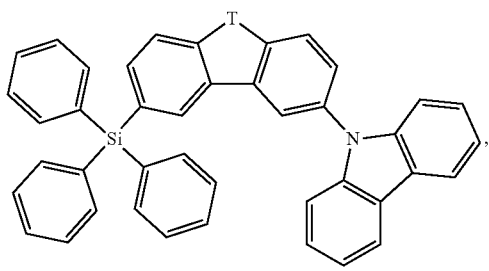
(SH-4)

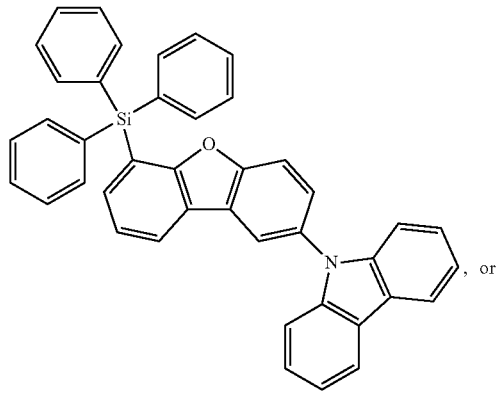
(SH-5), or

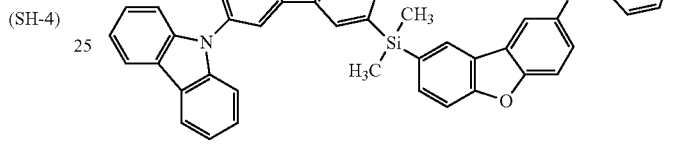
(SH-6)

are described in WO 2010/079051 A1 (in particular pages on 19 to 26 and in tables on pages 27 to 34, pages 35 to 37 and pages 42 to 43).

Additional host materials on basis of dibenzofurane are, for example, described in US 2009066226, EP1 885 818 B1, EP 1 970 976, EP 1 998 388 and EP 2 034 538. Examples of particularly preferred host materials are shown below:

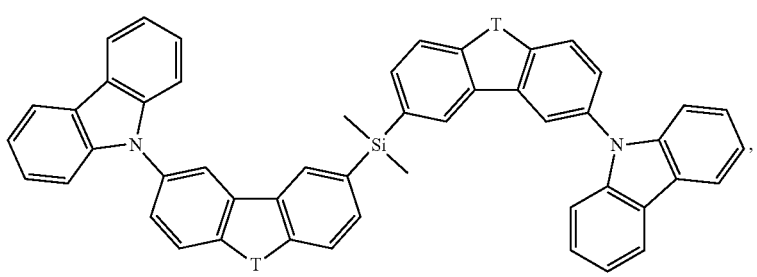

-continued
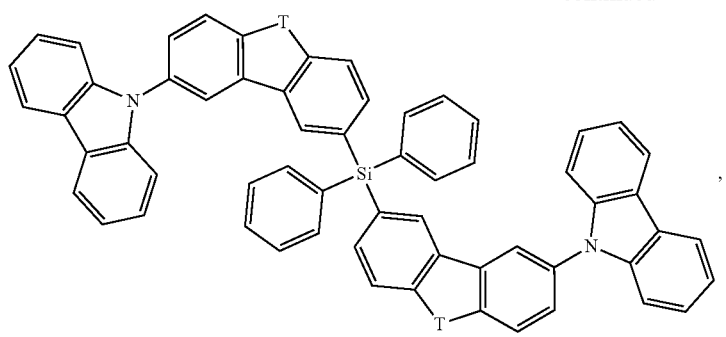
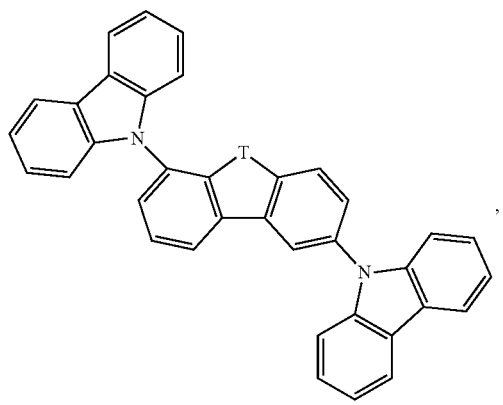
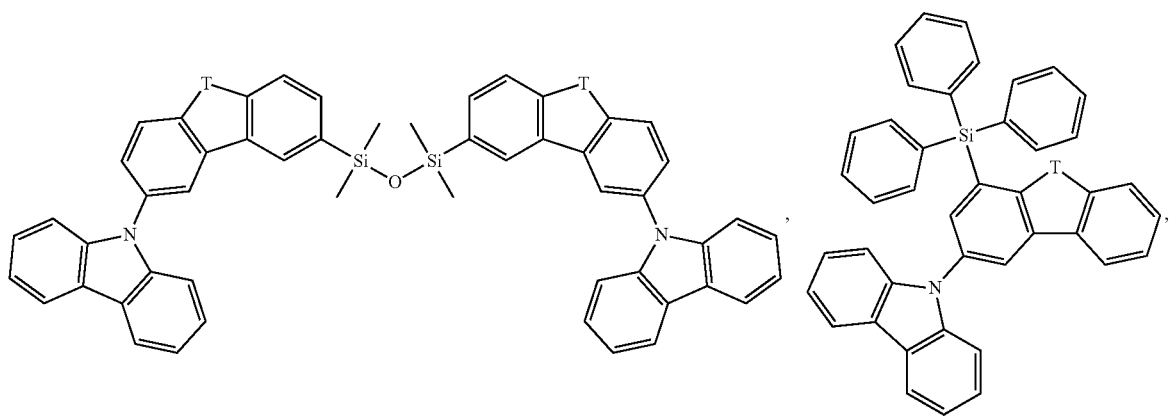
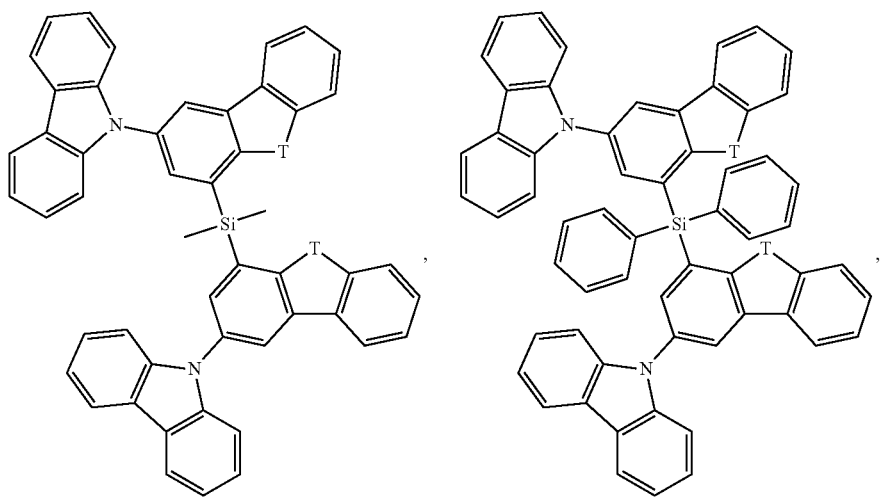

-continued
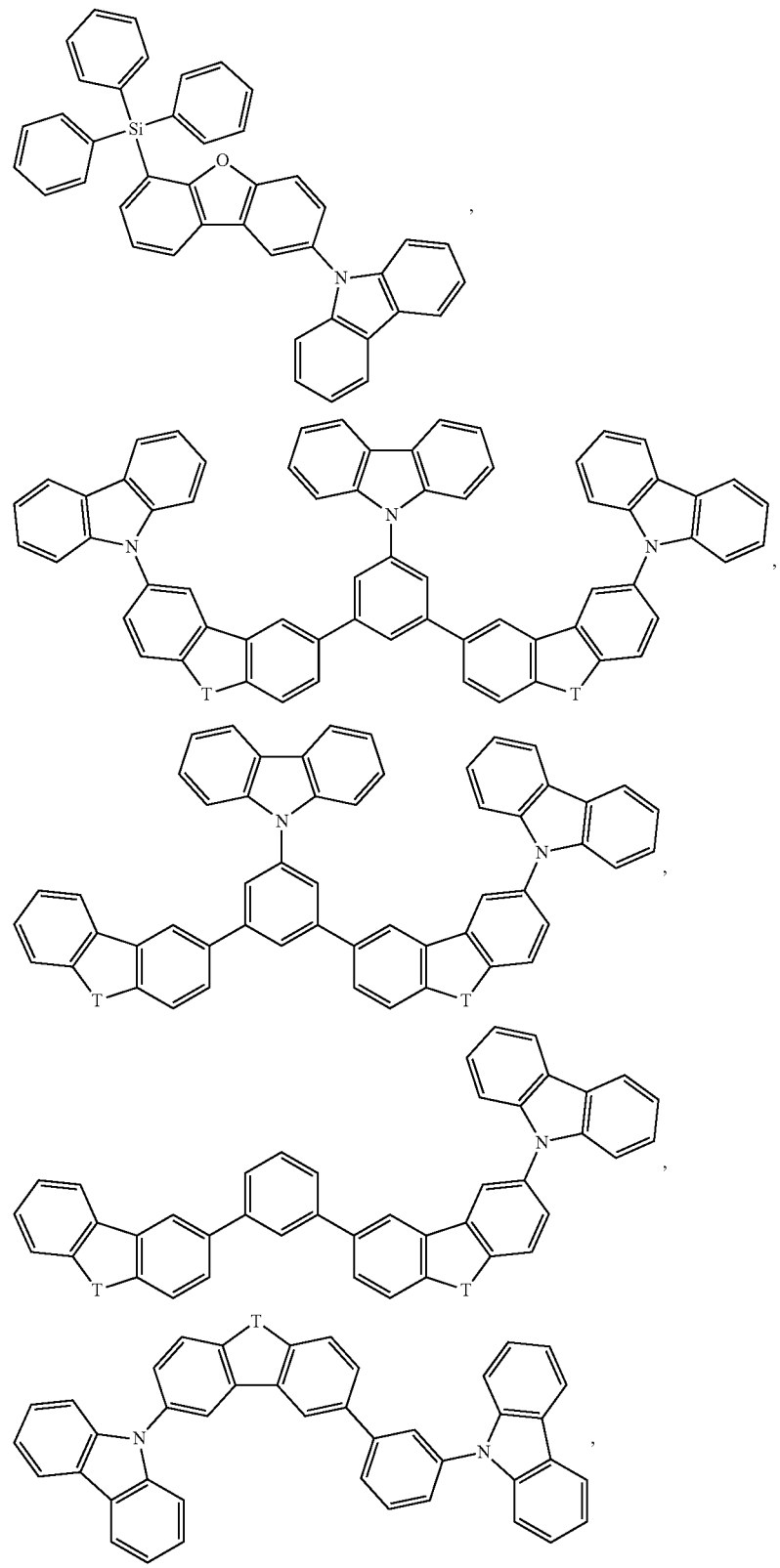

-continued
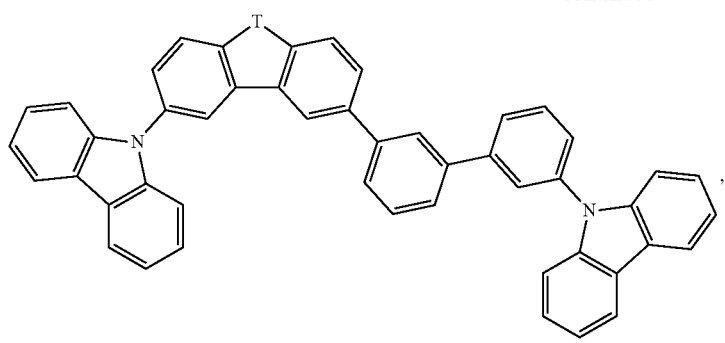
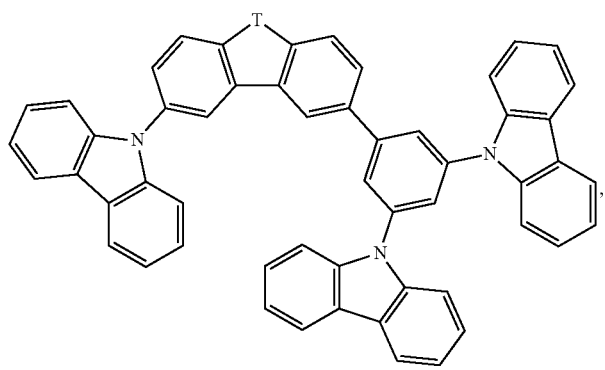
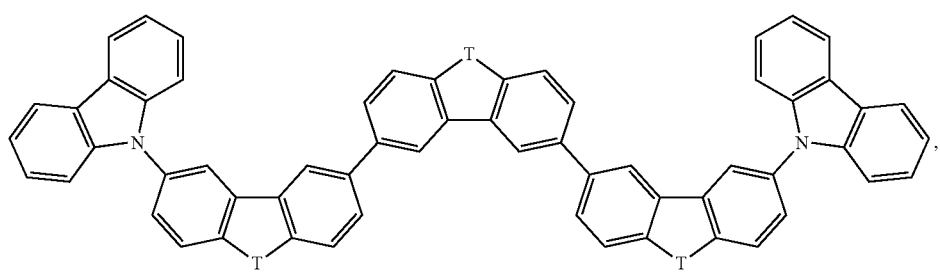
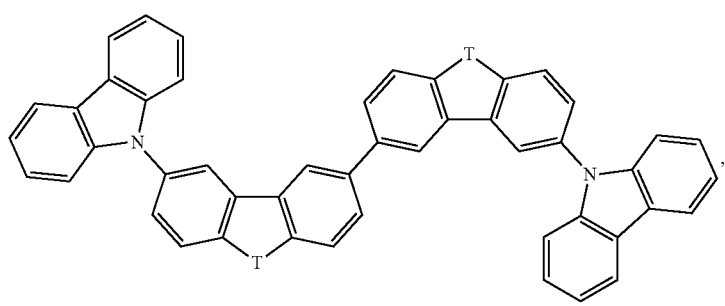
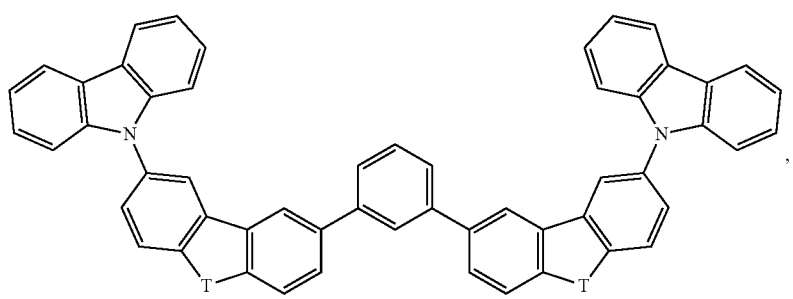

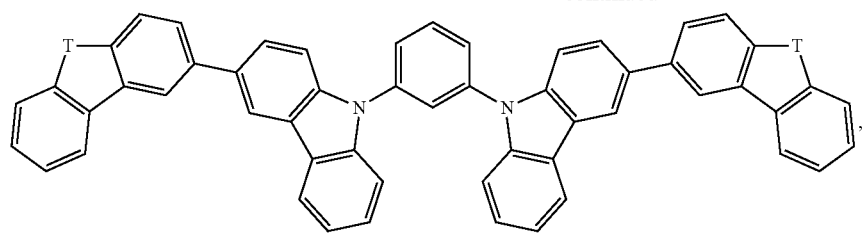
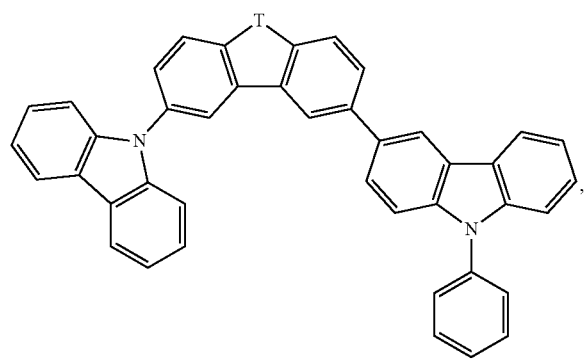
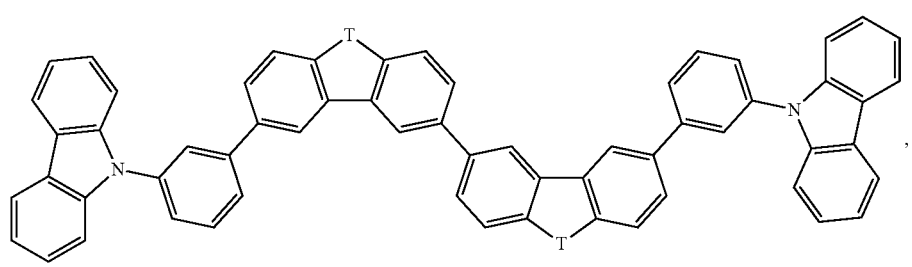
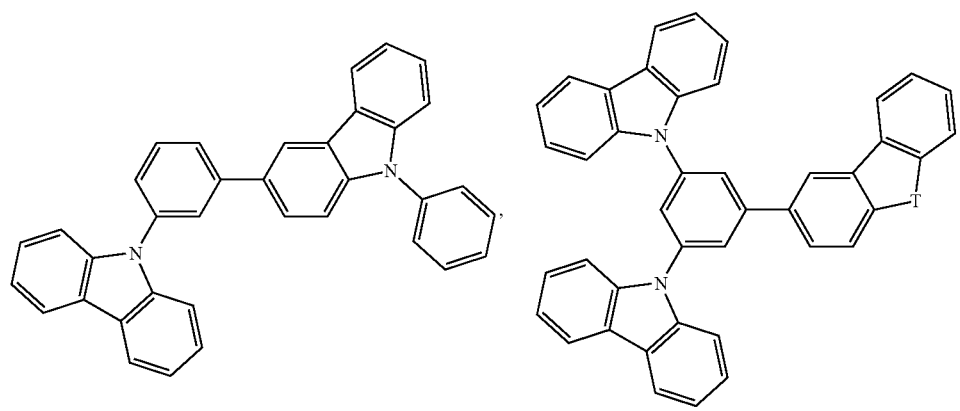
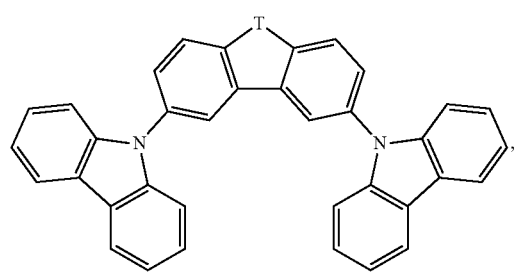

-continued
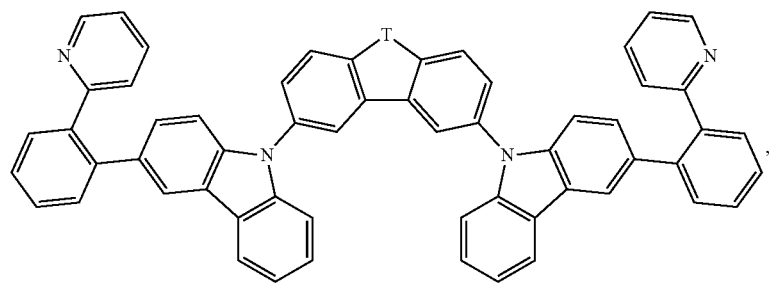
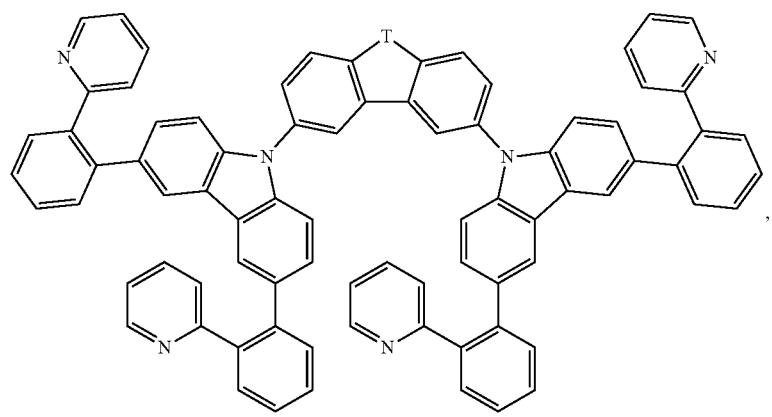
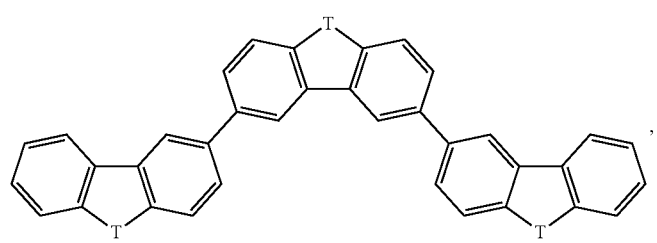
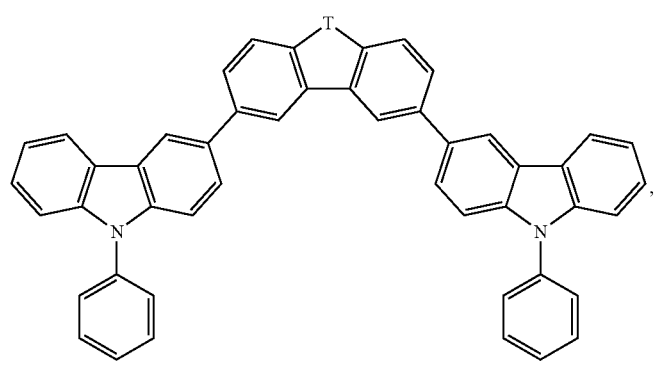
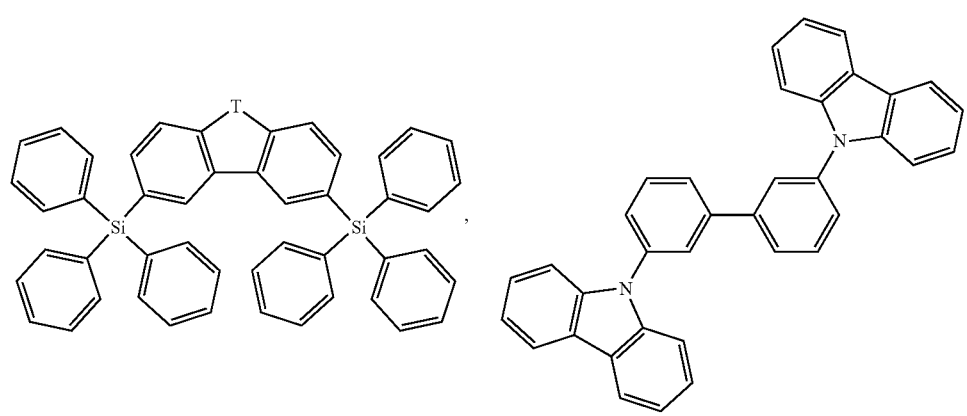

91
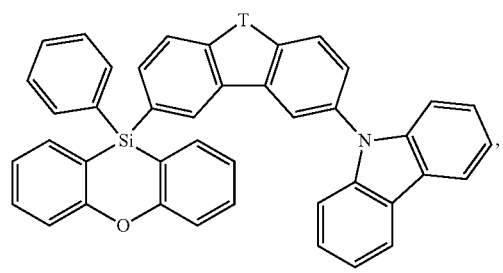
-continued
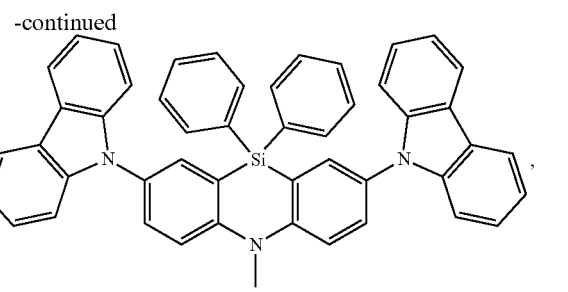
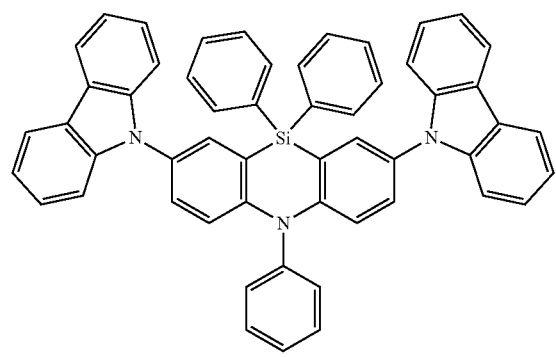
and
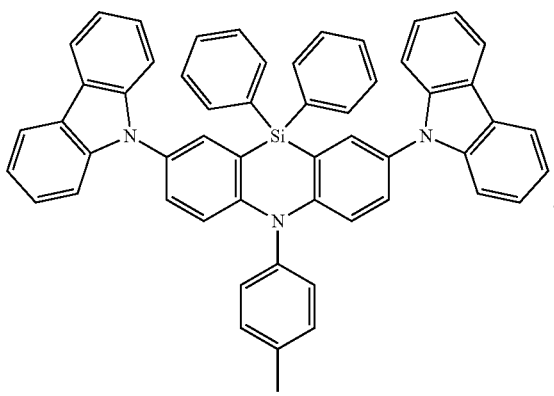
In the above-mentioned compounds T is O, or S, preferably O. If T occurs more than one time in a molecule, all groups T have the same meaning.
The most preferred host compounds are shown below:
(SH-1)
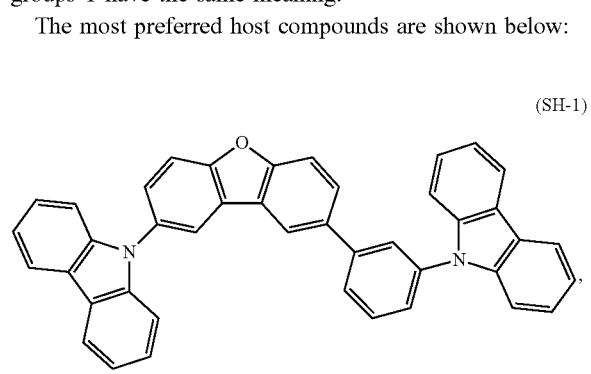
(SH-2)
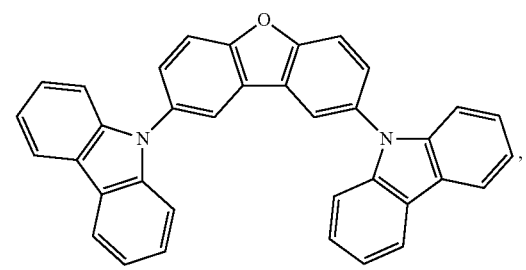
-continued
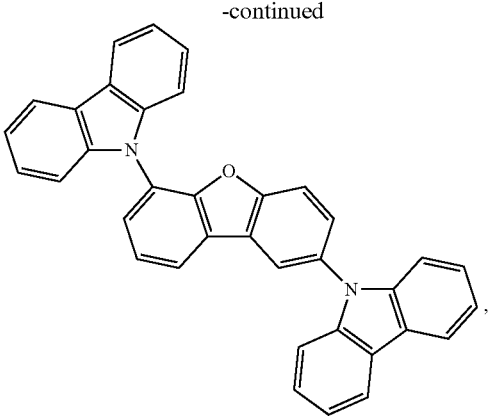
(SH-3), (SH-4), (SH-5), (SH-6)
(SH-7)
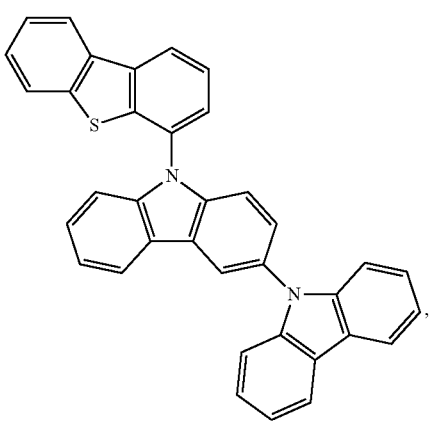

(SH-8)

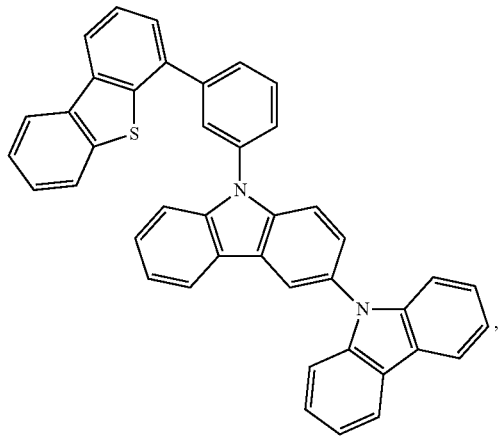

(SH-9)

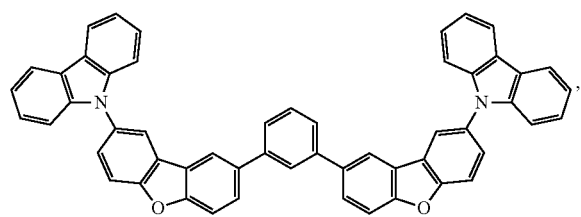

(SH-10)

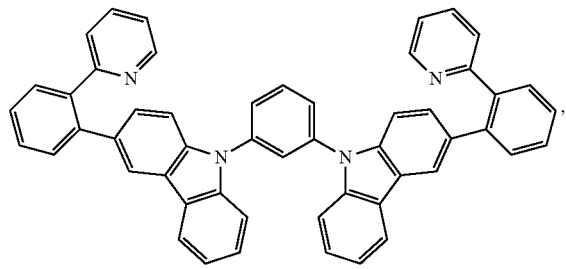

Preferably, the light-emitting layer (C) comprises at least one emitter material and at least one host material. Suitable and preferred emitter materials as well as suitable and preferred host materials are mentioned above.

More preferably, the light-emitting layer (c) comprises at least one emitter material, which emits light in the region of from 400 to 500 nm of the electromagnetic spectrum, more preferably at least one phosphorescence emitter which emits light in the region of from 400 to 500 nm of the electromagnetic spectrum, most preferably at least one emitter material of formula (IV).

Most preferably, the light-emitting layer (c) comprises at least one emitter material, which emits light in the region of from 400 to 500 nm of the electromagnetic spectrum, more preferably at least one phosphorescence emitter which emits light in the region of from 400 to 500 nm of the electromagnetic spectrum, most preferably at least one emitter material of formula (IV) in an amount of 5 to 40% by weight, preferably 5 to 30% by weight, more preferably 5 to 20 by weight, and the at least one host material, preferably at least one host material selected from SH-1, SH-2, SH-3, SH-4, SH-5, SH-6, SH-7, SH-8, SH-9 and SH-10, in an amount of 60 to 95% by weight, preferably 70 to 95% by weight, more preferably 80 to 95% by weight, where the amount of the at least one emitter material and the at least one host material adds up to a total of 100% by weight.

The second host compound can be one compound or it can be a mixture of two or more compounds. The carbene complex Ir(DPBIC)3 which has been described above, or the Ir metal-carbene complex comprising one, two or three, preferably three, bidentate ligands of formula (I) and/or (I'), preferably the Ir metal-carbene complexes of formulae (II), (II') and (II"), more preferably Ir metal-carbene complexes of following formulae (IIa), (II'a), (II"a) and (II"a'), may be added as co-host.

The layer thickness of the light-emitting layer (c) in the inventive OLED is preferably from 1 to 100 nm, more preferably 5 to 60 nm.

Anode (a)

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

The anode materials mentioned above are commercially available and/or prepared by processes known by a person skilled in the art.

Cathode (b)

The cathode (b) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

The cathode materials mentioned above are commercially available and/or prepared by processes known by a person skilled in the art.

Further Layers in the Inventive OLED

Blocking Layer for Holes/Excitons (e)

Among the materials mentioned below as electron transport materials, some may fulfil several functions. For example, some of the electron transport materials are simultaneously hole-blocking materials when they have a low-lying HOMO or exciton-blocking materials when they have a sufficiently high triplet energy. These can be used, for example, in the blocking layer for holes/excitons (e). However, it is likewise possible that the function as a hole/ exciton blocker is also adopted by the layer (f), such that the layer (e) can be dispensed with.

Electron Transport Layer (f)

Electron transport layer may include a material capable of transporting electrons. Electron transport layer may be intrinsic (undoped), or doped. Doping may be used to enhance conductivity. Suitable electron-transporting materials for layer (f) of the inventive OLEDs comprise metals chelated with oxinoid compounds, such as tris(8-hydroxyquinolato)aluminum ($Alq_3$), compounds based on phenanthroline such as 2,9-dimethyl-4,7-diphenyl-1,10phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

The electron-transport materials mentioned above are commercially available and/or prepared by processes known by a person skilled in the art.

It is likewise possible to use mixtures of at least two materials in the electron-transporting layer, in which case at least one material is electron-conducting. Preferably, in such mixed electron-transporting layers, at least one phenanthroline compound is used, preferably BCP, or at least one pyridine compound according to the formula (VIII) below, preferably a compound of the formula (VIIIa) below. More preferably, in mixed electron-transporting layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Waizer, B. Maennig, M. Pfeiffer, K. Leo, Chem. Soc. Rev. 2007, 107, 1233. For example, it is possible to use mixtures which lead to electrical n-doping of the electron-transporting layer. n-Doping is achieved by the addition of reducing materials. These mixtures may, for example, be mixtures of the above-mentioned electron transport materials with alkaline/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP 1786050, or with compounds as described in EP1 837 926 B1.

In a preferred embodiment, the electron transport layer comprises at least one compound of the general formula (VII)

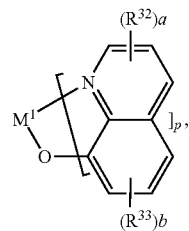

in which
$R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or
two $R^{32}$ and/or $R^{33}$ substituents together form a fused benzene ring which is optionally substituted by one or more $C_1$-$C_8$-alkyl groups;
a and b are each independently 0, or 1, 2 or 3,
$M^1$ is an alkaline metal atom or alkaline earth metal atom,
p is 1 when $M^1$ is an alkali metal atom, p is 2 when $M^1$ is an alkali metal atom.

A very particularly preferred compound of the formula (VII) is

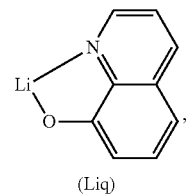

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transporting layer comprises at least one compound of the formula (VIII),

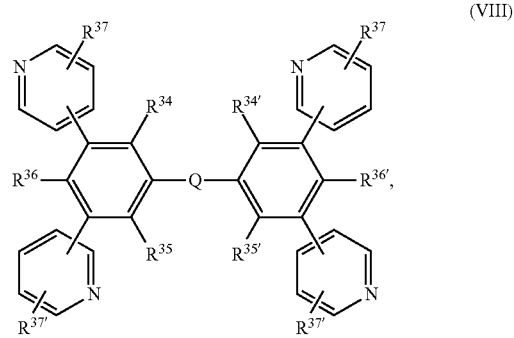

in which
$R^{34}$, $R^{35}$, $R^{36}$, $R^{37}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G,
Q is an arylene or heteroarylene group, each of which is optionally substituted by G;

D is —CO—; —COO—; —S—; —SO—; —SO$_2$—; —O—; —NR$^{40}$—; —SiR$^{45}$R$^{46}$—; —POR$^{47}$—; —CR$^{38}$═CR$^{39}$—; or —C≡C—;

E is —OR$^{44}$; —SR$^{44}$; —NR$^{40}$R$^{41}$; —COR$^{43}$; —COOR$^{42}$; —CONR$^{40}$R$^{41}$; —CN; or F;

G is E, C$_1$-C$_{18}$-alkyl, C$_1$-C$_{18}$-alkyl which is interrupted by D, C$_1$-C$_{18}$-perfluoroalkyl, C$_1$-C$_{18}$-alkoxy, or C$_1$-C$_{18}$-alkoxy which is substituted by E and/or interrupted by D, in which R$^{38}$ and R$^{39}$ are each independently H, C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—;

R$^{40}$ and R$^{41}$ are each independently C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—; or R$^{40}$ and R$^{41}$ together form a 6-membered ring;

R$^{42}$ and R$^{43}$ are each independently C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—, R$^{44}$ is C$_6$-C$_{18}$-aryl; C$_6$-C$_{18}$-aryl which is substituted by C$_1$-C$_{18}$-alkyl or C$_1$-C$_{18}$-alkoxy; C$_1$-C$_{18}$-alkyl; or C$_1$-C$_{18}$-alkyl which is interrupted by —O—, R$^{45}$ and R$^{46}$ are each independently C$_1$-C$_{18}$-alkyl, C$_6$-C$_{18}$-aryl or C$_6$-C$_{18}$-aryl which is substituted by C$_1$-C$_{18}$-alkyl, R$^{47}$ is C$_1$-C$_{18}$-alkyl, C$_6$-C$_{18}$-aryl or C$_6$-C$_{18}$-aryl which is substituted by C$_1$-C$_{18}$-alkyl.

Preferred compounds of the formula (VIII) are compounds of the formula (VIIIa)

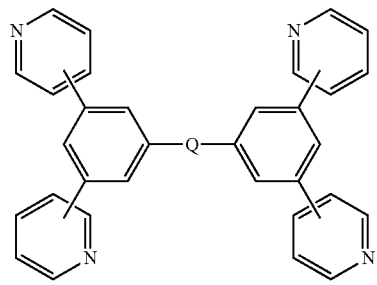
(VIIIa)

in which Q is:

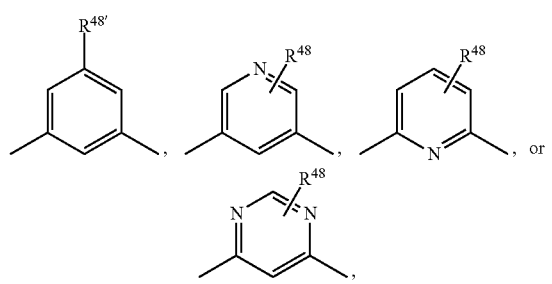

R$^{48}$ is H or C$_1$-C$_{18}$-alkyl and

R$^{48''}$ is H, C$_1$-C$_{18}$-alkyl or

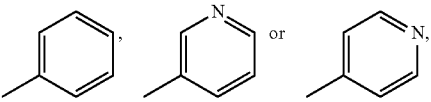

Particular preference is given to a compound of the formula

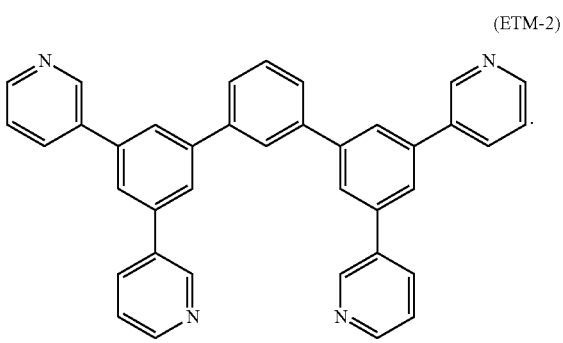 [SMILES: c1cncc(-c2cc(-c3cccnc3)cc(-c3cccc(-c4cc(-c5cccnc5)cc(-c5cccnc5)c4)c3)c2)c1]
(ETM-2)

In a further, very particularly preferred embodiment, the electron transport layer comprises a compound of the formula

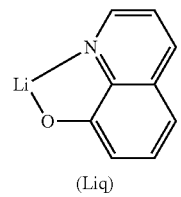
(Liq)

and a compound ETM-2.

In a preferred embodiment, the electron transport layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008-127326, or the compounds can be prepared analogously to the processes disclosed in the aforementioned documents.

It is likewise possible to use mixtures of alkali metal hydroxyquinolate complexes, preferably Liq, and dibenzofuran compounds in the electron transport layer. Reference is made to WO2011/157790. Dibenzofuran compounds A-1 to A-36 and B-1 to B-22 described in WO 2011/157790 are preferred, wherein dibenzofuran compound

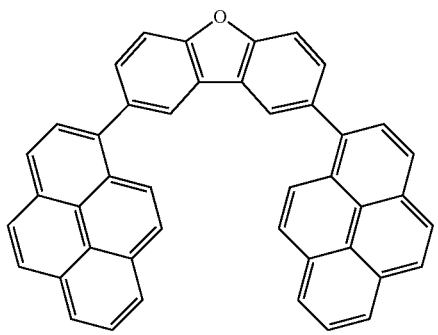

(A-10; = ETM-1)

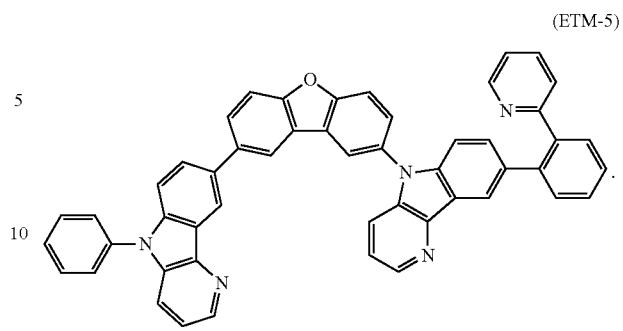

(ETM-5)

Hole Injection Layer (g)

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrene-sulfonate) also called PEDOT/PSS.

The hole injection materials mentioned above are commercially available and/or prepared by processes known by a person skilled in the art.

Electron Injection Layer (h)

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer is most preferred.

In a preferred embodiment, the electron transport layer comprises Liq in an amount of 99 to 1% by weight, preferably 75 to 25% by weight, more preferably about 50% by weight, where the amount of Liq and the amount of the dibenzofuran compound(s), especially ETM-1, adds up to a total of 100% by weight.

In a preferred embodiment, the electron transport layer comprises at least one phenanthroline derivative and/or pyridine derivative.

In a further preferred embodiment, the electron transport layer comprises at least one phenanthroline derivative and/or pyridine derivative and at least one alkali metal hydroxyquinolate complex.

In a further preferred embodiment, the electron transport layer comprises at least one of the dibenzofuran compounds A-1 to A-36 and B-1 to B-22 described in WO2011/157790, especially ETM-1.

In a further preferred embodiment, the electron transport layer comprises a compound described in WO 2012/111462, WO 2012/147397 and US 2012/0261654, such as, for example, a compound of formula (ETM-4)

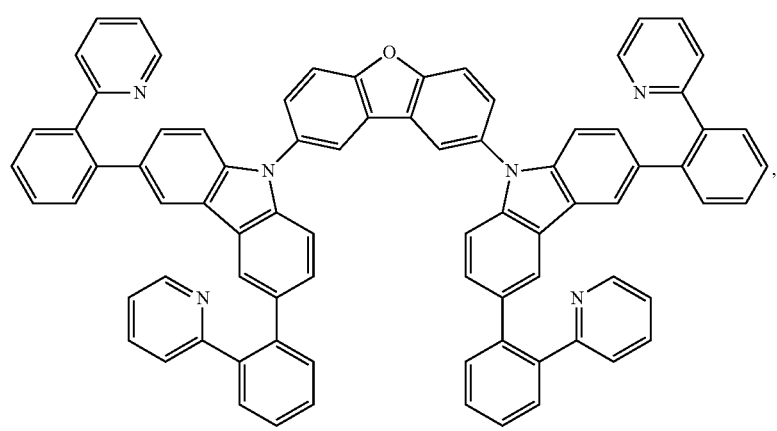

WO 2012/115034, such as for example, such as, for example, a compound of formula (f) and the cathode (b) as an electron injection layer (h) in order to reduce the operating voltage.

The electron injection materials mentioned above are commercially available and/or prepared by processes known by a person skilled in the art.

In general, the different layers in the inventive OLED, if present, have the following thicknesses:
anode (a): 50 to 500 nm, preferably 100 to 200 nm;
a hole injection layer (g): 5 to 100 nm, preferably 20 to 80 nm,
hole-transport layer (d1): 5 to 100 nm, preferably 10 to 80 nm,
electron/exciton blocking layer (d2): 1 to 50 nm, preferably 5 to 10 nm,
light-emitting layer (c): 1 to 100 nm, preferably 5 to 60 nm,
a hole/exciton blocking layer (e): 1 to 50 nm, preferably 5 to 10 nm,
electron-transport layer (g): 5 to 100 nm, preferably 20 to 80 nm,
electron injection layer (h): 1 to 50 nm, preferably 2 to 10 nm,
cathode (b): 20 to 1000 nm, preferably 30 to 500 nm.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive organic electronic device, preferably OLED, can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the organic electronic device, preferably OLED, can be applied from solutions or dispersions in suitable solvents, employing coating techniques known to those skilled in the art.

The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer has/have greater thicknesses than the layer thicknesses specified when they are electrically doped.

Use of at least one Ir metal-carbene complex comprising one, two or three, preferably three, bidentate ligands of formula (I) and/or (I') as hole-transport material and/or electron/exciton blocker material, preferably use of at least one Ir metal-carbene complex comprising one, two or three, preferably three, bidentate ligands of formula (I) and/or (I') as hole-transport material in a hole transport layer of an organic electronic device, preferably of an OLED and/or use of at least one Ir metal-carbene complex comprising one, two or three, preferably three, bidentate ligands of formula (I) and/or (I') as electron/exciton blocker material in an electron-blocking layer of an organic electronic device, preferably of an OLED makes it possible to obtain organic electronic devices, preferably OLEDs with high efficiency and/or with high stability and long lifetimes.

The present invention therefore relates in a further embodiment to the use of an Ir metal-carbene complex comprising one, two or three, preferably three, bidentate ligands of formula (I) and/or (I'), as defined in the specification of the present application as hole-transport material and/or electron/exciton blocker material. Preferred Ir metal-carbene complexes comprising one, two or three, preferably three, bidentate ligands of formula (I) and/or (I') and preferred hole-transport materials and/or electron/exciton blocker materials are mentioned before. Preferred uses of the Ir metal-carbene complexes comprising one, two or three, preferably three, bidentate ligands of formula (I) and/or (I') are also mentioned above.

The organic electronic devices, preferably OLEDs, can be used in all apparatus in which electroluminescence is useful. Suitable devices are preferably selected from the group consisting of stationary visual display units, such as visual display units of computers, televisions, visual display units in printers, kitchen appliances, advertising panels, information panels and illuminations; mobile visual display units such as visual display units in smartphones, cellphones, tablet computers, laptops, digital cameras, MP3-players, vehicles, keyboards and destination displays on buses and trains; illumination units; units in items of clothing; units in furniture and units in wallpaper.

The present invention therefore further relates to apparatus selected from the group consisting of stationary visual display units, such as visual display units of computers, televisions, visual display units in printers, kitchen appliances, advertising panels, information panels and illuminations; mobile visual display units such as visual display units in smartphones, cellphones, tablet computers, laptops, digital cameras, MP3-players, vehicles, keyboards and destination displays on buses and trains; illumination units; units in items of clothing; units in furniture and units in wallpaper, comprising at least one organic electronic device, preferably at least one OLED, according to the present invention or comprising at least one hole transport layer or at least one electron/exciton blocking layer according to the present invention.

In a further embodiment, the Ir metal-carbene complexes comprising one, two or three, preferably three, bidentate ligands of formula (I) and/or (I') can be used in white OLEDs.

The OLEDs may further comprise at least one second light-emitting layer. The overall emission of the OLEDs may be composed of the emission of the at least two light-emitting layers and may also comprise white light, as described for example in EP13160198.1.

In addition, the Ir metal-carbene complexes comprising one, two or three, preferably three, bidentate ligands of formula (I) and/or (I') can be used in OLEDs with inverse structure. The structure of inverse OLEDs and the materials typically used therein are known to those skilled in the art.

It is also possible to stack two OLEDs or to stack three or more OLEDs ("stacked device concept"). These devices usually use a transparent charge generating interlayer such as indium tin oxide (ITO), $V_2O_5$, or an organic p-n junction.

The stacked OLED (SOLED) usually includes at least two individual sub-elements.

Each sub-element comprises at least three layers: an electron transport layer, an emitter layer and a hole-transport layer. Additional layers may be added to a sub-element. Each SOLED sub-element may include for example a hole injection layer, a hole transport layer, an electron/exciton blocking layer, an emitter layer, a hole/exciton blocking layer, an electron transport layer, an electron injection layer. Each SOLED sub-element may have the same layer structure or different layer structure from the other sub-elements.

Suitable SOLED structures are known by a person skilled in the art.

The following examples are included for illustrative purposes only and do not limit the scope of the claims. Unless otherwise stated, all parts and percentages are by weight.

APPLICATION EXAMPLES

Synthesis of BE-12

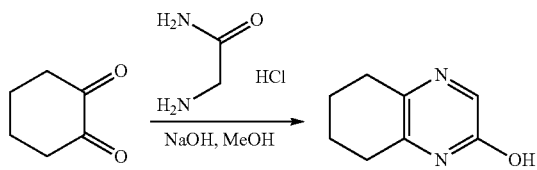 [SMILES: O=C1CCCCC1=O ; NCC(N)=O ; Cl ; Oc1cnc2c(n1)CCCC2]

Synthesis of 5,6,7,8-tetrahydroquinoxalin-2-ol 33.2 g (0.30 mol) of glycinamide hydrochloride are suspended under nitrogen in 120 ml of methanol and cooled down to below −30° C. 33.6 g (0.30 mol) of 1,2-cyclohexandione are dissolved in 120 ml of methanol, cooled to ice-bath temperature, and added to the suspension. The resulting white suspension is slowly treated with 60 ml of 12.5N NaOH at a temperature below −30° C. After addition, the temperature is slowly raised up to room temperature, treated with 40 ml of concentrated HCl, followed by the addition of 11 g of sodium bicarbonate. The resulting beige suspension is filtered and the solid washed with water, and further stirred three times in 200 ml of water. The solid is dried and further recrystallized from 2 l of ethanol, followed by drying under vacuum, giving the title product as off-white solid (yield: 24 g (54%)). $^1$H-NMR (400 MHz, MeOD): •=1.78-1.92 (m, 4H), 2.61-2.73 (m, 4H), 7.88 (s, 1H).

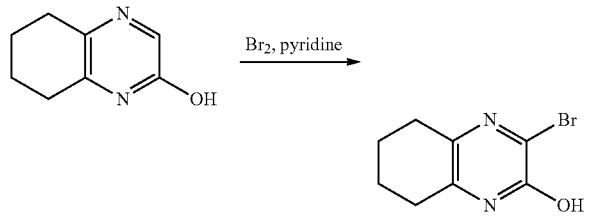

Synthesis of 3-bromo-5,6,7,8-tetrahydroquinoxalin-2-ol 30.0 g (0.20 mol) of 5,6,7,8-tetrahydroquinoxalin-2-ol are suspended under nitrogen in 300 ml of chloroform and 16.6 g (0.21 mol) of pyridine. 32 g (0.20 mol) of bromine are slowly added during one hour at a maximum temperature of −4° C. The yellow suspension is further stirred and the temperature slowly raised to 0° C. The yellow solution is diluted with water and extraction done with 500 ml of dichloromethane. The organic phase is further extracted four times with 200 ml of water, dried with sodium sulfate, providing a clear yellowish solution. Dilution with 600 ml of cyclohexane gives a white precipitate. The suspension is filtered, the solid further washed with 100 ml of cyclohexane and dried under vacuum, giving the title product as a white solid (yield: 45.8 g (75%)). $^1$H-NMR (400 MHz, MeOD): •=1.78-1.90 (m, 4H), 2.54-2.70 (m, 4H).

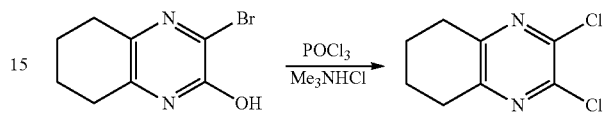

Synthesis of 2,3-dichloro-5,6,7,8-tetrahydroquinoxaline 21.9 g (95.6 mmol) of 3-bromo-5,6,7,8-tetrahydroquinoxalin-2-ol are suspended at room temperature under nitrogen in 124.6 g (0.81 mol) of POCl$_3$, followed by the addition of 45.7 g (0.48 mol) trimethylammonium chloride. The suspension is heated under reflux for two hours. The beige light turbid suspension is cooled down to 50° C. and poured into 500 ml of water. The mixture is further stirred during 15 minutes followed by filtration and subsequent washing of the solid with a large amount of water. The solid is dried under vacuum and recrystallized from cold ethanol giving the title product as off-white solid (yield: 10.2 g (53%)). Melting point: 93-94° C. $^1$H-NMR (400 MHz, MeOD): •=1.89-1.99 (m, 4H), 2.87-2.96 (m, 4H).

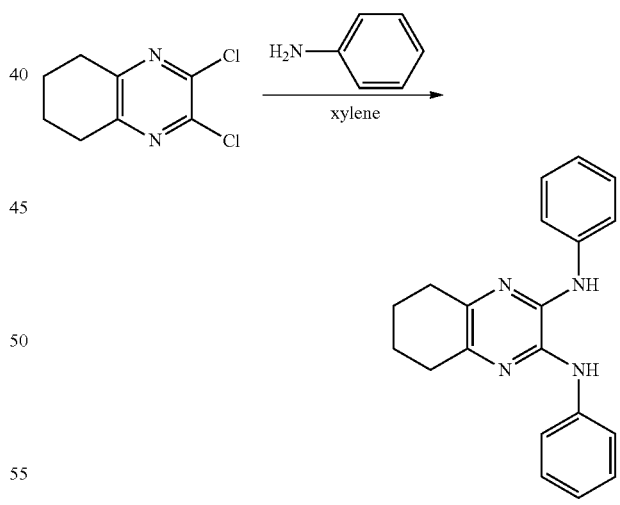

Synthesis of N2,N3-diphenyl-5,6,7,8-tetrahydroquinoxaline-2,3-diamine 28.4 g (0.14 mol) of 2,3-dichloro-5,6,7,8-tetrahydroquinoxaline are suspended under nitrogen in 260 g (2.8 mol) of aniline and the mixture heated at 148° C. for six hours. 250 ml of methanol are added and the mixture cooled down to 10° C. at which point crystallization started. The mixture is further stirred at 5° C. during 15 minutes, followed by filtration, washing with methanol, and drying. The solid is two times stirred in 120 ml of hexane, two times washed with 100 ml of hexane, filtered and dried under vacuum. The solid is recrystallized from 200 mol of ethanol giving the title product as a off-white solid (yield: 36.1 g (82%)). Melting point: 145-146° C. $^1$H-NMR (400 MHz, d$_6$-DMSO): •=1.74-1.84 (m, 4H), 2.60-2.70 (m, 4H), 6.93 (t, 2H), 7.29 (d, 4H), 8.34 (br. s, 2H).

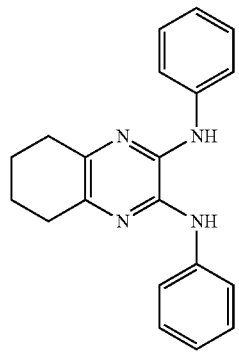 

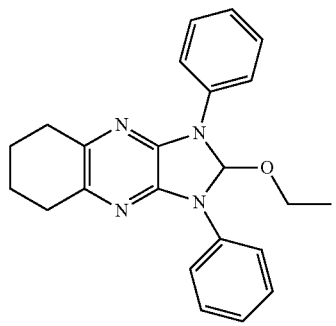

Synthesis of 2-ethoxy-1,3-diphenyl-5,6,7,8-tetra-hydro-2H-imidazo[4,5-b]quinoxaline 15.8 g (0.05 mol) of N2,N3-diphenyl-5,6,7,8-tetrahydroquinoxaline-2,3-diamine are suspended under nitrogen in 148.2 g (1.0 mol) of triethyl orthoformate and heated up to 120° C. Heating is continued for 27 hours, followed by the addition of 50 g of triethyl orthoformate, and stirring continued for four hours at the same temperature, providing a red brownish suspension. The suspension is filtered and the remaining filtrate concentrated under vacuum giving 19.6 g of a brownish oil. The oil is stirred in hot ethanol, cooled down and further stirred in an ice-batch during one hour. The solid is filtered off and further washed with 40 ml of cold ethanol giving the title product as light beige solid (yield: 14.5 g (78%)). $^1$H-NMR (400 MHz, d$_6$-DMSO): •=0.90 (t, 3H), 1.81 (br. m, 4H), 2.71 (br. M, 4H), 3.15 (q, 2H), 7.16 (t, 2H), 7.46 (t, 4H), 7.68 (s, 1H), 8.08 (d, 4H).

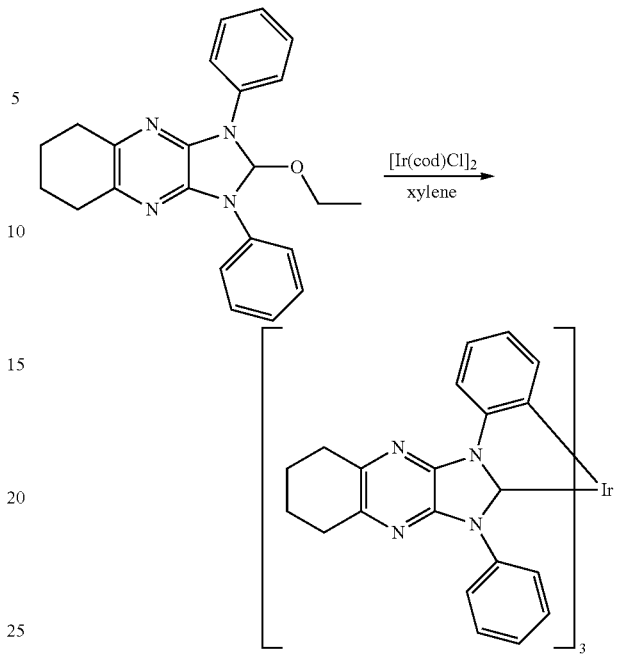

Synthesis of Complex BE-12

9.00 g (24.2 mmol) of 2-ethoxy-1,3-diphenyl-5,6,7,8-tetrahydro-2H-imidazo[4,5-b]quinoxaline and 2.03 g (3.0 mmol) of chloro(1,5-cyclooctadiene)iridium(I) dimer are suspended under argon in 90 ml of o-xylene. The suspension is four times evacuated and backfilled with argon, followed by heating at 132° C. during four hours. The brown solution is diluted with 150 ml of toluene, followed by filtration an washing with 50 ml of toluene. The solid is stirred in 30 ml toluene, followed by stirring three times with 30 ml of ethanol. Stirring in toluene and ethanol is repeated two times, followed by stirring and washing with hexane providing a yellow solid. The solid is recrystallized from 150 ml of 7:3-toluene/2-butanone mixture and washed with the same solvent mixture, followed by ethanol washings, and drying under vacuum, giving the title product as a yellow solid (yield: 4.1 g (58%)). $^1$H-NMR (400 MHz, CD$_2$Cl$_2$): •=1.98 (m, 12H), 2.68-2.80 (m, 3H), 2.82-2.92 (m, 3H), 3.08-3.28 (m, 6H), 6.41-7.21 (m, 24H), 8.79 (d, 3H).

Synthesis of IIa and II″a

The synthesis of IIa has been described in WO2012172482. Separation of the crude reaction mixture by column chromatography yields the two major isomers IIa and II″a in pure form. Isomerization as described in WO2012172482 results in a 90:10 mixture of IIa and II″a which can be used as mixture or also separated by column chromatography. Device data of pure isomers as well as mixtures of these isomers are given below.

Diode Examples

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer Plexcore AJ20-1000 is spun on from solution.

Thereafter, the organic materials specified below are applied by vapor deposition to the cleaned substrate at about $10^{-7}$-$10^{-9}$ mbar at a rate of approx. 0.5-5 nm/min.

All ratios mentioned are weight ratios.

Voltage (V), efficacy (lm/W) and External Quantum Efficiency (EQE) (%) for the devices were measured at 300 cd/m$^2$, whereas the measured values of lifetime of the devices of Comparative Application Examples are set to 100.

I Comparison of the External Quantum Efficiency (EQE) of Devices Comprising Ir(DPBIC)$_3$ as Electron/Exciton Blocking Layer; as Electron/Exciton Blocking Layer and as Co-Host and as Electron/Exciton Blocking Layer and in the Hole-Transport Layer with Devices Comprising Compound IIa as Electron/Exciton Blocking Layer; as Electron/Exciton Blocking Layer and as Co-Host and as Electron/Exciton Blocking Layer and in the Hole-Transport Layer Device 1: Compound IIa as Electron/Exciton Blocking Layer and Compound IIa as Electron/Exciton Blocking Layer and as Co-Host HIL Plexcore AJ20-1000—10 nm Ir(DPBIC)$_3$:MoO$_3$ (50:50)—10 nm X1—40 nm BE-12/SH-3/X2 (10:85:5)—5 nm SH-3—25 nm ETM-2:Liq (50:50)—4 nm KF—100 nm Al

| Example | X1 | X2 | Voltage [V] | LumEff [lm/W] | EQE [%] | CIE$_{x,y}$ |
|---|---|---|---|---|---|---|
| Device 1.1[1] | Ir(DPBIC)$_3$ | Ir(DPBIC)$_3$ | 4.7 | 19.5 | 17.0 | 0.16; 0.28 |
| Device 1.2 | IIa | Ir(DPBIC)$_3$ | 4.5 | 21.0 | 17.9 | 0.16; 0.27 |
| Device 1.3 | IIa | IIa | 4.6 | 20.8 | 17.9 | 0.16; 0.28 |

[1]Comparative example

Device 2: Compound of Formula IIa (Isomeric Mixture) as Electron/Exciton Blocking Layer and in the Hole Transport Layer HIL Plexcore AJ20-1000—10 nm X1:MoO$_3$ (50:50)—10 nm X1—40 nm BE-1/SH-3/Ir(DPBIC)$_3$ (10:85:5)—5 nm SH-3—25 nm ETM-2:Liq (50:50)—4 nm KF-100 nm Al

| Example | X1 | Voltage [V] | LumEff [lm/W] | EQE [%] | CIE$_{x,y}$ |
|---|---|---|---|---|---|
| Device 2.1[1] | Ir(DPBIC)$_3$ | 5.0 | 17.3 | 14.9 | 0.17; 0.30 |
| Device 2.2 | IIa (75:25)[2] | 4.7 | 20.8 | 17.5 | 0.16; 0.29 |

[1]Comparative example
[2]75% by weight IIa and 25% by weight II"a

II Comparison of the External Quantum Efficiency (EQE) and the Lifetime (LT$_{50}$) of Devices Comprising Ir(DPBIC)$_3$ as Electron/Exciton Blocking Layer; as Electron/Exciton Blocking Layer and as Co-Host and as Electron/Exciton Blocking Layer and in the Hole-Transport Layer with Devices Comprising Compound IIa or Compound II"a as Electron/Exciton Blocking Layer: As Electron/Exciton Blocking Layer and as Co-Host and as Electron/Exciton Blocking Layer and in the Hole-Transport Layer Device 3: Compound IIa (isomeric mixture) as electron/exciton blocking layer
HIL Plexcore AJ20-1000—10 nm Ir(DPBIC)$_3$:MoO$_3$ (90:10)—10 nm X1—40 nm BE-1/SH-1 (10:90)—5 nm SH-1—20 nm ETM-1:Liq (50:50)—2 nm KF—100 nm Al

| Example | X1 | Voltage [V] | EQE [%] | CIE$_{x,y}$ | LT$_{50}$ [%] |
|---|---|---|---|---|---|
| Device 3.1[1] | Ir(DPBIC)$_3$ | 4.9 | 15.1 | 0.17; 0.31 | 100 |
| Device 3.2 | IIa (90:10)[2] | 5.1 | 15.4 | 0.17; 0.31 | 108 |

[1]Comparative example
[2]90% by weight IIa and 10% by weight II"a

Device 4: Compound IIa (isomeric mixture) as electron/exciton blocking layer
HIL Plexcore AJ20-1000—10 nm Ir(DPBIC)$_3$:MoO$_3$ (90:10)—10 nm X1—40 nm BE-1/SH 1/Ir(DPBIC)$_3$ (30:60:10)—5 nm SH-1—20 nm ETM-1:Liq (50:50)—2 nm KF—100 nm Al

| Example | X1 | Voltage [V] | LumEff [lm/W] | EQE [%] | CIE$_{x,y}$ | LT$_{50}$ [%] |
|---|---|---|---|---|---|---|
| Device 4.1[1] | Ir(DPBIC)$_3$ | 4.1 | 21.3 | 13.3 | 0.18; 0.36 | 100 |
| Device 4.2 | IIa (90:10)[2] | 3.6 | 31.1 | 17.1 | 0.18; 0.37 | 118 |

[1]Comparative example
[2]90% by weight IIa and 10% by weight II"a

Device 5: Compound II"a as electron/exciton blocking layer and Compound II"a as electron/exciton blocking layer and as co-host
HIL Plexcore AJ20-1000—10 nm Ir(DPBIC)$_3$:MoO$_3$ (50:50)—10 nm X1—40 nm BE-1/SH-1/X2 (30:65:5)—5 nm SH-1—25 nm ETM-2:Liq (50:50)—4 nm KF—100 nm Al

| Example | X1 | X2 | Voltage [V] | LumEff [lm/W] | EQE [%] | CIE$_{x,y}$ | LT$_{50}$ [%] |
|---|---|---|---|---|---|---|---|
| Device 5.1[1] | Ir(DPBIC)$_3$ | Ir(DPBIC)$_3$ | 4.0 | 23.4 | 14.0 | 0.18; 0.38 | 100 |
| Device 5.2 | II"a | Ir(DPBIC)$_3$ | 3.9 | 30.9 | 18.3 | 0.18; 0.36 | 101 |
| Device 5.3 | II"a | II"a | 4.0 | 30.5 | 18.4 | 0.18; 0.37 | 101 |

[1]Comparative example

Device 6: Compound II″a as electron/exciton blocking layer and Compound II″a as electron/exciton blocking layer and as co-host
HIL Plexcore AJ20-1000—10 nm Ir(DPBIC)₃:MoO₃ (50:50)—10 nm X1—40 nm BE-12/SH-3/X2 (10:75:15)—5 nm SH-3—25 nm ETM-2:Liq (50:50)—4 nm KF—100 nm Al

| Example | X1 | X2 | Voltage [V] | LumEff [lm/W] | EQE [%] | CIE$_{x,y}$ | LT$_{50}$ [%] |
|---|---|---|---|---|---|---|---|
| Device 6.1[1] | Ir(DPBIC)₃ | Ir(DPBIC)₃ | 3.2 | 28.6 | 18.1 | 0.15; 0.26 | 100 |
| Device 6.2 | II″a | Ir(DPBIC)₃ | 3.2 | 29.1 | 18.4 | 0.16; 0.27 | 124 |
| Device 6.3 | II″a | II″a | 3.3 | 29.6 | 19.0 | 0.15; 0.27 | 114 |

[1])Comparative example

Device 7: Compound of formula IIa (isomeric mixture) as electron/exciton blocking layer and in the hole transport layer
HIL Plexcore AJ20-1000—10 nm X1:MoO₃ (50:50)—10 nm X1—40 nm BE-1/SH-5/Ir(DPBIC)₃ (10:80:10)—SH-5—25 nm ETM-2:Liq (50:50)—4 nm KF—100 nm Al

| Example | X1 | Voltage [V] | LumEff [lm/W] | EQE [%] | CIE$_{x,y}$ | LT$_{50}$ [%] |
|---|---|---|---|---|---|---|
| Device 7.1[1] | Ir(DPBIC)₃ | 4.6 | 20.1 | 18.5 | 0.15; 0.26 | 100 |
| Device 7.2 | IIa (75:25)[2] | 4.4 | 21.6 | 18.2 | 0.16; 0.26 | 168 |

[1])Comparative example
[2])75% by weight IIa and 25% by weight II″a

Device 8: Compound of formula IIa (isomeric mixture) as electron/exciton blocking layer and in the hole transport layer
HIL Plexcore AJ20-1000—10 nm X1:MoO₃ (50:50)—10 nm X1—60 nm BE-1/SH-4/Ir(DPBIC)₃ (10:85:5)—SH-4—25 nm ETM-1:Liq (50:50)—4 nm KF—100 nm Al

| Example | X1 | Voltage [V] | LumEff [lm/W] | EQE [%] | CIE$_{x,y}$ | LT$_{50}$ [%] |
|---|---|---|---|---|---|---|
| Device 8.1[1] | Ir(DPBIC)₃ | 6.8 | 10.9 | 14.5 | 0.16; 0.26 | 100 |
| Device 8.2 | IIa (75:25)[2] | 6.3 | 13.4 | 17.1 | 0.16; 0.25 | 103 |

[1])Comparative example
[2])75% by weight IIa and 25% by weight II″a

The application examples show that the inventive compounds can increase the device performance, such as lifetime and voltage. In particular the external quantum efficiency can be significantly increased, especially, when the inventive compounds are implemented in the exciton blocking layer.

Also, the inventive compounds can be used in a pure isomeric form or as mixture of cyclometalation isomers without significant impact on the device performance.

In the following, the compounds employed in the device examples mentioned above are shown. Said compounds are commercially available and/or prepared by processes known in the art and mentioned in the specification of the present application.

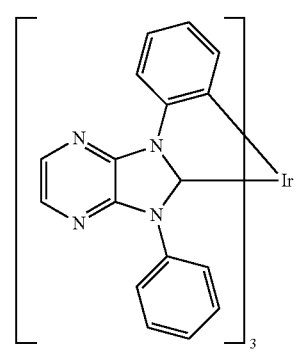

BE-1

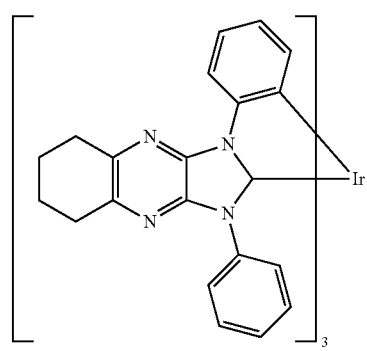

BE-12

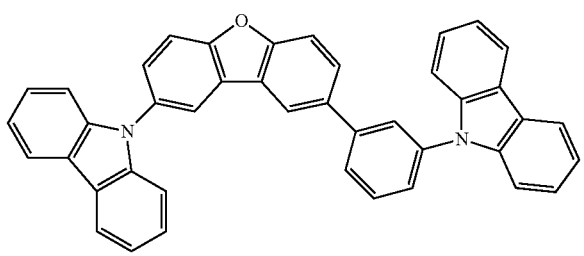

(SH-1)

(SH-3)

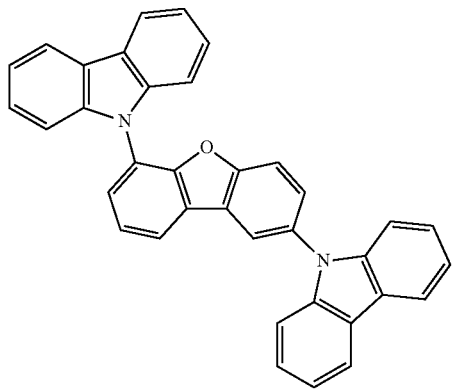

(SH-4)

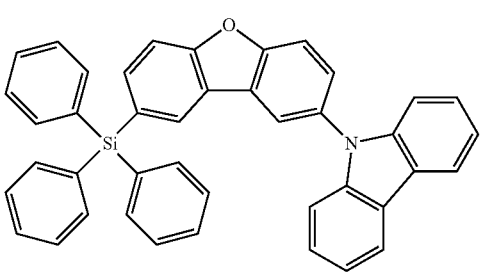

(SH-5)

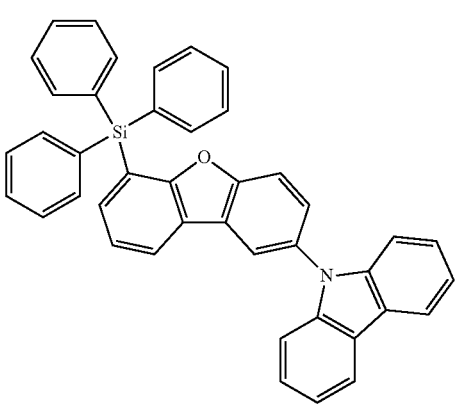

The invention claimed is:
1. An organic electronic device selected from organic light-emitting diodes (OLED), light-emitting electrochemical cells (LEEC), organic photovoltaic cells (OPV) and organic field-effect transistors (OFET),
comprising at least one hole-transport material and/or at least one electron/exciton blocker material, wherein said at least one hole-transport material and/or said at least one electron/exciton blocker material comprises at least one Ir metal-carbene complex of formula (II')

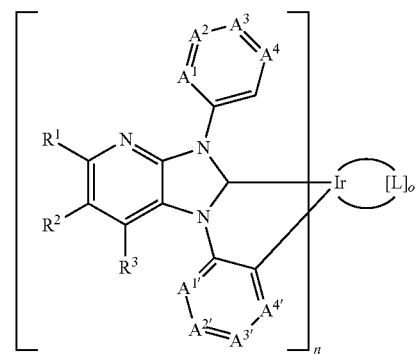

(II')

wherein
$R^1$, $R^2$ and $R^3$
are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action;
or
$R^1$ and $R^2$, or $R^2$ and $R^3$, form, independently of each other, together with a carbon atom to which they are bonded an optionally substituted saturated or unsaturated or aromatic ring, optionally interrupted by at least one heteroatom and having a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;
$A^1$ is $CR^4$ or N;
$A^2$ is $CR^5$ or N;
$A^3$ is $CR^6$ or N;
$A^4$ is $CR^7$ or N;
$A^{1'}$ is $CR^{4'}$ or N;
$A^{2'}$ is $CR^{5'}$ or N;
$A^{3'}$ is $CR^{6'}$ or N;
$A^{4'}$ is $CR^{7'}$ or N;
$R^4$, $R^5$, $R^6$, $R^7$, $R^{4'}$, $R^{5'}$, $R^{6'}$, and $R^{7'}$
are each independently hydrogen, deuterium, a linear or branched alkyl radical, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having from 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action;

or $R^4$ and $R^5$, $R^5$ and $R^6$, $R^6$ and $R^7$, $R^{4'}$ and $R^{5'}$, $R^{5'}$ and $R^{6'}$, or $R^{6'}$ and $R^{7'}$, form, independently of each other, together with the carbon atoms to which they are bonded, a saturated or unsaturated or aromatic, optionally substituted ring, which is optionally interrupted by at least one heteroatom, has a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;

n is 3;
L is not present; and
o is 0;
wherein the OLED comprises
(a) an anode,
(b) a cathode,
(c) a light-emitting layer between the anode and the cathode,
(d) at least one layer, selected from a hole-transport layer (d1) and an electron/exciton blocking layer (d2), disposed between the anode (a) and the light-emitting layer (c);
wherein the at least one hole-transport material is present in the hole-transport layer of the OLED and/or the at least one electron/exciton blocker material is present in the electron/exciton blocking layer of the OLED.

2. The organic electronic device according to claim 1, wherein the at least one hole-transport material is present in a hole transport layer of the organic electronic device and the at least one electron/exciton blocker material is present in an electron/exciton-blocking layer of the organic electronic device.

3. The organic electronic device according to claim 1, wherein the radicals, groups and symbols in the at least one Ir metal-carbene complex have the following meanings:
$R^1$, $R^2$ and $R^3$
are each independently hydrogen, a linear or branched alkyl radical, having from 1 to 6 carbon atoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from the group consisting of halogen radicals, $CF_3$, CN, $SiPh_3$ and $SiMe_3$;

or $R^1$ and $R^2$, or $R^2$ and $R^3$, form, independently of each other, together with a carbon atom to which they are bonded an optionally substituted saturated or unsaturated or aromatic ring, optionally interrupted by at least one heteroatom and having a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;

$A^1$ is $CR^4$;
$A^2$ is $CR^5$;
$A^3$ is $CR^6$;
$A^4$ is $CR^7$;
$A^{1'}$ is $CR^{4'}$
$A^{2'}$ is $CR^{5'}$
$A^{3'}$ is $CR^{6'}$
$A^{4'}$ is $CR^{7'}$
$R^4$, $R^5$, $R^6$, $R^7$, $R^{4'}$, $R^{5'}$, $R^{6'}$ and $R^{7'}$
are each independently hydrogen, deuterium, a linear or branched alkyl radical, optionally bearing at least one functional group, optionally interrupted by at least one heteroatom and having a total of from 1 to 20 carbon and/or heteroatoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from halogen radicals; $CF_3$, CN and $SiMe_3$;

or $R^4$ and $R^5$, $R^5$ and $R^6$, $R^6$ and $R^7$, $R^{4'}$ and $R^{5'}$, $R^{5'}$ and $R^{6'}$, or $R^{6'}$ and $R^{7'}$, form, independently of each other, with the carbon atoms to which they are bonded, a saturated, unsaturated or aromatic, optionally substituted ring, which is optionally interrupted by at least one heteroatom, has a total of from 5 to 18 carbon atoms and/or heteroatoms and may optionally be fused by at least one further optionally substituted saturated or unsaturated aromatic ring, optionally interrupted by at least one heteroatom and having a total of from 5 to 18 carbon atoms and/or heteroatoms.

4. The organic electronic device according to claim 1, wherein the at least one Ir metal-carbene complex has the formula (II'a)

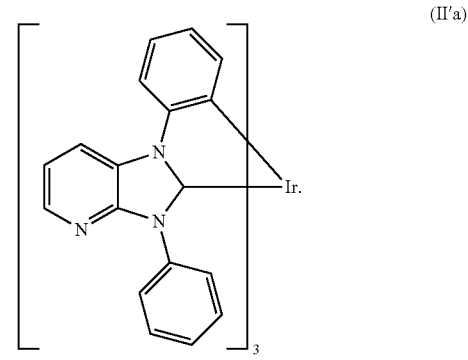

(II'a)

5. The organic electronic device according to claim 1, wherein the at least one hole-transport material and/or at least one electron/exciton blocker material comprises at least one metal oxide.

6. The organic electronic device according to claim 1, wherein the light-emitting layer comprises at least one emitter material, which has an emission maximum $\lambda_{max}$ of from 400 to 500 nm.

7. The organic electronic device according to claim 1, wherein the light-emitting layer comprises at least one phosphorescent emitter material.

8. The organic electronic device according to claim 6, wherein the at least one emitter material is a compound of formula (IV)

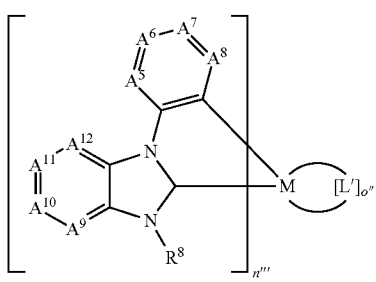

(IV)

wherein

M is Ir, n''' is 1, 2 or 3, $A^9$ is $CR^9$ or N, $A^{10}$ is $CR^{10}$ or N, $A^{11}$ is $CR^{11}$ or N, $A^{12}$ is $CR^{12}$ or N, where 2 of $A^9$, $A^{10}$, $A^{11}$ and $A^{12}$ are nitrogen atoms and at least one carbon atom is present between two nitrogen atoms in the ring;

$R^8$ is a linear or branched alkyl radical, having from 1 to 6 carbon atoms, a substituted or unsubstituted cycloalkyl radical, having from 3 to 20 carbon atoms, a substituted or unsubstituted aryl radical, having from 6 to 30 carbon atoms, a substituted or unsubstituted heteroaryl radical, having a total of from 5 to 18 carbon atoms and/or heteroatoms, $R^9$, $R^{10}$, $R^{11}$ and $R^{12}$ are each independently hydrogen, a linear or branched alkyl radical having 1 to 6 carbon atoms, a substituted or unsubstituted cycloalkyl radical, having from 3 to 20 carbon atoms, a substituted or unsubstituted aryl radical having 6 to 30 carbon atoms, a substituted or unsubstituted heteroaryl radical having a total of 5 to 18 carbon atoms and/or heteroatoms, or $R^{10}$ and $R^{11}$ form, together with the carbon atoms to which they are bonded, an optionally substituted, unsaturated ring optionally interrupted by at least one heteroatom and having a total of 5 to 18 carbon atoms and/or heteroatoms, $A^5$ is $CR^{13}$ or N, $A^6$ is $CR^{14}$ or N, $A^7$ is $CR^{15}$ or N, $A^8$ is $CR^{16}$ or N, $R^{13}$, $R^{14}$, $R^{15}$ and $R^{16}$ are each independently hydrogen, a linear or branched alkyl radical, optionally bearing at least one functional group, optionally interrupted by at least one heteroatom, optionally bearing at least one functional group and having a total of from 1 to 20 carbon atoms and/or heteroatoms, a substituted or unsubstituted cycloalkyl radical, optionally bearing at least one functional group and having from 3 to 20 carbon atoms, a substituted or unsubstituted heterocyclo alkyl radical, interrupted by at least one heteroatom, optionally bearing at least one functional group and having a total of from 3 to 20 carbon atoms and/or heteroatoms, a substituted or unsubstituted aryl radical, optionally bearing at least one functional group and having 6 to 30 carbon atoms, a substituted or unsubstituted heteroaryl radical, interrupted by at least one heteroatom, optionally bearing at least one functional group and having a total of from 5 to 18 carbon atoms and/or heteroatoms, a group with donor or acceptor action;

L' is a monoanionic bidentate ligand, o'' is 0, 1 or 2; and n'''+o'' is 3.

9. An apparatus selected from the group consisting of stationary visual display units, mobile visual display units, illumination units, units in items of clothing, units in furniture and units in wallpaper, wherein the apparatus comprises the organic electronic device according to claim 1.

10. The device of claim 1, wherein the at least one layer is a hole transport layer or an electron/exciton blocking layer; and wherein $R^1$, $R^2$ and $R^3$ are each independently hydrogen, a linear or branched alkyl radical, having from 1 to 6 carbon atoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from the group consisting of halogen radicals, $CF_3$, CN, $SiPh_3$ and $SiMe_3$;

or $R^1$ and $R^2$, or $R^2$ and $R^3$, form, independently of each other, together with a carbon atom to which they are bonded an optionally substituted saturated or unsaturated or aromatic ring, optionally interrupted by at least one heteroatom and having a total of from 5 to 18 carbon atoms and/or heteroatoms, and may optionally be fused to at least one further optionally substituted saturated or unsaturated or aromatic ring, optionally interrupted by at least one heteroatom and having a total of from 5 to 18 carbon atoms and/or heteroatoms;

$A^1$ is $CR^4$;

$A^2$ is $CR^5$;

$A^3$ is $CR^6$;

$A^4$ is $CR^7$;

$A^{1'}$ is $CR^{4'}$;

$A^{2'}$ is $CR^{5'}$;

$A^{3'}$ is $CR^{6'}$;

$A^{4'}$ is $CR^{7'}$;

$R^4$, $R^5$, $R^6$, $R^7$, $R^{4'}$, $R^{5'}$, $R^{6'}$ and $R^{7'}$ are each independently hydrogen, deuterium, a linear or branched alkyl radical, optionally bearing at least one functional group, optionally interrupted by at least one heteroatom and having a total of from 1 to 20 carbon and/or heteroatoms, a substituted or unsubstituted aryl radical, having from 6 to 30 carbon atoms, a substituted or unsubstituted heteroaryl radical, having a total of from 5 to 18 carbon atoms and/or heteroatoms, a group with donor or acceptor action, selected from halogen radicals; $CF_3$, CN and $SiMe_3$;

or $R^4$ and $R^5$, $R^5$ and $R^6$, $R^6$ and $R^7$, $R^{4'}$ and $R^{5'}$, $R^{5'}$ and $R^{6'}$, or $R^{6'}$ and $R^{7'}$, form, independently of each other, with the carbon atoms to which they are bonded, a saturated, unsaturated or aromatic, optionally substituted ring, which is optionally interrupted by at least one heteroatom, has a total of from 5 to 18 carbon atoms and/or heteroatoms and may optionally be fused by at least one further optionally substituted saturated or unsaturated aromatic ring, optionally interrupted by at least one heteroatom and having a total of from 5 to 18 carbon atoms and/or heteroatoms.

11. The organic electronic device according to claim 1, further comprising Ir(DPBIC)$_3$.

* * * * *